US012692509B2

(12) United States Patent
Jiang et al.

(10) Patent No.: US 12,692,509 B2
(45) **Date of Patent: *Jul. 28, 2026**

(54) METHODS FOR GENERATING NEW GENES IN ORGANISM AND USE THEREOF

(71) Applicant: Qingdao Kingagroot Chemical Compound Co., Ltd., Qingdao (CN)

(72) Inventors: Linjian Jiang, Qingdao (CN); Jiyao Wang, Qingdao (CN); Sudong Mo, Qingdao (CN); Bo Chen, Qingdao (CN); Huarong Li, Qingdao (CN)

(73) Assignee: Qingdao Kingagroot Chemical Compound Co., Ltd., Qingdao (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/264,367

(22) PCT Filed: Nov. 5, 2020

(86) PCT No.: PCT/CN2020/126747

§ 371 (c)(1),
(2) Date: May 14, 2021

(87) PCT Pub. No.: WO2021/088923

PCT Pub. Date: May 14, 2021

(65) Prior Publication Data

US 2022/0348950 A1 Nov. 3, 2022

(30) Foreign Application Priority Data

Nov. 6, 2019 (CN) ......................... 201911073406.1
Oct. 30, 2020 (CN) ......................... 202011190279.6

(51) Int. Cl.
*A01H 6/46* (2018.01)
*C07K 14/41* (2006.01)
*C07K 14/415* (2006.01)
*C12N 15/82* (2006.01)

(52) U.S. Cl.
CPC ........... *C12N 15/8274* (2013.01); *A01H 6/46* (2018.05); *C07K 14/415* (2013.01); *C12N 2310/20* (2017.05)

(58) Field of Classification Search
CPC ............ C12N 15/8274; C12N 2310/20; C07K 14/415
See application file for complete search history.

(56) References Cited

U.S. PATENT DOCUMENTS

| | | | |
|---|---|---|---|
| 2003/0041357 | A1 | 2/2003 | Jepson et al. |
| 2004/0123343 | A1 | 6/2004 | La Rosa et al. |
| 2006/0123505 | A1 | 6/2006 | Kikuchi et al. |
| 2007/0016974 | A1 | 1/2007 | Byrum et al. |
| 2007/0039076 | A1 | 2/2007 | Boukharov et al. |
| 2008/0163395 | A1 | 7/2008 | Song et al. |
| 2009/0217414 | A1 | 8/2009 | La Rosa et al. |
| 2014/0059721 | A1 | 2/2014 | Hinga et al. |
| 2014/0259213 | A1 | 9/2014 | Lange et al. |
| 2015/0191739 | A1 | 7/2015 | La Rosa et al. |
| 2019/0136249 | A1 | 5/2019 | Sakai et al. |
| 2022/0364107 | A1 | 11/2022 | Gao et al. |

FOREIGN PATENT DOCUMENTS

| | | | |
|---|---|---|---|
| CN | 105264069 | A | 1/2016 |
| CN | 105753853 | A | 7/2016 |
| CN | 105916987 | A | 8/2016 |
| CN | 106687594 | A | 5/2017 |
| CN | 106795524 | A | 5/2017 |
| CN | 107849581 | A | 3/2018 |
| CN | 108138164 | A | 6/2018 |
| CN | 109475099 | A | 3/2019 |
| CN | 109688807 | A | 4/2019 |
| CN | 110373430 | A | 10/2019 |
| CN | 113105405 | A | 7/2021 |

(Continued)

OTHER PUBLICATIONS

Li et al., 2015, Efficient inversions and duplications of mammalian regulatory DNA elements and gene clusters by CRISPR/Cas9. Journal of molecular cell biology, 7(4), 284-298. (Year: 2015).*
Rodriguez et al., 2011, Distribution of Sun, Ovate, LC, and FAS in the tomato germplasm and the relationship to fruit shape diversity. Plant physiology, 156(1), 275-285. (Year: 2011).*
Huang et al., 2011, Tomato fruit weight 11.3 maps close to fasciated on the bottom of chromosome 11. Theoretical and Applied Genetics, 123, 465-474. (Year: 2011).*
Portin et al., 2017, The evolving definition of the term "gene". Genetics, 205(4), 1353-1364. (Year: 2017).*
Leal et al., 2017, Engineering quantitative trait variation for crop improvement by genome editing. Cell, 171(2), 470-480. (Year: 2017).*
Eddy et al., 2001, Non-coding RNA genes and the modern RNA world. Nature Reviews Genetics, 2(12), 919-929. (Year: 2001).*

(Continued)

*Primary Examiner* — David H Kruse
*Assistant Examiner* — Santosh Sharma
(74) *Attorney, Agent, or Firm* — FINNEGAN, HENDERSON, FARABOW, GARRETT & DUNNER LLP

(57) ABSTRACT

The present invention relates to the technical fields of genetic engineering and bioinformatics, in particular, to a method for creating a new gene in an organism in the absence of an artificial DNA template, and a use thereof. The method comprises simultaneously generating DNA breaks at two or more different specific sites in the organism's genome, wherein the specific sites are genomic sites capable of separating different genetic elements or different protein domains, and the DNA breaks are ligated to each other through non-homologous end joining (NHEJ) or homologous repair to generate a new combination of the different gene elements or different protein domains that is different from the original genome sequence, thereby creating a new gene. The new gene of the invention can change the growth, development, resistance, yield and other traits of the organism, and has great value in application.

14 Claims, 12 Drawing Sheets

Specification includes a Sequence Listing.

(56) References Cited

FOREIGN PATENT DOCUMENTS

| | | | | |
|---|---|---|---|---|
| CO | NC2024/0011901 A | 9/2024 | | |
| CO | NC20240011903 A2 | 9/2024 | | |
| EP | 09163242.2 | 6/2009 | | |
| JP | 5647204 B2 | 12/2014 | | |
| RU | 2018107701 A | 9/2019 | | |
| WO | 2004061122 A2 | 7/2004 | | |
| WO | WO 2006024820 A1 | 3/2006 | | |
| WO | WO 2006037945 A1 | 4/2006 | | |
| WO | WO 2007071900 A1 | 6/2007 | | |
| WO | WO 2007096576 A1 | 8/2007 | | |
| WO | WO 2010143917 A2 | 12/2010 | | |
| WO | WO-2015026883 A1 * | 2/2015 | ............... | A01H 1/02 |
| WO | WO-2016007948 A1 * | 1/2016 | ............... | A01H 1/02 |
| WO | WO 2016061073 A1 | 4/2016 | | |
| WO | 2016081923 A2 | 5/2016 | | |
| WO | WO2016116032 A1 | 7/2016 | | |
| WO | WO 2016120116 A1 | 8/2016 | | |
| WO | WO 2017202768 A1 | 11/2017 | | |
| WO | WO 2018005589 A1 | 1/2018 | | |
| WO | WO 2018019842 A1 | 2/2018 | | |
| WO | 2018165091 A1 | 9/2018 | | |
| WO | 2018235005 A1 | 12/2018 | | |
| WO | 2019086460 A1 | 5/2019 | | |
| WO | WO 2019086510 A1 | 5/2019 | | |
| WO | WO2019118879 A1 | 6/2019 | | |
| WO | 2019203633 A1 | 10/2019 | | |
| WO | 2023160362 A1 | 8/2023 | | |
| WO | 2023185306 A1 | 10/2023 | | |

OTHER PUBLICATIONS

Li et al., 2015, Efficient inversions and duplications of mammalian regulatory DNA elements and gene clusters by CRISPR/Cas9. Journal of molecular cell biology, 7(4), 284-298.(Reference included in IDS submitted on Feb. 8, 2021). (Year: 2015).*

Chen et al., 2022, Enhancing HR frequency for precise genome editing in plants. Frontiers in Plant Science, 13, 883421. (Year: 2022).*

Lermontova et al., 2000, Overexpression of plastidic protoporphyrinogen IX oxidase leads to resistance to the diphenyl-ether herbicide acifluorfen. Plant Physiology, 122(1), 75-84. (Year: 2000).*

Brazda et al. (Published: 2021, Journal: Trends in Genetics, Aug. 2021, vol. 37, No. 8, pp. 730-743 ). (Year: 2021).*

Zheng et al.(Published: 2008, Journal: Methods Mol Biol. 2008 ; 434: 205-219. doi:10.1007/978-1-60327-248-3_13). (Year: 2008).*

Yoon et al. (Published: 2019, Journal: Plant Molecular Biology 101:561-574). (Year: 2019).*

Ofosu et al.(Published:2023, Journal: Agronomy 2023, 13, 1595. https://doi.org/10.3390/agronomy13061595 ). (Year: 2023).*

Genbank: CP018158.1 "*Oryza sativa* Indica Group cultivar Shuhui 498 chromesome 2, partial sequence", 1 page.

Genbank: AP014957.1 "*Oryza sativa* Japonica Group DNA, chromosome 1, cultivar: Nipponbare, complete sequence", 1 page.

J. Li et al., Efficient inversions and duplications of mammalian regulatory DNA elements and gene clusters by CRISPR/Cas9, *Journal of Molecular Cell Biology*, 7(4), pp. 284-298 (2015).

H. Watanabe et al., PL-108 Induction of chromosomal rearrangements using genome editing in *Arabidopsis thaliana*, Proceedings of the 83rd Annual Meeting of the Botanical Society of Janpan, Sendai 2019, Cover page and Publishing details page, Sep. 1, 2019.

Zhou et al., A 1.7-Mb chromosomal inversion downstream of a PpOFP1 gene is responsible for flat fruit shape in peach. *Plant Biotechnol. J.* 19:192-205 (2021).

Cardoso-Moreira et al., Chapter 7: The origin and evolution of new genes. *Evolutionary Genomics: Statistical and Computational Methods*, vol. 2, *Methods in Molecular Biology*, vol. 856:161-186 (2012).

Lu et al., Targeted, efficient sequence insertion and replacement in rice. *Nat. Biotechnol.* 38:1402-1407 (2020).

Schmidt et al., Changing local recombination patterns in *Arabidopsis* by CRISPR/Cas mediated chromosome engineering. *Nat Comm.* 11: 4418 (2020).

Li et al., Efficient inversions and duplications of mammalian regulatory DNA elements and gene clusters by CRISPR/Cas9. *J Mol Cell Biol.* 7:284-298 (2015).

Xing et al., A CRISPR/Cas9 toolkit for multiplex genome editing in plants. *BMC Plant Biol.* 14(1):327 (2014).

Lin et al., Application of protoplast technology to CRISPR/Cas9 mutagenesis: from single—cell mutation detection to mutant plant regeneration. *Plant Biotech. J.* 16:1295-1310 (2018).

Wang et al., Egg cell-specific promoter-controlled CRISPR/Cas9 efficiently generates homozygous mutants for multiple target genes in *Arabidopsis* in a single generation. *Genome Biol.* 16:144 (2015).

V. Bogaert et al., The role of cytochrome P450 monooxygenases in microbial fatty acid metabolism, *FEBS Journal*, 2010, vol. 278, No. 2, pp. 206-221.

B. Urlacher et al., Cytochrome P450 monooxygenases: an update on perspectives for synthetic application, *Trends in Biotechnology*, 2012, vol. 30, No. 1, pp. 26-36.

C. F. Higgins et al., ABC Transporters: From Microorganisms to Man, *Annual Review of Cell Biology*, 1992, 8(1), 67-113.

S. Hyde et al., Structural model of ATP-binding proteing associated with cystic fibrosis, multidrug resistance and bacterial transport, *Nature*, 1990, 346(6282), 362-365.

H. Biedenkapp et al., Viral myb oncogene encodes a sequence-specific DNA-binding activity, *Nature*, 1988, 335(6193), 835-837.

J. Minster et al., Plate Tectonics: An Insider's History of the Modern Theory of the Earth, *Eos*, Transactions American Geophysical Union, 2002, 83(49), 580.

L. Parenicova et al., Molecular and Phylogenetic Analyses of the Complete MADS-Box Transcription Factor Family in *Arabidopsis*: New Openings to the MADS World, *The Plant Cell Online*, 2003, 15(7), 1538-1551.

K. Struhl et al., Molecular Mechanisms of Transcriptional Regulation in Yeast, *Annual Review of Biochemistry*, 1989, 58(1), 1051-1077.

W. Landschulz et al., The DNA binding domain of the rat liver nuclear protein C/EBP is bipartite, *Science*, 1989, 243(4899), 1681-1688.

K. Tew et al., Glutathione S-transferases as emerging therapeutic targets, *Expert Opinion on Therapeutic Targets*, 2001, 5(4), 477-489.

B. Mannervik et al., Nomenclature for human glutathione transferases, *Biochemical Journal*, 1992, 282(1), 305-306.

J. Shi et al., ARGOS8 variants generated by CRISPR-Cas9 improve maize grain yield under field drought stress conditions, *Plant Biotechnology Journal* (2017) 15, pp. 207-216.

F. Zeng et al, Human Genome Editing: Science, Ethics, and Governance, by the National Academy of Sciences, Feb. 2018, pp. 80-81, Shanghai Scientific & Technical Publishers, Shanghai, China.

Y. Zeng et al., Research on molecular biology theory and talent cultivation, Oct. 2017, p. 176, World Publishing Corporation, Xi'an, China.

D. Bauer et al., Generation of Genomic Deletions in Mammalian Cell Lines via CRISPR/Cas9, *Journal of Visualized Experiments*, Jan. 2015, vol. 95, e252118.

L. Ye et al., Genome editing using CRISPR-Cas9 to create the HPFH genotype in HSPCs: An approach for treating sickle cell, *PNAS*, Sep. 20, 2016, vol. 113, No. 38, pp. 10661-10665.

Zhang, Yuchi et al., Analysis on the Patents of Herbicide Resistance Gene at Home and Abroad, *Weed Science*, 2017, vol. 35, No. 2.

International Search Report and Written Opinion for International Application No. PCT/CN2020/126747, mailed Feb. 3, 2021.

C. Schmidt et al., Efficient induction of heritable inversions in plant genomes using the CRISPR /Cas system, *The Plant Journal*, 89(4), pp. 577-589 (2019).

A. Xiao et al., Chromosomal deletions and inversions mediated by TALENs and CRISPR/Cas in zebrafish, *Nucleic Acids Research*, 41(14), pp. 1-11 (2013).

H. Puchta et al., Synthetic nucleases for genome engineering in plants: prospects for a bright future, *The Plant Journal*, 78(5), pp. 727-741 (2013).

(56) References Cited

OTHER PUBLICATIONS

Extended European Search Report in counterpart European application No. 20884099.1 dated Nov. 8, 2023.
M. Davis et al., Gene Activation Using FLP Recombinase in C. elegans, *PLoS Genetics*, 4(3), e1000028, pp. 1-9 (2008).
Andras Nagy, Cre recombinase: The universal reagent for genome tailoring, *Genesis: the Journal of Genetics and Development*, 26(2), pp. 99-109 (2000).
H. Onouchi et al., Operation of an efficient site-specific recombination system of Zygosaccharomyces rouxii in tobacco cells, *Nucleic Acids Research*, 19(23), pp. 6373-6378 (1991).
Examination Report in European Patent Application No. EP20884099.1, dated Oct. 31, 2025.
Jiang, J. et al., *P. Hydroxyphenylpyruvate Dioxygenase* from Medicago sativa is involved in vitamin E biosynthesis and abscisic acid-mediated seed germination, Scientific Reports, vol. 7, No. 1, pp. 1-15 (2017).

* cited by examiner

Scheme 1 Doubling
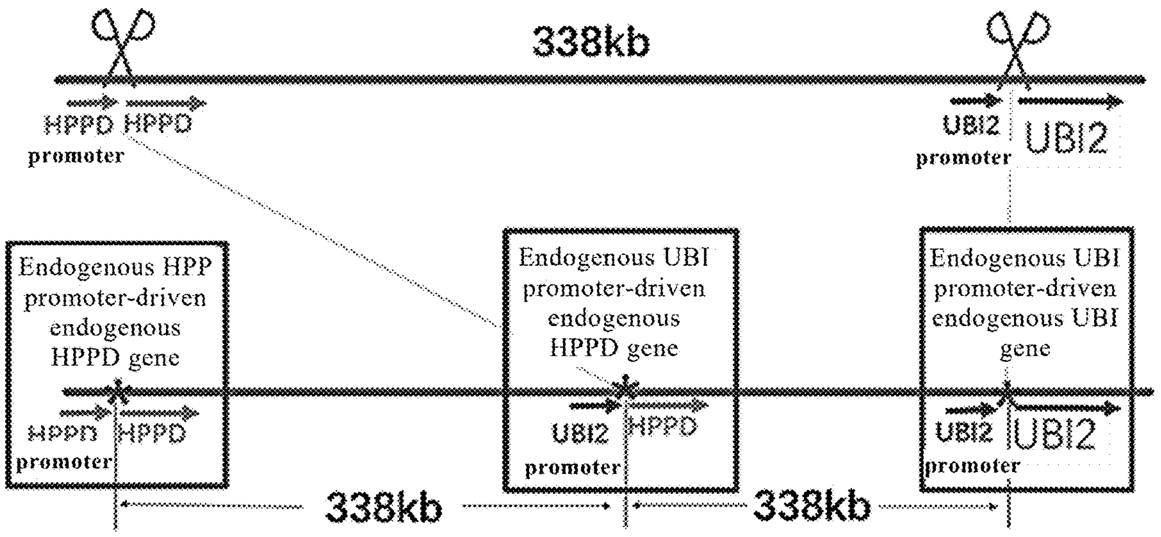
Scheme 2 Two consecutive inversions
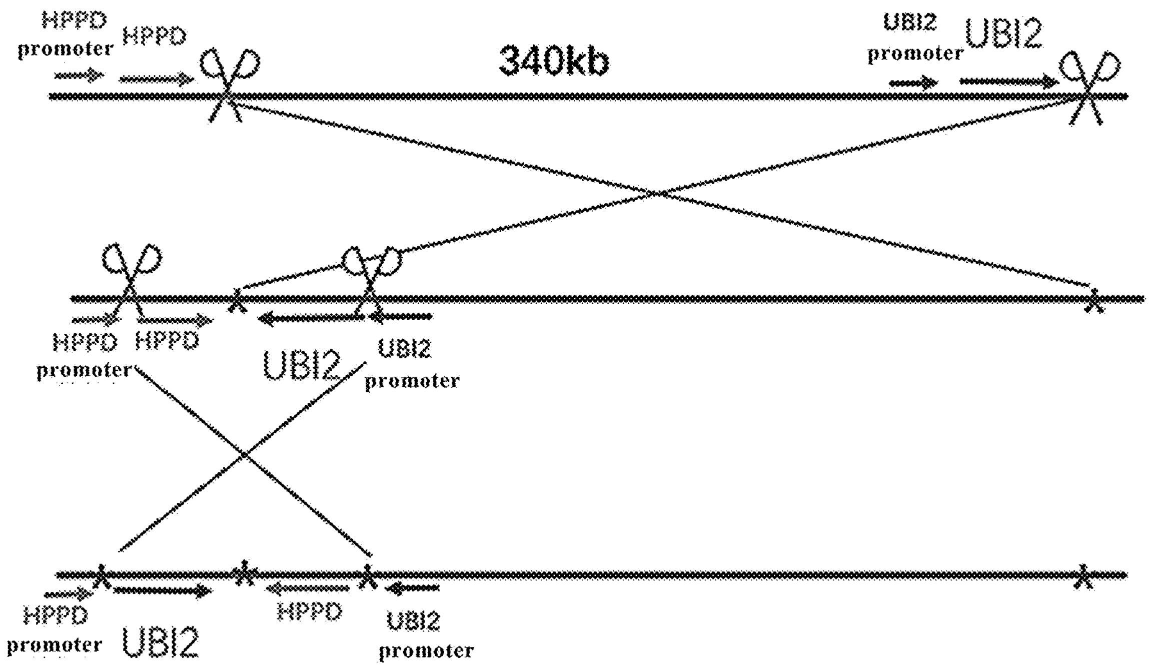
Figure 1

(1)Sequencing result of doubling resulting from pQY002066 vector transformation of protoplast (the underlined part is the Ubiqitin2 gene promoter, the italic part is the HPPD gene expression region)

TTCAAGTCCATAGGCGAGGCGACCGGCCCGCGGCGGACGCGGCGTCGGCGCACCAGAGCTCGACGTGGTGGAACGCGA
GCGCCTGGAACCGGTCGCTCCGCGGGTTGGCGCGGACGAAGCGGCGGTGCCCGACGAGGCGGAACCCCGCGTTCTCCCC
CGCCGCCGCAGCGGCCGAGACGGCGCCGGTGGTGGCGGTGGGGGTGGGAGTGGGAGGCATGGCGCGGCGCGGCGCG
GCGTGGCGTGGCGCGTCGTGGGGTGTGGGGGAGTGGATGACAGTGGCGGCGTGGGGGGAGGAGTTGGTGGTGGGGGG
TTAAATAAAGGGAGGAGATGGCGCCACGTGGACGCTAAGTCTAGTGGTTGCGGACGGGATTTGTCCTCTGGTGCTGGTTG
CCTTGGC*AGATAGGGTAAGAACTAGCACAAGATTAAGGACACAACAACGGATCAAACAGCAAACATATTCCAACAGAACATA*
*CATGTATTCAAAAAGATAGTAACAGGCACATCACACATGTATTCAGATAGGTAGTAACAGCACACGTATCCTGAACTTCATAAA*
*TAAGTAGAATGAACTAGTGGCAATAACTTTTCACACAGAACATCTCCCTTGTTTTCAAATATGTAGTAACAGCACACGTATCCT*
*GTACTTCAAAACTTAGTAGAATGAACTAGTGGCAGTAATCTTTCACACAGAAAGAATGAACTAGTGGCAATAATCTTTCACAC*
*AGAATGTTGGTTGATGGATAG*

(2)Sequencing result of doubling resulting from pQY002068 vector transformation of protoplast (the underlined part is the Ubiqitin2 gene promoter, the italic part is the HPPD gene expression region)

CAACGTGCCTTAGGCGAGGCGACCGGCCCGCGGCGGACGCGGCGTCGGCGCACCAGAGCTCGACGTGGTGGAACGCGA
GCGCCTGGAACCGGTCGCTCCGCGGGTTGGCGCGGACGAAGCGGCGGTGCCCGACGAGGCGGAACCCCGCGTTCTCCCC
CGCCGCCGCAGCGGCCGAGACGGCGCCGGTGGTGGCGGTGGGGGTGGGAGTGGGAGGCATGGCGCGGCGCGGCGCG
GCGTGGCGTGGCGCGTCGTGGGGTGTGGGGGAGTGGATGACAGTGGCGGCGTGGGGGGAGGAGTTGGTGGTGGGGGG
TTAAATAAAGGGAGGAGATGGCGCCACGTGGACGCTAAGTCTAGTGGTTGCGGACGGGATTTGTCCTCTGGTGCTGGTTG
CCTTGG*AGATAGGGTAAGAACTAGCACAAGATTAAGGACACAACAACGGATCAAACAGCAAACATATTCCAACAGAACATAC*
*ATGTATTCAAAAAGATAGTAACAGGCACATCACACATGTATTCAGATAGGTAGTAACAGCACACGTATCCTGAACTTCAGAAAT*
*AAGTAGAATGAACTAGTGGCAATAACTTTTCCCCCCAAAAACCTGTC*

Figure 5

Shuangzuocaotong resistance test for HPPD knock-up lines of QY2091

| 2 g a.i./mu | 4 g a.i./mu | 8 g a.i./mu | 32 g a.i./mu |

(1) Sequencing result of inversion resulting from pQY002062 vector transformation of protoplast (the underlined part is the OsEPSPS expression region, the italic part is the OsTKT promoter)

GGGCGGATTTCGACGGAGGGGCGGAGAGGAGGAGGATCCTGTTGGAGAGCGACTTGGACCCTGGCAGCTGAACCGCCC
CGGAGATCTCCCTGATGGGCTGGAGCACGATCTCCTCCGCCTTCGCCGCCGGCGCTGCCACCGACGACGACGACGCGGAC
GCCACCACCACCGCCTCCCGCCGCCCCCGCGCCCGCACCCGCACCCGCATCCCCCCGCGCGCCGCGGCGGGCAGCCGCAG
CTGCTTCCGCGACGAGAACGCCGCCGACGCCGCCACGGCCTGGTCCAGGGACACCGCCGCCGCAGCCGCGGCGTTGGAC
GCCATGGTCGCCGCCATTGC*GGTGTGGTGGCGAGGAGAGGCGGAGATGGCGAGGTTGTGGGGTGGGAGATGGGATGGG*
*TTATGTATAGACTTGGGGGTGCGTTTTGGGGGGACTCGTAGCCAATAAAAAGGAGGGGGCTATGGTGTGGCCGTTTGGACA*
*T*

(2) Sequencing result of deletion resulting from pQY002062 vector transformation of protoplast (the underlined part is the OsEPSPS expression region, the italic part is the OsTKT expression region)

TTTTCGTTGGAGGGGCGGAGAGGAGGAGGATCCTGTTGGAGAGCGACTTGGACCCTGGCAGCTGAACCGCCCCGGAGAT
CTCCCTGATGGGCTGGAGCACGATCTCCTCCGCCTTCGCCGCCGGCGCTGCCACCGACGACGACGACGCGGACGCCACCA
CCACCGCCTCCCGCCGCCCCCGCGCCCGCACCCGCACCCGCATCCCCCCGCGCGCCGCGGCGGGCAGCCGCAGCTGCTTC
CGCGACGAGAACGCCGCCGACGCCGCCACGGCCTGGTCCAGGGACACCGCCGCCGCAGCCGCGGCGTTGGACGCCATGG
TCGCCGCCATTGGACGAGTCGGAATCGCAGACCGATACCAGGATCTTGCCATCCTATGGAACTGCCTCGGT*CCATGGCCGCG*
*CACTCCGTCGCCGCCGCGCACGCCACCATCGCCGCGCGCGCGGGTGCCGCCGCGCCAGCGCCCGCGCCGCCGGAGCGCCT*
*CGGGTTCCGCCTCAGCGCGCTCGCCGGCCGCGGCCTCCGCTCCCCGCTCCCGCCTCGCCGCGGCGCGCCATCGGCGTCCGC*
*GTCGCGCCGCCGCCACAACAACCGCGTGCGCGCGGCGGCGGTCGAGACGCTCGAGGGGCAGGCGGCGACGGGGGCGCT*
*GCTCGAGAAGTCGGAAACCCCCGAATCCAAA*

(3) Sequencing result of inversion resulting from pQY002093 vector transformation of protoplast (the underlined part is the OsTKT expression region, the italic part is the OsTKT inversion promoter)

GAACGATGCGAGCCCCACGCTCGACCGCCGCCGCGCGCACGCGGTTGTTGTGGCGGCGGCGCGACGCGGACGCCGATGG
CGCGCCGCGGCGAGGCGGGAGCGGGGAGCGGAGGCCGCGGCCGGCGAGCGCGCTGAGGCGGAACCCGAGGCGCTCC
GGCGGCGCGGGCGCTGGCGCGGCGGCACCCGCGCGCGCGGCGATGGTGGCGTGCGCGGCGGCGACGGAGTGCGCGGC
CATGGCGAGAGGAGTG*GATGGTCACCTGACTACCGGTCCCCTCAAACTGGTTTAATTTCCCCTGGCAAAATCCACCTCCGGA*
*CCTACAATTTAAGCTCCCCTTTTTTTTTTTAAAAAAAAAAAAAAAGAGGGTAAACCAACTAACCTAGCTTGGACCTTTTTTAA*
*TGGAGTAAGGGATTTAAAACAAAAACAAAAAAAAAATCCAAACTGGTAAAAAAACAAACAAACCATTTAAATAAAAATTTTC*
*CCCAAAGGGAAATTCCTGGCGAAAAAAATCTATGCCCCTCTGGGTCTATCTTGGTATTTTTTCCCCGGGGCTCCGTTTCATCC*
*TTCATTTTGGCGAATACAAAAAAAACCGTTTGAATTTTTTTTTGGTTGAAAGAATGGCAATTTACTGGCCAGGATCATGTACTC*
*TGCATCTAAGAATTGATTTTTTGACCCCAAATTTCAACTTAGCCTCCATCGCAGTAGTGCGCACACACAGGCTGAAGGTGACT*
*CTTAGACCCAATGTCACTATCTCAGCAATATGCAGAGAGAATGACCCAA*

(4) Sequencing result of deletion resulting from pQY002093 vector transformation of protoplast (the underlined part is the OsTKT expression region, the italic part is the OsEPSPS promoter)

AGAACGATGCGCAGCCTCGGCGTCTCGACCGCCGCCGCGCGCACGCGGTTGTTGTGGCGGCGGCGCGACGCGGACGCCG
ATGGCGCGCCGCGGCGAGGCGGGAGCGGGGAGCGGAGGCCGCGGCCGGCGAGCGCGCTGAGGCGGAACCCGAGGCG
CTCCGGCGGCGCGGGCGCTGGCGCGGCGGCACCCGCGCGCGCGGCGATGGTGGCGTGCGCGGCGGCGACGGAGTGCG
CGGCCATGGCGAGAGGAGTG*TGGTGGGTACCCTTTCAAACCCCCAAAAGAGTGGGTCGGGTCTCTCTTTCGGCTCTCGGC*
*GGGGGCTGCTTCCCACAAAGACCGCCATCAGACGTGAGTGAACTGCAAGTCTGCAACTACCACTCCAGGTGCTCTCCCCTTA*
*AATTACTTTACTACTACCTTTATTCTAGGGGCCGGTTCAGATAATTGCCAAAATCACTCGCACCATTTTTTAATAATATTAGGATG*
*AAATATATATGTCGCGCCAAATTTTTCTACTGTTACTGAAATTTGGACACAAACTACACACCACCGTATATTTATCTTTTTTACCA*
*AATAGGGGTATGGTTTAAAATGACTTTAATCTAAATAGGCCCTGAAATATAAAAGCGCCCCACCCCTCA*

Figure 15

2081 resistance test for QY2234 PPO1 inversion lines 0.18 g a.i./mu 0.4 g a.i./mu 0.6 g a.i./mu 2081 resistance test for QY2234/H5-851 T1 generation at seedling stage

METHODS FOR GENERATING NEW GENES IN ORGANISM AND USE THEREOF

This application contains a Sequence Listing electronically submitted via EFS-Web to the United States Patent and Trademark Office as an ASCII text file entitled "Substitute Sequence Listing 2.txt" having a size of 73,660 bytes and created on Jun. 7, 2023. The information contained in the Sequence Listing is incorporated by reference herein.

CROSS-REFERENCE TO RELATED APPLICATION

This application is a national stage filing under 35 U.S.C. § 371 of International Application No. PCT/CN2020/126747, filed Nov. 5, 2020, which claims the priority and benefits of Chinese Patent Application Nos. 201911073406.1, filed Nov. 6, 2019, and 202011190279.6, filed Oct. 30, 2020, all of which are incorporated herein by reference.

TECHNICAL FIELD

The present invention relates to the technical fields of genetic engineering and bioinformatics, and in particular, a method for creating a new gene in an organism in the absence of an artificial DNA template, and use thereof.

BACKGROUND ART

Generally speaking, a complete gene expression cassette in an organism comprises a promoter, 5' untranslated region (5' UTR), coding region (CDS) or non-coding RNA region (Non-coding RNA), 3' untranslated region (3' UTR), a terminator and many other elements. Non-coding RNA can perform its biological functions at the RNA level, including rRNA, tRNA, snRNA, snoRNA and microRNA. The CDS region contains exons and introns. After the transcribed RNA is translated into a protein, the amino acids of different segments usually form different domains. The specific domains determine the intracellular localization and function of the protein (such as nuclear localization signal, chloroplast leading peptide, mitochondrial leading peptide, DNA binding domain, transcription activation domain, enzyme catalytic center, etc.). For non-coding RNA, different segments also have different functions. When one or several elements of a gene change, a new gene will be formed, which may have new functions. For example, an inversion event of a 1.7 Mb chromosome fragment occurred upstream of the PpOFP1 gene of flat peach may result in a new promoter, which will significantly increase the expression of PpOFP1 in peach fruit with flat shape in the S2 stage of fruit development as compared to that in peach fruit with round shape, thereby inhibit the vertical development of peach fruit and result in the flat shape phenotype in flat peach (Zhou et al. 2018. A 1.7-Mb chromosomal inversion downstream of a PpOFP1 gene is responsible for flat fruit shape in peach. Plant Biotechnol. J. DOI: 10.1111/pbi.13455).

The natural generation of new genes in biological genomes requires a long evolutionary process. According to the research work, the molecular mechanisms for the generation of new genes include exon rearrangement, gene duplication, retrotransposition, and integration of movable elements (transposons, retrotransposons), horizontal gene transfer, gene fusion splitting, de novo origination, and many other mechanisms, and new genes may be retained in species under the action of natural selection through the derivation and functional evolution. The relatively young new genes that have been identified in fruit flies, *Arabidopsis thaliana*, and primates have a history of hundreds of thousands to millions of years according to a calculation (Long et al. 2012. The origin and evolution of new genes. Methods Mol Biol. DOI: 10.1007/978-1-61779-585-5_7). Therefore, in the field of genetic engineering and biological breeding, taking plants as an example, if it is desired to introduce a new gene into a plant (even if all the genetic elements of the new gene are derived from different genes of the species itself), it can only be achieved through the transgenic technology. That is, the elements from different genes are assembled together in vitro to form a new gene, which is then transferred into the plant through transgenic technology. It is characterized in that the assembly of new gene needs to be carried out in vitro, resulting in transgenic crops.

The gene editing tools represented by CRISPR/Cas9 and the like can efficiently and accurately generate double-strand breaks (DSB) at specific sites in the genome of an organism, and then the double-strand breaks (DSB) are repaired through the cell's own non-homologous end repair or homologous recombination mechanisms, thereby generating site-specific mutations. The current applications of the gene editing technique mainly focus on the editing of the internal elements of a single gene, mostly the editing of a CDS exon regio. Editing an exon usually results in frameshift mutations in the gene, leading to the function loss of the gene. For this reason, the gene editing tools such as CRISPR/Cas9 are also known as gene knockout (i.e., gene destruction) tools. In addition to the CDS region, the promoter, 5'UTR and other regions can also be knocked out to affect the expression level of a gene. These methods all mutate existing genes without generating new genes, so it is difficult to meet some needs in production. For example, for most genes, the existing gene editing technology is difficult to achieve the up-regulation of gene expression, and it is also difficult to change the subcellular localization of a protein or change the functional domain of protein. There are also reports in the literature of inserting a promoter or enhancer sequence upstream of an existing gene to change the expression pattern of the gene so as to produce new traits (Lu et al. 2020. Targeted, efficient sequence insertion and replacement in rice. Nat Biotechnol. DOI: 10.1038/s41587-020-0581-5), but this method requires the provision of foreign DNA templates, so strict regulatory procedures similar to genetically modified crops apply, and the application is restricted.

SUMMARY OF THE INVENTION

In order to solve the above-mentioned problems in the prior art, the present invention provides a method for creating a new gene in an organism in the absence of an artificial DNA template by simultaneously generating two or more DNA double-strand breaks at a combination of specific sites in the organism's genome, and use thereof.

In one aspect, the present invention provides a method for creating a new gene in an organism, comprising the following steps:

simultaneously generating DNA breaks at two or more different specific sites in the organism's genome, wherein the specific sites are genomic sites capable of separating different genetic elements or different protein domains, ligating the DNA breaks to each other by a non-homologous end joining (NHEJ) or homologous repair, generating a new combination of the different gene elements or different protein domains that is different from the original genome sequence, thereby creating the new gene.

In one specific embodiment, the "two or more different specific sites" may be located on the same chromosome or on different chromosomes. When they locate on the same chromosome, the chromosome fragment resulting from the DNA breaks simultaneously occurring at two specific sites may be deleted, inversed or replicating doubled after repair; when they locate on different chromosomes, the DNA breaks generated at two specific sites may be ligated to each other after repair to produce a crossover event of the chromosome arms. These events can be identified and screened by PCR sequencing with specifically designed primers.

In a specific embodiment, the "two or more different specific sites" may be specific sites on at least two different genes, or may be at least two different specific sites on the same gene.

In a specific embodiment, the transcription directions of the "at least two different genes" may be the same or different (opposite or toward each other).

In a specific embodiment, the "DNA breaks" are produced by delivering a nuclease with targeting property into a cell of the organism to contact with the specific sites of the genomic DNA. There is no essential difference between this type of DNA breaks and the DNA breaks produced by traditional techniques (such as radiation or chemical mutagenesis).

In a specific embodiment, the "nuclease with targeting property" is selected from Meganuclease, Zinc finger nuclease (ZFN), TALEN, and the CRISPR/Cas system.

Among them, the CRISPR/Cas system can generate two or more DNA double-strand breaks at different sites in the genome through two or more leading RNAs targeting different sequences; by separately designing the ZFN protein or TALEN protein in two or more specific site sequences, the Zinc finger nuclease and TALEN systems can simultaneously generate DNA double-strand breaks at two or more sites. When two breaks are located on the same chromosome, repair results such as deletion, inversion and doubling may occur; and when two breaks are located on two different chromosomes, crossover of chromosomal arms may occur. The deletion, inversion, doubling and exchange of chromosome segments at two DNA breaks can recombine different gene elements or protein domains, thereby creating a new functional gene.

In a specific embodiment, the "nuclease with targeting property" exists in the form of DNA.

In another specific embodiment, the "nuclease with targeting property" exists in the form of mRNA or protein, rather than the form of DNA.

In a specific embodiment, the method for delivering the nucleases with targeting property into the cell is selected from a group consisting of: 1) PEG-mediated cell transfection; 2) liposome-mediated cell transfection; 3) electric shock transformation; 4) microinjection; 5) gene gun bombardment; or 6) *Agrobacterium*-mediated transformation.

The "gene elements" comprise a promoter, a 5' untranslated region (5'UTR), a coding region (CDS) or non-coding RNA region (Non-coding RNA), a 3' untranslated region (3'UTR) and a terminator of the gene.

In a specific embodiment, the combination of different gene elements refers to a combination of the promoter of one of the two genes with different expression patterns and the CDS or non-coding RNA region of the other gene.

In a specific embodiment, one of the combinations of different gene elements refers to a strong endogenous promoter in the organism, and the other is a coding region of the HPPD, EPSPS, PPO or GH1 gene.

In another specific embodiment, the combination of different gene elements refers to a combination of a region from the promoter to the 5'UTR of one of two genes with different expression patterns and the CDS or non-coding RNA region of the other gene.

In a specific embodiment, the "different expression patterns" refer to different levels of gene expression.

In another specific embodiment, the "different expression patterns" refer to different tissue-specificities of gene expression.

In another specific embodiment, the "different expression patterns" refer to different developmental stage-specificities of gene expression.

In another specific embodiment, the combination of different gene elements is a combination of adjacent gene elements within the same gene.

The "protein domains" refer to a DNA fragment corresponding to a specific functional domain of a protein; it includes but is not limited to nuclear localization signal, chloroplast leading peptide, mitochondrial leading peptide, phosphorylation site, methylation site, transmembrane domain, DNA binding domain, transcription activation domain, receptor activation domain, enzyme catalytic center, etc.

In a specific embodiment, the combination of different protein domains refers to a combination of a localization signal region of one of two protein coding genes with different subcellular localizations and a mature protein coding region of the other gene.

In a specific embodiment, the "different subcellular locations" include, but are not limited to, a nuclear location, a cytoplasmic location, a cell membrane location, a chloroplast location, a mitochondrial location, or an endoplasmic reticulum membrane location.

In another specific embodiment, the combination of different protein domains refers to a combination of two protein domains with different biological functions.

In a specific embodiment, the "different biological functions" include, but are not limited to, recognition of specific DNA or RNA conserved sequence, activation of gene expression, binding to protein ligand, binding to small molecule signal, ion binding, or specific enzymatic reaction.

In another specific embodiment, the combination of different protein domains refers to a combination of adjacent protein domains in the same gene.

In another specific embodiment, the combination of gene elements and protein domains refers to a combination of protein domains and adjacent promoters, 5'UTR, 3'UTR or terminators in the same gene.

Specifically, the exchange of promoters of different genes can be achieved by inversion of chromosome fragments: when two genes located on the same chromosome have different directions, DNA breaks can be generated at specific sites between the promoter and CDS of each of the two genes, the region between the breaks can be inverted, thereby the promoters of these two genes would be exchanged, and two new genes would be generated at both ends of the inverted chromosome segment. The different directions of the two genes may be that their 5' ends are internal, namely both genes are in opposite directions, or their 5' ends are external, namely both genes are towards each other. Where the genes are in opposite directions, the promoters of the genes would be inverted, as shown in Scheme 1 of FIG. 2; where the genes are towards each other, the CDS regions of the genes would be inverted, as shown in Scheme 1 of FIG. 4. The inverted region can be as short as less than 10 kb in length, with no other genes therebetween; or the inverted region can be very long, reaching up to 300 kb-3 Mb, and containing hundreds of genes.

It is also possible to create a new gene by doubling a chromosome fragment: where two genes located on the same chromosome are in the same direction, DNA breaks can be generated in specific sites between the promoter and CDS of each of the two genes, the region between the breaks can be doubled by duplication, and a new gene would be created at the junction of the doubled segment by fusing the promoter of the downstream gene to the the CDS region of the upstream gene, as shown in FIG. 1 Scheme 1 and FIG. 3. The length of the doubled region can be in the range of 500 bp to 5 Mb, which can be very short with no other genes therebetween, or can be very long to contain hundreds of genes. Although this method will induce point mutations in the regions between the promoters and the CDS region of the original two genes, such small-scale point mutations generally have little effect on the properties of the gene expression, while the new genes created by promoter replacement will have new properties of expression. Or alternatively, DNA breaks can be generated at specific positions on both sides of a protein domain of a same gene, and the region between the breaks can be doubled by duplication, thereby creating a new gene with doubled specific functional domains.

In another aspect, the present invention provides a method for creating a new gene in an organism, comprising the following steps:

generating DNA breaks at specific sites on at least two different genes at the level of genome or chromosome of the organism, inducing transfer, doubling, inversion or deletion of DNA, so that a specific gene element of one endogenous gene and a gene element on another endogenous gene would be ligated together through non-homologous end joining (NHEJ) or homologous repair, thereby creating a new gene.

The present invention also provides a new gene obtainable by the present method.

Compared with the original genes, the new gene may have different promoter and therefore have expression characteristics in terms of tissues or intensities or developmental stages, or have new amino acid sequences.

The "new amino acid sequence" can either be a fusion of the whole or partial coding regions of two or more gene, or a doubling of a partial protein coding region of the same gene.

In a specific embodiment, the new gene is a highly expressing endogenous HPPD, EPSPS, PPO or GH1 gene in an organism.

The present invention also provides a DNA containing the gene.

The present invention also provides a protein encoded by the gene, or biologically active fragment thereof.

The present invention also provides a recombinant expression vector, which comprises the gene and a promoter operably linked thereto.

The present invention also provides an expression cassette containing the gene.

The present invention also provides a host cell, which comprises the expression cassette. Preferably, the host cell is a plant cell, an animal cell or a fungal cell.

The present invention further provides an organism regenerated from the host cell.

The present invention further provides use of the gene in conferring or improving a resistance/tolerance trait or growth advantage trait in an organism.

The present invention further provides a composition, which comprises:

(a) the promoter of one of two genes with different expression patterns and a coding region or non-coding RNA region of the other gene;

(b) a region between the promoter and the 5' untranslated region of one of two genes with different expression patterns and a coding region or non-coding RNA region of the other gene;

(c) adjacent gene elements within the same gene;

(d) a localization signal region of one of the two protein coding genes with different subcellular localizations and a mature protein coding region of the other gene;

(e) two protein domains with different biological functions;

(f) adjacent protein domains in the same gene; or, (g) a protein domain and an adjacent promoter, 5' untranslated region, 3' non-coding region or terminator in the same gene.

In a specific embodiment, the "different expression patterns" refers to different levels of gene expression.

In another specific embodiment, the "different expression patterns" refers to different tissue-specificities of gene expression.

In another specific embodiment, the "different expression patterns" refers to different developmental stage-specificities of gene expression.

In a specific embodiment, the "different subcellular locations" include, but are not limited to, nuclear location, cytoplasmic location, cell membrane location, chloroplast location, mitochondrial location, or endoplasmic reticulum membrane location.

In a specific embodiment, the "different biological functions" include, but are not limited to, recognition of specific DNA or RNA conserved sequence, activation of gene expression, binding to protein ligand, binding to small molecule signal, ion binding, or specific enzymatic reaction.

In a specific embodiment, the composition is fused in vivo.

In particular, the present invention also provides an editing method of increasing the expression level of a target endogenous gene in an organism independent of an exogenous DNA donor fragment, which comprises the following steps: simultaneously generating DNA breaks at specific sites between the promoter and the CDS of each of the target endogenous gene and an optional endogenous highly-expressing gene; ligating the DNA breaks to each other via non-homologous end joining (NHEJ) or homologous repair to form an in vivo fusion of the coding region of the target endogenous gene and the optional strong endogenous promoter, thereby creating a new highly-expressing endogenous gene. This method is named as an editing method for knocking-up an endogenous gene.

In a specific embodiment, the target endogenous gene and the optional highly-expressing endogenous gene are located on the same chromosome.

In another specific embodiment, the target endogenous gene and the optional highly-expressing endogenous gene are located on different chromosomes.

In another aspect, the present invention provides an editing method for knocking up the expression of an endogenous HPPD gene in a plant, comprising fusing the coding region of the HPPD gene with a strong plant endogenous promoter in vivo to form a new highly-expressing plant endogenous HPPD gene. That is, simultaneously generating DNA breaks at specific sites between the promoter and the CDS of each of the HPPD gene and an optional endogenous highly-expressing gene, ligating the DNA breaks to each other through an intracellular repair pathway to form an in vivo fusion of the coding region of the HPPD gene and the optional endogenous strong promoter, thereby creating a new highly-expressing HPPD gene. In rice, the strong promoter is preferably a promoter of the ubiquitin2 gene.

The present invention also provides a highly-expressing plant endogenous HPPD gene obtainable by the above editing method.

The present invention also provides a highly-expressing rice endogenous HPPD gene which has a sequence selected from the group consisting of:

(1) a nucleic acid sequence as shown in SEQ ID NO: 9, SEQ ID NO: 10, SEQ ID NO: 18 or SEQ ID NO: 19 or a partial sequence thereof, or a complementary sequence thereof;

(2) a sequence having an identity of at least 75%, at least 80%, at least 85%, at least 90%, at least 95%, at least 98% or at least 99% to any one of the sequences as defined in (1); or (3) a nucleic acid sequence capable of hybridizing to the sequence as shown in (1) or (2) under a stringent condition.

In another aspect, the present invention provides an editing method for knocking up the expression of an endogenous EPSPS gene in a plant, which comprises fusing the coding region of an EPSPS gene with a strong plant endogenous promoter in vivo to form a new highly-expressing plant endogenous EPSPS gene. That is, simultaneously generating DNA breaks at specific sites between the promoter and the CDS of each of the EPSPS gene and an optional highly-expressing endogenous gene, ligating the DNA breaks to each other through an intracellular repair pathway to form an in vivo fusion of the coding region of the EPSPS gene and the optional strong endogenous promoter, thereby creating a new highly-expressing EPSPS gene. In rice, the strong promoter is preferably a promoter of the TKT gene.

The present invention also provides a highly-expressing plant endogenous EPSPS gene obtainable by the above editing method.

The present invention also provides a highly-expressing rice endogenous EPSPS gene which has a sequence selected from the group consisting of:

(1) the nucleic acid sequence as shown in SEQ ID NO: 11, SEQ ID NO: 12, SEQ ID NO: 13 or SEQ ID NO: 14 or a partial sequence thereof, or a complementary sequence thereof;

(2) a sequence having an identity of at least 75%, at least 80%, at least 85%, at least 90%, at least 95%, at least 98% or at least 99% to any one of the sequences as defined in (1); or (3) a nucleic acid sequence capable of hybridizing to the sequence as shown in (1) or (2) under a stringent condition.

In another aspect, the present invention provides an editing method for knocking up the expression of an endogenous PPO (PPOX) gene in a plant, which comprises fusing the coding region of the PPO gene with a strong plant endogenous promoter in vivo to form a new highly-expressing plant endogenous PPO gene. That is, simultaneously generating DNA breaks at specific sites between the promoter and the CDS of each of the PPO gene and an optional highly-expressing endogenous gene, ligating the DNA breaks to each other through an intracellular repair pathway to form an in vivo fusion of the coding region of the PPO gene and the optional strong endogenous promoter, thereby creating a new highly-expressing PPO gene. In rice, the strong promoter is preferably a promoter of the CP12 gene. In *Arabidopsis thaliana*, the strong promoter is preferably a promoter of the ubiquitin10 gene.

The present invention also provides a highly-expressing plant endogenous PPO gene obtainable by the above editing method.

The present invention also provides a highly-expressing rice endogenous PPO gene having a sequence selected from the group consisting of:

(1) the nucleic acid sequence as shown in SEQ ID NO: 15, SEQ ID NO: 16, SEQ ID NO: 17, SEQ ID NO: 20, SEQ ID NO: 21, SEQ ID NO: 22, SEQ ID NO: 23, SEQ ID NO: 24, SEQ ID NO: 25, or SEQ ID NO: 26 or a partial sequence thereof, or a complementary sequence thereof;

(2) a sequence having an identity of at least 75%, at least 80%, at least 85%, at least 90%, at least 95%, at least 98% or at least 99% to any one of the sequences as defined in (1); or (3) a nucleic acid sequence capable of hybridizing to the sequence as shown in (1) or (2) under a stringent condition.

The present invention also provides a DNA containing the HPPD, EPSPS or PPO gene.

The present invention also provides a protein encoded by the HPPD, EPSPS or PPO gene or a biologically active fragment thereof.

The present invention also provides a recombinant expression vector, which comprises the HPPD, EPSPS or PPO gene, and a promoter operably linked thereto.

The present invention further provides an expression cassette comprising the HPPD, EPSPS or PPO gene.

The present invention further provides a plant host cell, which comprises the expression cassette.

The present invention further provides a plant regenerated from the plant host cell.

The present invention also provides a method for producing a plant with an increased resistance or tolerance to an herbicide, which comprises regenerating the plant host cell into a plant and/or progeny thereof.

In a specific embodiment, the plant with increased herbicide resistance or tolerance is a non-transgenic line obtainable by crossing a plant regenerated from the plant host cell of the invention with a wild-type plant to remove the exogenous transgenic component through genetic segregation.

The present invention also provides a herbicide-resistant rice, which comprises any of the above-mentioned highly-expressing rice endogenous HPPD gene, highly-expressing rice endogenous EPSPS gene, highly-expressing rice endogenous PPO gene or any combination thereof.

In a specific embodiment, the herbicide-resistant rice is non-transgenic.

The present invention further provides use of the highly-expressing plant endogenous HPPD, EPSPS or PPO gene in improving the resistance or tolerance to an inhibitory herbicide in a plant cell, a plant tissue, a plant part or a plant.

In another aspect, the present invention provides a method for controlling a weed in a plant cultivation site, wherein the plant comprises the above-mentioned plant or a plant prepared by the above-mentioned method, which comprises applying to the cultivation site one or more HPPD, EPSPS or PPO inhibitory herbicides in an amount for effectively controlling the weed.

In the research work of the inventors, it was found that in cells simultaneously undergoing dual-target or multi-target gene editing, a certain proportion of the ends of DNA double-strand breaks at different targets were spontaneously ligated to each other, resulting in events of deletion, inversion or duplication-doubling of the fragments between the targets on the same chromosome, and/or the exchange of chromosome fragments between targets on different chromosomes. It has been reported in the literature that this phenomenon commonly exists in plants and animals (Puchta et al. 2020. Changing local recombination patterns in *Arabidopsis* by CRISPR/Cas mediated chromosome engineering. Nat Commun. DOI: 10.1038/s41467-020-18277-z; Li et al. 2015. Efficient inversions and duplications of mammalian regulatory DNA elements and gene clusters by CRISPR/Cas9. J Mol Cell Biol. DOI: 10.1093/jmcb/mjv016).

The present inventors surprisingly discovered that, by inducing DNA double-strand breaks in a combination of gene editing targets near specific elements of a gene of interest, causing spontaneous repair ligation, directed combination of different gene elements can be achieved at the genome level without the need to provide a foreign DNA template, it is possible to produce therefrom a new functional gene. This strategy greatly accelerates the creation of new genes and has great potential in animal and plant breeding and gene function research.

DETAILED DESCRIPTION OF INVENTION

In the present invention, unless otherwise specified, the scientific and technical terms used herein have the meanings commonly understood by those skilled in the art. In addition, protein and nucleic acid chemistry, molecular biology, cell and tissue culture, microbiology, immunology related terms and laboratory procedures used herein are all terms and routine procedures widely used in the corresponding fields. For example, the standard recombinant DNA and molecular cloning techniques used in the present invention are well known to those skilled in the art and are fully described in the following documents: Sambrook, J., Fritsch, E F and Maniatis, T., Molecular Cloning: A Laboratory Manual; Cold Spring Harbor Laboratory Press: Cold Spring Harbor, 1989. For a better understanding of the present invention, definitions and explanations of related terms are provided below.

The term "genome" as used herein refers to all complements of genetic material (genes and non-coding sequences) present in each cell or virus or organelle of an organism, and/or complete genome inherited from a parent as a unit (haploid).

The term "gene editing" refers to strategies and techniques for targeted specific modification of any genetic information or genome of living organisms. Therefore, the term includes editing of gene coding regions, but also includes editing of regions other than gene coding regions of the genome. It also includes editing or modifying other genetic information of nuclei (if present) and cells.

The term "CRISPR/Cas nuclease" may be a CRISPR-based nuclease or a nucleic acid sequence encoding the same, including but not limited to: 1) Cas9, including SpCas9, ScCas9, SaCas9, xCas9, VRER-Cas9, EQR-Cas9, SpG-Cas9, SpRY-Cas9, SpCas9-NG, NG-Cas9, NGA-Cas9 (VQR), etc.; 2) Cas12, including LbCpf1, FnCpf1, AsCpf1, MAD7, etc., or any variant or derivative of the aforementioned CRISPR-based nuclease; preferably, wherein the at least one CRISPR-based nuclease comprises a mutation compared to the corresponding wild-type sequence, so that the obtained CRISPR-based nuclease recognizes a different PAM sequence. As used herein, "CRISPR-based nuclease" is any nuclease that has been identified in a naturally occurring CRISPR system, which is subsequently isolated from its natural background, and has preferably been modified or combined into a recombinant construct of interest, suitable as a tool for targeted genome engineering. As long as the original wild-type CRISPR-based nuclease provides DNA recognition, i.e., binding properties, any CRISPR-based nuclease can be used and optionally reprogrammed or otherwise mutated so as to be suitable for various embodiments of the invention.

The term "CRISPR" refers to a sequence-specific genetic manipulation technique that relies on clustered regularly interspaced short palindromic repeats, which is different from RNA interference that regulates gene expression at the transcriptional level.

"Cas9 nuclease" and "Cas9" are used interchangeably herein, and refer to RNA-guided nuclease comprising Cas9 protein or fragment thereof (for example, a protein containing the active DNA cleavage domain of Cas9 and/or the gRNA binding domain of Cas9). Cas9 is a component of the CRISPR/Cas (clustered regularly interspaced short palindrome repeats and associated systems) genome editing system. It can target and cut DNA target sequences under the guidance of guide RNA to form DNA double-strand breaks (DSB).

"Cas protein" or "Cas polypeptide" refers to a polypeptide encoded by Cas (CRISPR-associated) gene. Cas protein includes Cas endonuclease. Cas protein can be a bacterial or archaeal protein. For example, the types I to III CRISPR Cas proteins herein generally originate from prokaryotes; the type I and type III Cas proteins can be derived from bacteria or archaea species, and the type II Cas protein (i.e., Cas9) can be derived from bacterial species. "Cas proteins" include Cas9 protein, Cpf1 protein, C2c1 protein, C2c2 protein, C2c3 protein, Cas3, Cas3-HD, Cas5, Cas7, Cas8, Cas10, Cas12a, Cas12b, or a combination or complex thereof.

"Cas9 variant" or "Cas9 endonuclease variant" refers to a variant of the parent Cas9 endonuclease, wherein when associated with crRNA and tracRNA or with sgRNA, the Cas9 endonuclease variant retains the abilities of recognizing, binding to all or part of a DNA target sequence and optionally unwinding all or part of a DNA target sequence, nicking all or part of a DNA target sequence, or cutting all or part of a DNA target sequence. The Cas9 endonuclease variants include the Cas9 endonuclease variants described herein, wherein the Cas9 endonuclease variants are different from the parent Cas9 endonuclease in the following manner: the Cas9 endonuclease variants (when complexed with gRNA to form a polynucleotide-directed endonuclease complex capable of modifying a target site) have at least one improved property, such as, but not limited to, increased transformation efficiency, increased DNA editing efficiency, decreased off-target cutting, or any combination thereof, as compared to the parent Cas9 endonuclease (complexed with the same gRNA to form a polynucleotide-guided endonuclease complex capable of modifying the same target site).

The Cas9 endonuclease variants described herein include variants that can bind to and nick double-stranded DNA target sites when associated with crRNA and tracrRNA or with sgRNA, while the parent Cas endonuclease can bind to the target site and result in double strand break (cleavage) when associated with crRNA and tracrRNA or with sgRNA.

"Guide RNA" and "gRNA" are used interchangeably herein, and refer to a guide RNA sequence used to target a specific gene for correction using CRISPR technology, which usually consists of crRNA and tracrRNA molecules that are partially complementary to form a complex, wherein crRNA contains a sequence that has sufficient complementarity with the target sequence so to hybridize with the target sequence and direct the CRISPR complex (Cas9+crRNA+tracrRNA) to specifically bind to the target sequence. However, it is known in the art that a single guide RNA (sgRNA) can be designed, which contains both the properties of crRNA and tracrRNA.

The terms "single guide RNA" and "sgRNA" are used interchangeably herein, and refer to the synthetic fusion of two RNA molecules, which comprises a fusion of a crRNA (CRISPR RNA) of a variable targeting domain (linked to a tracr pairing sequence hybridized to tracrRNA) and a tracrRNA (trans-activating CRISPR RNA). The sgRNA may comprise crRNA or crRNA fragments and tracrRNA or tracrRNA fragments of the type II CRISPR/Cas system that can form a complex with the type II Cas endonuclease, wherein the guide RNA/Cas endonuclease complex can guide the Cas endonuclease to a DNA target site so that the Cas endonuclease can recognize, optionally bind to the DNA target site, and optionally nick the DNA target site or cut (introduce a single-strand or double-strand break) the DNA target site.

In certain embodiments, the guide RNA(s) and Cas9 can be delivered to a cell as a ribonucleoprotein (RNP) complex. RNP is composed of purified Cas9 protein complexed with gRNA, and it is well known in the art that RNP can be effectively delivered to many types of cells, including but not limited to stem cells and immune cells (Addgene, Cambridge, MA, Mirus Bio LLC, Madison, WI).

The protospacer adjacent motif (PAM) herein refers to a short nucleotide sequence adjacent to a (targeted) target sequence (prespacer) recognized by the gRNA/Cas endonuclease system. If the target DNA sequence is not adjacent to an appropriate PAM sequence, the Cas endonuclease may not be able to successfully recognize the target DNA sequence. The sequence and length of PAM herein can be different depending on the Cas protein or Cas protein complex in use. The PAM sequence can be of any length, but is typically in length of 1, 2, 3, 4, 5, 6, 7, 8, 9, 10, 11, 12, 13, 14, 15, 16, 17, 18, 19 or 20 nucleotides.

As used herein, the term "organism" includes animals, plants, fungi, bacteria, and the like.

As used herein, the term "host cell" includes plant cells, animal cells, fungal cells, bacterial cells, and the like.

In the present invention, the "plant" should be understood to mean any differentiated multicellular organism capable of performing photosynthesis, in particular monocotyledonous or dicotyledonous plants, for example, (1) food crops: *Oryza* spp., like *Oryza sativa, Oryza latifolia, Oryza sativa, Oryza glaberrima; Triticum* spp., like *Triticum aestivum, T. Turgidum* ssp. durum; *Hordeum* spp., like *Hordeum vulgare, Hordeum arizonicum; Secale cereale; Avena* spp., like *Avena sativa, Avena fatua, Avena byzantine, Avena fatua* var. *sativa, Avena hybrida; Echinochloa* spp., like *Pennisetum glaucum, Sorghum, Sorghum bicolor, Sorghum vulgare, Triticale, Zea mays* or Maize, Millet, Rice, Foxtail millet, Proso millet, *Sorghum bicolor, Panicum, Fagopyrum* spp., *Panicum miliaceum, Setaria italica, Zizania palustris, Eragrostis tef, Panicum miliaceum, Eleusine coracana*; (2) legume crops: *Glycine* spp. like *Glycine max, Soja hispida, Soja max, Vicia* spp., *Vigna* spp., *Pisum* spp., field bean, *Lupinus* spp., *Vicia, Tamarindus indica, Lens culinaris, Lathyrus* spp., *Lablab*, broad bean, mung bean, red bean, chickpea; (3) oil crops: *Arachis hypogaea, Arachis* spp, *Sesamum* spp., *Helianthus* spp. like *Helianthus annuus, Elaeis* like *Eiaeis guineensis, Elaeis oleifera*, soybean, Brassicanapus, *Brassica oleracea, Sesamum orientale, Brassica juncea*, Oilseed rape, *Camellia oleifera*, oil palm, olive, castor-oil plant, *Brassica napus* L., canola; (4) fiber crops: *Agave sisalana, Gossypium* spp. like *Gossypium, Gossypium barbadense, Gossypium hirsutum, Hibiscus cannabinus, Agave sisalana, Musa textilis* Nee, *Linum usitatissimum, Corchorus capsularis* L, *Boehmeria nivea* (L.), *Cannabis sativa, Cannabis sativa*; (5) fruit crops: *Ziziphus* spp., *Cucumis* spp., *Passiflora edulis, Vitis* spp., *Vaccinium* spp., *Pyrus communis, Prunus* spp., *Psidium* spp., *Punica granatum, Malus* spp., *Citrullus lanatus, Citrus* spp., *Ficus carica, Fortunella* spp., *Fragaria* spp., *Crataegus* spp., *Diospyros* spp., *Eugenia unifora, Eriobotrya japonica, Dimocarpus longan, Carica papaya, Cocos* spp., *Averrhoa carambola, Actinidia* spp., *Prunus amygdalus, Musa* spp. (*musa acuminate*), *Persea* spp. (*Persea Americana*), *Psidium guajava, Mammea Americana, Mangifera indica, Canarium album* (Oleaeuropaea), *Caricapapaya, Cocos nucifera, Malpighia emarginata, Manilkara zapota, Ananas comosus, Annona* spp., *Citrus* reticulate (*Citrus* spp.), *Artocarpus* spp., *Litchi chinensis, Ribes* spp., *Rubus* spp., pear, peach, apricot, plum, red bayberry, lemon, kumquat, durian, orange, strawberry, blueberry, hami melon, muskmelon, date palm, walnut tree, cherry tree; (6) rhizome crops: *Manihot* spp., *Ipomoea batatas, Colocasia esculenta*, tuber mustard, *Allium cepa* (onion), *eleocharis* tuberose (water chestnut), *Cyperus rotundus, Rhizoma dioscoreae*; (7) vegetable crops: *Spinacia* spp., *Phaseolus* spp., *Lactuca sativa, Momordica* spp, *Petroselinum crispum, Capsicum* spp., *Solanum* spp. (such as *Solanum tuberosum, Solanum integrifolium, Solanum lycopersicum*), *Lycopersicon* spp. (such as *Lycopersicon esculentum, Lycopersicon lycopersicum, Lycopersicon pyriforme*), *Macrotyloma* spp., Kale, *Luffa acutangula*, lentil, okra, onion, potato, artichoke, *asparagus*, broccoli, Brussels sprouts, cabbage, carrot, cauliflower, celery, collard greens, squash, *Benincasa hispida, Asparagus officinalis, Apium graveolens, Amaranthus* spp., *Allium* spp., *Abelmoschus* spp., *Cichorium endivia, Cucurbita* spp., *Coriandrum sativum, B. carinata, Rapbanus sativus, Brassica* spp. (such as *Brassica napus, Brassica rapa* ssp., canola, oilseed rape, turnip rape, turnip rape, leaf mustard, cabbage, black mustard, canola (rapeseed), Brussels sprout, Solanaceae (eggplant), *Capsicum annuum* (sweet pepper), cucumber, *luffa*, Chinese cabbage, rape, cabbage, calabash, Chinese chives, lotus, lotus root, lettuce; (8) flower crops: *Tropaeolum minus, Tropaeolum majus, Canna indica, Opuntia* spp., *Tagetes* spp., *Cymbidium* (orchid), *Crinum asiaticum* L., *Clivia, Hippeastrum* rutilum, *Rosa rugosa, Rosa Chinensis, Jasminum sambac, Tulipa gesneriana* L., *Cerasus* sp., *Pharbitis nil* (L.) *Choisy, Calendula officinalis* L., *Nelumbo* sp., *Bellis perennis* L., *Dianthus caryophyllus, Petunia hybrida, Tulipa gesneriana* L., *Lilium brownie, Prunus mume, Narcissus tazetta* L., *Jasminum nudiflorum Lindl., Primula malacoides, Daphne odora, Camellia japonica, Michelia alba, Magnolia liliiflora, Viburnum macrocephalum, Clivia miniata, Malus spectabilis, Paeonia suffruticosa, Paeonia lactiflora, Syzygium aromaticum, Rhododendron simsii, Rhododendron hybridum, Michelia figo* (Lour.) Spreng., *Cercis chinensis, Kerria japonica, Weigela florida, Fructus forsythiae, Jasminum mesnyi, Parochetus communis, Cyclamen persicum* Mill., Phalaenopsis hybrid, *Dendrobium nobile, Hyacinthus orientalis, Iris tectorum Maxim, Zantedeschia aethiopica, Calendula officinalis, Hippeastrum*

*rutilum, Begonia semperflorenshybr, Fuchsia hybrida, Begonia maculataRaddi, Geranium, Epipremnum aureum*; (9) medicinal crops: *Carthamus tinctorius, Mentha* spp., *Rheum rhabarbarum, Crocus sativus, Lycium chinense, Polygonatum odoratum, Polygonatum Kingianum, Anemarrhena asphodeloides Bunge, Radix ophiopogonis, Fritillaria cirrhosa, Curcuma aromatica, Amomum villosum* Lour., *Polygonum multiflorum, Rheum officinale, Glycyrrhiza uralensis* Fisch, *Astragalus membranaceus, Panax ginseng, Panax notoginseng, Acanthopanax gracilistylus, Angelica sinensis, Ligusticum wallichii, Bupleurum sinenses* DC., *Datura stramonium* Linn., *Datura metel* L., *Mentha haplocalyx, Leonurus sibiricus* L., *Agastache rugosus, Scutellaria baicalensis, Prunella vulgaris* L., *Pyrethrum carneum, Ginkgo biloba* L., *Cinchona ledgeriana, Hevea brasiliensis* (wild), *Medicago sativa* Linn, *Piper Nigrum* L., *Radix Isatidis, Atractylodes macrocephala* Koidz; (10) raw material crops: *Hevea brasiliensis, Ricinus communis, Vernicia fordii, Morus alba* L., *Hops Humulus lupulus, Betula, Alnus cremastogyne* Burk., *Rhus verniciflua* stokes; (11) pasture crops: *Agropyron* spp., *Trifolium* spp., *Miscanthus sinensis, Pennisetum* sp., *Phalaris arundinacea, Panicum virgatum*, prairiegrasses, Indiangrass, Big bluestem grass, *Phleum pratense*, turf, cyperaceae (*Kobresia pygmaea, Carex pediformis, Carex humilis*), *Medicago sativa* Linn, *Phleum pratense* L., *Medicago sativa, Melilotus suavcolen, Astragalus sinicus, Crotalaria juncea, Sesbania cannabina, Azolla imbircata, Eichhornia crassipes, Amorpha fruticosa, Lupinus micranthus, Trifolium, Astragalus adsurgens pall, Pistia stratiotes* linn, *Alternanthera philoxeroides, Lolium*; (12) sugar crops: *Saccharum* spp., *Beta vulgaris*; (13) beverage crops: *Camellia sinensis, Camellia Sinensis*, tea, Coffee (*Coffea* spp.), *Theobroma cacao, Humulus lupulus* Linn.; (14) lawn plants: *Ammophila arenaria, Poa* spp. (*Poa pratensis* (bluegrass)), *Agrostis* spp. (*Agrostis matsumurae, Agrostis palustris*), *Lolium* spp. (*Lolium*), *Festuca* spp. (*Festuca ovina* L.), *Zoysia* spp. (Zoysiajaponica), *Cynodon* spp. (*Cynodon dactylon*/bermudagrass), *Stenotaphrum secunda tum* (*Stenotaphrum secundatum*), *Paspalum* spp., *Eremochloa ophiuroides* (centipedegrass), *Axonopus* spp. (carpetweed), *Bouteloua dactyloides* (buffalograss), *Bouteloua* var. spp. (*Bouteloua gracilis*), *Digitaria sanguinalis, Cyperusrotundus, Kyllingabrevifolia, Cyperusamuricus, Erigeron canadensis, Hydrocotylesibthorpioides, Kummerowiastriata, Euphorbia humifusa, Viola arvensis, Carex rigescens, Carex heterostachya*, turf; (15) tree crops: *Pinus* spp., *Salix* spp., *Acer* spp., *Hibiscus* spp., *Eucalyptus* spp., *Ginkgo biloba, Bambusa* sp., *Populus* spp., *Prosopis* spp., *Quercus* spp., *Phoenix* spp., *Fagus* spp., *Ceiba pentandra, Cinnamomum* spp., *Corchorus* spp., *Phragmites australis, Physalis* spp., *Desmodium* spp., *Populus, Hedera helix, Populus tomentosa* Carr, *Viburnum odoratissinum, Ginkgo biloba* L., *Quercus, Ailanthus altissima, Schima superba, Ilex* purpurea, *Platanus acerifolia, ligustrum lucidum, Buxus megistophylla* Levl., *Dahurian larch, Acacia mearnsii, Pinus massoniana, Pinus khasys, Pinus yunnanensis, Pinus finlaysoniana, Pinus tabuliformis, Pinus koraiensis, Juglans nigra, Citrus limon, Platanus acerifolia, Syzygium jambos, Davidia involucrate, Bombax malabarica* L., *Ceiba pentandra* (L.), *Bauhinia blakeana, Albizia saman, Albizzia julibrissin, Erythrina corallodendron, Erythrina indica, Magnolia gradiflora, Cycas revolute, Lagerstroemia indica*, coniferous, macrophanerophytes, Frutex; (16) nut crops: *Bertholletia excelsea, Castanea* spp., *Corylus* spp., *Carya* spp., *Juglans* spp., *Pistacia vera, Anacardium occidentale, Macadamia* (*Macadamia integrifolia*), *Carya illinoensis* Koch, *Macadamia*, Pistachio, Badam, other plants that produce nuts; (17) others: *Arabidopsis thaliana, Brachiaria eruciformis, Cenchrus echinatus, Setaria faberi, Eleusine indica, Cadaba farinose, algae, Carex elata*, ornamental plants, *Carissa macrocarpa, Cynara* spp., *Daucus carota, Dioscorea* spp., *Erianthus* sp., *Festuca arundinacea, Hemerocallis fulva, Lotus* spp., *Luzula sylvatica, Medicago sativa, Melilotus* spp., *Morus nigra, Nicotiana* spp., *Olea* spp., *Ornithopus* spp., *Pastinaca sativa, Sambucus* spp., *Sinapis* sp., *Syzygium* spp., *Tripsacum dactyloides, Triticosecale rimpaui, Viola odorata*, and the like.

In a specific embodiment, the plant is selected from rice, corn, wheat, soybean, sunflower, *sorghum*, rape, alfalfa, cotton, barley, millet, sugarcane, tomato, tobacco, cassava, potato, sweet potato, Chinese cabbage, cabbage, cucumber, Chinese rose, *Scindapsus aureus*, watermelon, melon, strawberry, blueberry, grape, apple, *citrus*, peach, pear, banana, etc.

As used herein, the term "plant" includes a whole plant and any progeny, cell, tissue or part of plant. The term "plant part" includes any part of a plant, including, for example, but not limited to: seed (including mature seed, immature embryo without seed coat, and immature seed); plant cutting; plant cell; plant cell culture; plant organ (e.g., pollen, embryo, flower, fruit, bud, leaf, root, stem, and related explant). Plant tissue or plant organ can be seed, callus tissue, or any other plant cell population organized into a structural or functional unit. Some plant cells or tissue cultures can regenerate a plant that has the physiological and morphological characteristics of the plant from which the cell or tissue is derived, and can regenerate a plant that has substantially the same genotype as the plant. In contrast, some plant cells cannot regenerate plants. The regenerable cells in plant cells or tissue cultures can be embryos, protoplasts, meristematic cells, callus, pollen, leaves, anthers, roots, root tips, silks, flowers, kernels, ears, cobs, husks, or stems.

The plant parts comprise harvestable parts and parts that can be used to propagate offspring plants. The plant parts that can be used for propagation include, for example, but not limited to: seeds; fruits; cuttings; seedlings; tubers; and rootstocks. The harvestable parts of plants can be any of useful parts of plants, including, for example, but not limited to: flowers; pollen; seedlings; tubers; leaves; stems; fruits; seeds; and roots.

The plant cells are the structural and physiological units of plants. As used herein, the plant cells include protoplasts and protoplasts with partial cell walls. The plant cells may be in a form of isolated single cells or cell aggregates (e.g., loose callus and cultured cells), and may be part of higher order tissue units (e.g., plant tissues, plant organs, and intact plants). Therefore, the plant cells can be protoplasts, gamete-producing cells, or cells or collection of cells capable of regenerating a whole plant. Therefore, in the embodiments herein, a seed containing a plurality of plant cells and capable of regenerating into a whole plant is considered as a "plant part".

As used herein, the term "protoplast" refers to a plant cell whose cell wall is completely or partially removed and whose lipid bilayer membrane is exposed. Typically, the protoplast is an isolated plant cell without cell wall, which has the potential to regenerate a cell culture or a whole plant.

The plant "offspring" includes any subsequent generations of the plant.

The terms "inhibitory herbicide tolerance" and "inhibitory herbicide resistance" can be used interchangeably, and both refer to tolerance and resistance to an inhibitory herbicide. "Improvement in tolerance to inhibitory herbicide"

and "improvement in resistance to inhibitory herbicide" mean that the tolerance or resistance to the inhibitory herbicide is improved as compared to a plant containing the wild-type gene.

The term "wild-type" refers to a nucleic acid molecule or protein that can be found in nature.

In the present invention, the term "cultivation site" comprises a site where the plant of the present invention is cultivated, such as soil, and also comprises, for example, plant seeds, plant seedlings and grown plants. The term "weed-controlling effective amount" refers to an amount of herbicide that is sufficient to affect the growth or development of the target weed, for example, to prevent or inhibit the growth or development of the target weed, or to kill the weed. Advantageously, the weed-controlling effective amount does not significantly affect the growth and/or development of the plant seeds, plant seedlings or plants of the present invention. Those skilled in the art can determine such weed-controlling effective amount through routine experiments.

The term "gene" comprises a nucleic acid fragment expressing a functional molecule (such as, but not limited to, specific protein), including regulatory sequences before (5' non-coding sequences) and after (3' non-coding sequences) a coding sequence.

The DNA sequence that "encodes" a specific RNA is a DNA nucleic acid sequence that can be transcribed into RNA. The DNA polynucleotides can encode a RNA (mRNA) that can be translated into a protein, or the DNA polynucleotides can encode a RNA that cannot be translated into a protein (for example, tRNA, rRNA, or DNA-targeting RNA; which are also known as "non-coding" RNA or "ncRNA").

The terms "polypeptide", "peptide" and "protein" are used interchangeably in the present invention, and refer to a polymer of amino acid residues. The terms are applied to amino acid polymers in which one or more amino acid residues are artificially chemical analogs of corresponding and naturally occurring amino acids, as well as to naturally occurring amino acid polymers. The terms "polypeptide", "peptide", "amino acid sequence" and "protein" may also include their modification forms, including but not limited to glycosylation, lipid linkage, sulfation, γ-carboxylation of glutamic acid residue, hydroxylation and ADP-ribosylation.

The term "biologically active fragment" refers to a fragment that has one or more amino acid residues deleted from the N and/or C-terminus of a protein while still retaining its functional activity.

The terms "polynucleotide" and "nucleic acid" are used interchangeably and comprise DNA, RNA or hybrids thereof, which may be double-stranded or single-stranded.

The terms "nucleotide sequence" and "nucleic acid sequence" both refer to the sequence of bases in DNA or RNA.

Those of ordinary skill in the art can easily use known methods, such as directed evolution and point mutation methods, to mutate the DNA fragments as shown in SEQ ID No. 9 to SEQ ID No. 17 of the present invention. Those artificially modified nucleotide sequences that have at least 75% identity to any one of the foregoing sequences of the present invention and exhibit the same function are considered as derivatives of the nucleotide sequence of the present invention and equivalent to the sequences of the present invention.

The term "identity" refers to the sequence similarity to a natural nucleic acid sequence. Sequence identity can be evaluated by observation or computer software. Using a computer sequence alignment software, the identity between two or more sequences can be expressed as a percentage (%), which can be used to evaluate the identity between related sequences. "Partial sequence" means at least 5%, 10%, 20%, 30%, 40%, 50%, 60%, 70%, 80%, 90% or 95% of a given sequence.

The stringent condition may be as follows: hybridizing at 50° C. in a mixed solution of 7% sodium dodecyl sulfate (SDS), 0.5M $NaPO_4$, and 1 mM EDTA, and washing at 50° C. in 2×SSC and 0.1% SDS; or alternatively: hybridizing at 50° C. in a mixed solution of 7% SDS, 0.5M $NaPO_4$ and 1 mM EDTA, and washing at 50° C. in 1×SSC and 0.1% SDS; or alternatively: hybridizing at 50° C. in a mixed solution of 7% SDS, 0.5M $NaPO_4$ and 1 mM EDTA, and washing at 50° C. in 0.5×SSC and 0.1% SDS; or alternatively: hybridizing at 50° C. in a mixed solution of 7% SDS, 0.5M $NaPO_4$ and 1 mM EDTA, and washing at 50° C. in 0.1×SSC and 0.1% SDS; or alternatively: hybridizing at 50° C. in a mixed solution of 7% SDS, 0.5M $NaPO_4$ and 1 mM EDTA, and washing at 65° C. in 0.1×SSC and 0.1% SDS; or alternatively: hybridizing at 65° C. in a solution of 6×SSC, 0.5% SDS, and then membrane washing with 2×SSC, 0.1% SDS and 1×SSC, 0.1% SDS each once; or alternatively: hybridizing and membrane washing twice in a solution of 2×SSC, 0.1% SDS at 68° C., 5 min each time, and then hybridizing and membrane washing twice in a solution of 0.5×SSC, 0.1% SDS at 68° C., 15 min each time; or alternatively: hybridizing and membrane washing in a solution of 0.1× SSPE (or 0.1×SSC), 0.1% SDS at 65° C.

As used in the present invention, "expression cassette", "expression vector" and "expression construct" refer to a vector such as a recombinant vector suitable for expression of a nucleotide sequence of interest in a plant. The term "expression" refers to the production of a functional product. For example, the expression of a nucleotide sequence may refer to the transcription of the nucleotide sequence (such as transcription to generate mRNA or functional RNA) and/or the translation of RNA into a precursor or mature protein.

The "expression construct" of the present invention can be a linear nucleic acid fragment, a circular plasmid, a viral vector, or, in some embodiments, can be an RNA (such as mRNA) that can be translated.

The "expression construct" of the present invention may comprise regulatory sequences and nucleotide sequences of interest from different sources, or regulatory sequences and nucleotide sequences of interest from the same source but arranged in a way different from those normally occurring in nature.

The "highly-expressing gene" in the present invention refers to a gene whose expression level is higher than that of a common gene in a specific tissue.

The terms "recombinant expression vector" or "DNA construct" are used interchangeably herein and refer to a DNA molecule comprising a vector and at least one insert. Recombinant expression vectors are usually produced for the purpose of expression and/or propagation of the insert or for the construction of other recombinant nucleotide sequences. The insert may be operably or may be inoperably linked to a promoter sequence and may be operably or may be inoperably linked to a DNA regulatory sequence.

The terms "regulatory sequence" and "regulatory element" can be used interchangeably and refer to a nucleotide sequence that is located at the upstream (5' non-coding sequence), middle or downstream (3' non-coding sequence) of a coding sequence, and affects the transcription, RNA processing, stability or translation of a related coding sequence. Plant expression regulatory elements refer to nucleotide sequences that can control the transcription, RNA processing or stability or translation of a nucleotide sequence of interest in plants.

The regulatory sequences may include, but are not limited to, promoters, translation leader sequences, introns, and poly A recognition sequences.

The term "promoter" refers to a nucleic acid fragment capable of controlling the transcription of another nucleic acid fragment. In some embodiments of the present invention, the promoter is a promoter capable of controlling gene transcription in plant cells, regardless of whether it is derived from plant cells. The promoter can be a constitutive promoter or a tissue-specific promoter or a developmentally regulated promoter or an inducible promoter.

The term "strong promoter" is a well-known and widely used term in the art. Many strong promoters are known in the art or can be identified by routine experiments. The activity of the strong promoter is higher than the activity of the promoter operatively linked to the nucleic acid molecule to be overexpressed in a wild-type organism, for example, a promoter with an activity higher than the promoter of an endogenous gene. Preferably, the activity of the strong promoter is higher by about 2%, 5%, 8%, 10%, 20%, 30%, 40%, 50%, 60%, 70%, 80%, 90%, 100%, 150%, 200%, 250%, 300%, 350%, 400%, 450%, 500%, 600%, 700%, 800%, 900%, 1000% or more than 1000% than the activity of the promoter operably linked to the nucleic acid molecule to be overexpressed in the wild-type organism. Those skilled in the art know how to measure the activity of a promoter and compare the activities of different promoters.

The term "constitutive promoter" refers to a promoter that will generally cause gene expression in most cell types in most cases. "Tissue-specific promoter" and "tissue-preferred promoter" are used interchangeably, and refer to a promoter that is mainly but not necessarily exclusively expressed in a tissue or organ, and also expressed in a specific cell or cell type. "Developmentally regulated promoter" refers to a promoter whose activity is determined by a developmental event. "Inducible promoter" responds to an endogenous or exogenous stimulus (environment, hormone, chemical signal, etc.) to selectively express an operably linked DNA sequence.

As used herein, the term "operably linked" refers to a connection of a regulatory element (for example, but not limited to, promoter sequence, transcription termination sequence, etc.) to a nucleic acid sequence (for example, a coding sequence or open reading frame) such that the transcription of the nucleotide sequence is controlled and regulated by the transcription regulatory element. The techniques for operably linking regulatory element region to nucleic acid molecule are known in the art.

The "introducing" a nucleic acid molecule (such as a plasmid, linear nucleic acid fragment, RNA, etc.) or protein into a plant refers to transforming a cell of the plant with the nucleic acid or protein so that the nucleic acid or protein can function in the plant cell. The term "transformation" used in the present invention comprises stable transformation and transient transformation.

The term "stable transformation" refers to that the introduction of an exogenous nucleotide sequence into a plant genome results in a stable inheritance of the exogenous gene. Once stably transformed, the exogenous nucleic acid sequence is stably integrated into the genome of the plant and any successive generations thereof.

The term "transient transformation" refers to that the introduction of a nucleic acid molecule or protein into a plant cell to perform function does not result in a stable inheritance of the foreign gene. In transient transformation, the exogenous nucleic acid sequence is not integrated into the genome of the plant.

Changing the expression of endogenous genes in organisms includes two aspects: intensity and spatial-temporal characteristics. The change of intensity includes the increase (knock-up), decrease (knock-down) and/or shut off the expression of the gene (knock-out); the spatial-temporal specificity includes temporal (growth and development stage) specificity and spatial (tissue) specificity, as well as inducibility. In addition, it includes changing the targeting of a protein, for example, changing the feature of cytoplasmic localization of a protein into a feature of chloroplast localization or nuclear localization.

Unless otherwise defined, all technical and scientific terms used herein have the same meanings as commonly understood by those of ordinary skill in the art to which the present invention pertains. Although any methods and materials similar or equivalent to those described herein can also be used in the practice or testing of the present invention, the preferred methods and materials are now described.

All publications and patents cited in this description are incorporated herein by reference as if each individual publication or patent is exactly and individually indicated to be incorporated by reference, and is incorporated herein by reference to disclose and describe methods and/or materials related to the publications cited. The citation of any publication which it was published before the filing date should not be interpreted as an admission that the present invention is not eligible to precede the publication of the existing invention. In addition, the publication date provided may be different from the actual publication date, which may require independent verification.

Unless specifically stated or implied, as used herein, the terms "a", "a/an" and "the" mean "at least one." All patents, patent applications, and publications mentioned or cited herein are incorporated herein by reference in their entirety, with the same degree of citation as if they were individually cited.

The present invention has the following advantageous technical effects:

The present invention comprehensively uses the information of the following two different professional fields to develop a method for directly creating new genes in organisms, completely changing the conventional use of the original gene editing tools (i.e., knocking out genes), realizing a new use thereof for creating new genes, in particular, realizing an editing method for knocking up endogenous genes by using gene editing technology to increase the expression of target genes. The first is the information in the field of gene editing, that is, when two or more different target sites and Cas9 simultaneously target the genome or organism, different situations such as deletion, inversion, doubling or inversion-doubling may occur. The second is the information in the field of genomics, that is, the information about location and distance of different genes in the genome, and specific locations, directions and functions of different elements (promoter, 5'UTR, coding region (CDS), different domain regions, terminator, etc.) in genes, and expression specificity of different genes, etc. By combining the information in these two different fields, breaks are induced at specific sites of two or more different genes or at two or more specific sites within a single gene (specific sites can be determined in the field of genomics), a new combination of different gene elements or functional domains can be formed through deletion, inversion, doubling, and inversion-doubling or chromosome arm exchange, etc. (the specific situations would be provided in the field of gene editing), thereby specifically creating a new gene in the organism.

The new genes created by the present invention are formed by the fusion or recombination of different elements of two or more genes under the action of the spontaneous DNA repair mechanism in the organism to change the expression intensity, spatial-temporal specificity, special functional domains and the like of the original gene without an exogenous transgene or synthetic gene elements. Because the new gene has the fusion of two or more different gene elements, this greatly expands the scope of gene mutation, and will produce more abundant and diverse functions, thus it has a wide range of application prospects. At the same time, these new genes are not linked to the gene editing vectors, so the vector elements can be removed through genetic segregation, and thereby resulting in non-transgenic biological materials containing the new genes for animal and plant breeding. Alternatively, non-integrated transient editing can be performed by delivery of mRNA or ribonucleic acid protein complex (RNP) to create non-genetically modified biological materials containing the new genes. This process is non-transgenic and the resultant edited materials would contain no transgene as well. In theory and in fact, these new genes can also be obtained through traditional breeding techniques (such as radiation or chemical mutagenesis). The difference is that the screening with traditional techniques requires the creation of libraries containing a huge number of random mutants and thus it is time-consuming and costly to screen new functional genes. While in the present invention, new functional genes can be created through bioinformatics analysis combined with gene editing technology, the breeding duration can be greatly shortened. The method of the present invention is not obliged to the current regulations on gene editing organisms in many countries.

In addition, the new gene creation technology of the present invention can be used to change many traits in organisms, including the growth, development, resistance, yield, etc., and has great application value. The new genes created may have new regulatory elements (such as promoters), which will change the expression intensity and and/or spatial-temporal characteristics of the original genes, or will have new amino acid sequences and thus have new functions. Taking crops as an example, changing the expression of specific genes can increase the resistance of crops to noxious organisms such as pests and weeds and abiotic stresses such as drought, waterlogging, and salinity, and can also increase yield and improve quality. Taking fish as an example, changing the expression characteristics of growth hormone in fish can significantly change its growth and development speed.

BRIEF DESCRIPTION OF DRAWINGS

FIG. 1 shows a schematic diagram of creating a new HPPD gene in rice. HPPD is SEQ ID No: 6. UBI2 is SEQ ID NO: 5.

FIG. 5 shows the sequencing results for the HPPD-duplication Scheme tested with rice protoplast. The sequence in FIG. 5 (1) is SEQ ID NO: 9. The sequence in FIG. 5 (2) is SEQ ID NO: 10.

FIG. 15 shows the sequencing results of the EPSPS-inversion detection. The sequence in FIG. 15(1) is SEQ ID NO: 11. The sequence in FIG. 15(2) is SEQ ID NO: 12. The sequence in FIG. 15(3) is SEQ ID NO: 13. The sequence in FIG. 15(4) is SEQ ID NO: 14.

SPECIFIC MODELS FOR CARRYING OUT THE INVENTION

Figure 2:
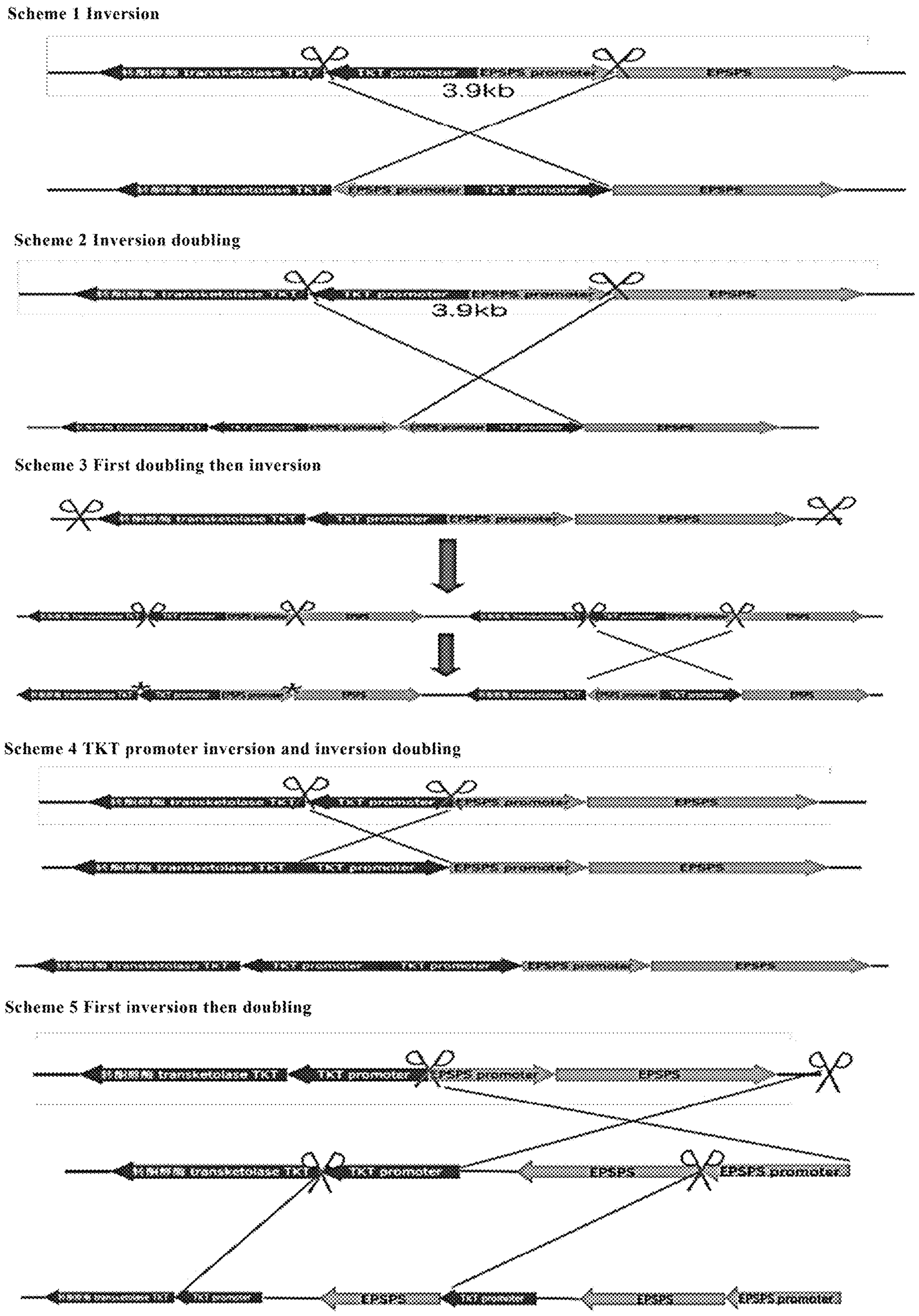
FIG. 2 shows a schematic diagram of creating a new EPSPS gene in rice. EPSPS is SEQ ID NO: 4. TKT is SEQ ID NO: 3.

The present invention is further described in conjunction with the examples as follows. The following description is just illustrative, and the protection scope of the present invention should not be limited to this.

Example 1: An Editing Method for Knocking Up the Expression of the Endogenous HPPD Gene by Inducing Doubling of Chromosome Fragment in Plant—Rice Protoplast Test HPPD was a key enzyme in the pathway of chlorophyll synthesis in plants, and the inhibition of the activity of the HPPD would eventually lead to albino chlorosis and death of plants. Many herbicides, such as mesotrione and topramezone, were inhibitors with the HPPD as the target protein, and thus increasing the expression level of the endogenous HPPD gene in plants could improve the tolerance of the plants to these herbicides. The rice HPPD gene (as shown in SEQ ID NO: 6, in which 1-1067 bp is the promoter, and the rest is the expression region) locates on rice chromosome 2. Through bioinformatic analysis, it was found that rice Ubiquitin2 (hereinafter referred to as UBI2) gene (as shown in SEQ ID NO: 5, in which 1-2107 bp was the promoter, and the rest was the expression region) locates about 338 kb downstream of HPPD gene, and the UBI2 gene and the HPPD gene were in the same direction on the chromosome. According to the rice gene expression profile data provided by the International Rice Genome Sequencing Project, the expression intensity of the UBI2 gene in rice leaves was 3 to 10 times higher than that of the HPPD gene, and the UBI2 gene promoter was a strong constitutively expressed promoter.

As shown in FIG. 1, Scheme 1 shows that double-strand breaks were simultaneously generated at the sites between the promoters and the CDS region of the HPPD and UBI2 genes respectively, the event of doubling the region between the two breaks were obtained after screening and identification, and a new gene could be formed by fusing the promoter of UBI2 and the coding region of HPPD together. In addition, according to Scheme 2 as shown in FIG. 1, a new gene in which the promoter of UBI2 and the coding region of HPPD were fused could also be formed by two consecutive inversions. First, the schemes as shown in FIG. 1 were tested in the rice protoplast system as follows:

1. Firstly, the genomic DNA sequences of the rice HPPD and UBI2 genes were input into the CRISPOR online tool to search for available editing target sites. After online scoring, the following target sites between the promoters and the CDS regions of HPPD and UBI2 genes were selected for testing:

| | | |
|---|---|---|
| OsHPPD-guide RNA1 | SEQ ID NO: 27 | GTGCTGGTTGCCTTGGCTGC |
| OsHPPD-guide RNA2 | SEQ ID NO: 28 | CACAAATTCACCAGCAGCCA |
| OsHPPD-guide RNA3 | SEQ ID NO: 29 | TAAGAACTAGCACAAGATTA |
| OsHPPD-guide RNA4 | SEQ ID NO: 30 | GAAATAATCACCAAACAGAT |

The guide RNA1 and guide RNA2 located between the promoter and the CDS region of the HPPD gene, close to the start codon of the HPPD protein, and the guide RNA3 and guide RNA4 located between the promoter and CDS region of the UBI2 gene, close to the UBI2 protein initiation codon.

pHUE411 vector is used as the backbone, and the following primers were designed for the above-mentioned target sites to perform vector construction as described in "Xing H L, Dong L, Wang Z P, Zhang H Y, Han C Y, Liu B, Wang X C, Chen Q J. A CRISPR/Cas9 Toolkit for multiplex genome editing in plants. BMC Plant Biol. 2014 Nov. 29; 14(1): 327".

| Primer No. | | DNA sequence (5' to 3') |
|---|---|---|
| OsHPPD-sgRNA1-F | SEQ ID NO: 31 | ATATGGTCTCGGGCGGTGCTGGTTGCCTTGGCTGCGTTTTAGAGCTAGAAATAGCAAG |
| OsHPPD-sgRNA2-F | SEQ ID NO: 32 | ATATGGTCTCGGGCGCACAAATTCACCAGCAGCCAGTTTTAGAGCTAGAAATAGCAAG |
| OsHPPD-sgRNA3-R | SEQ ID NO: 33 | TATTGGTCTCTAAACTAATCTTGTGCTAGTTCTTAGCTTCTTGGTGCCGCGC |
| OsHPPD-sgRNA4-R | SEQ ID NO: 34 | TATTGGTCTCTAAACATCTGTTTGGTGATTATTTCGCTTCTTGGTGCCGCGC |

gene editing vectors for the following dual-target combination were constructed following the method provided in the above-mentioned literature. Specifically, with the pCBC-MT1T2 plasmid as the template, sgRNA1+3, sgRNA1+4, sgRNA2+3 and sgRNA2+4 double target fragments were amplified respectively for constructing the sgRNA expression cassettes. The vector backbone of pHUE411 was digested with BsaI, and recovered from the gel, and the target fragment was digested and directly used for the ligation reaction. T4 DNA ligase was used to ligate the vector backbone and the target fragment, and the ligation product was transformed into Trans5a competent cells. Different monoclones were picked and sequenced The Sparkjade High Purity Plasmid Mini Extraction Kit was used to extract plasmids from the clones with correct sequences, thereby obtaining recombinant plasmids, respectively named as pQY002065, pQY002066, pQY002067, and pQY002068, as follows:

pQY002065 pHUE411-HPPD-sgRNA1+3 combination of OsHPPD-guide RNA1, guide RNA3 pQY002066 pHUE411-HPPD-sgRNA1+4 combination of OsHPPD-guide RNA1, guide RNA4 pQY002067 pHUE411-HPPD-sgRNA2+3 combination of OsHPPD-guide RNA2, guide RNA3 pQY002068 pHUE411-HPPD-sgRNA2+4 combination of OsHPPD-guide RNA2, guide RNA4

2. Plasmids of high-purity and high-concentration were prepared for the above-mentioned pQY002065-002068 vectors as follows:

Plasmids were extracted with the Promega Medium Plasmid Extraction Kit (Midipreps DNA Purification System, Promega, A7640) according to the instructions. The specific steps were:

(1) Adding 5 ml of *Escherichia coli* to 300 ml of liquid LB medium containing kanamycin, and shaking at 200 rpm, 37° C. for 12 to 16 hours;

(2) Placing the above bacteria solution in a 500 ml centrifuge tube, and centrifuging at 5,000 g for 10 minutes, discarding the supernatant;

(3) Adding 3 ml of Cell Resuspension Solution (CRS) to resuspend the cell pellet and vortexing for thorough mixing;

(4) Adding 3 ml of Cell Lysis Solution (CLS) and mixing up and down slowly for no more than 5 minutes;

(5) Adding 3 ml of Neutralization Solution and mixed well by overturning until the color become clear and transparent;

(6) Centrifuging at 14,000 g for 15 minutes, and further centrifuging for 15 minutes if precipitate was not formed compact;

(7) Transferring the supernatant to a new 50 ml centrifuge tube, avoiding to suck in white precipitate into the centrifuge tube;

(8) Adding 10 ml of DNA purification resin (Purification Resin, shaken vigorously before use) and mixing well;

(9) Pouring the Resin/DNA mixture was poured into a filter column, and treating by the vacuum pump negative pressure method (0.05 MPa);

(10) Adding 15 ml of Column Wash Solution (CWS) to the filter column, and vacuuming.

(11) Adding 15 ml of CWS, and repeating vacuuming once; vacuuming was extended for 30 s after the whole solution passed through the filter column;

(12) Cutting off the filter column, transferring to a 1.5 ml centrifuge tube, centrifuging at 12,000 g for 2 minutes, removing residual liquid, and transferring the filter column to a new 1.5 ml centrifuge tube;

(13) Adding 200 μL of sterilized water preheated to 70° C., and keeping rest for 2 minutes;

(14) Centrifuging at 12,000 g for 2 minutes to elute the plasmid DNA; and the concentration was generally about 1 μg/μL.

3. Preparing rice protoplasts and performing PEG-mediated transformation:

First, rice seedlings for protoplasts were prepared, which is of the variety Nipponbare. The seeds were provided by the Weeds Department of the School of Plant Protection, China Agricultural University, and expanded in house. The rice seeds were hulled first, and the hulled seeds were rinsed with 75% ethanol for 1 minute, treated with 5% (v/v) sodium hypochlorite for 20 minutes, then washed with sterile water for more than 5 times. After blow-drying in an ultra-clean table, they were placed in a tissue culture bottle containing ½ MS medium, 20 seeds for each bottle. Protoplasts were prepared by incubating at 26° C. for about 10 days with 12 hours light.

The methods for rice protoplast preparation and PEG-mediated transformation were conducted according to "Lin et al., 2018 Application of protoplast technology to CRISPR/Cas9 mutagenesis: from single-cell mutation detection to mutant plant regeneration. Plant Biotechnology Journal". The steps were as follows:

(1) the leaf sheath of the seedlings was selected, cut into pieces of about 1 mm with a sharp Geely razor blade, and placed in 0.6 M mannitol and MES culture medium (formulation: 0.6 M mannitol, 0.4 M MES, pH 5.7) for later use. All materials were cut and transferred to 20 ml of enzymatic hydrolysis solution (formulation: 1.5% Cellulase R10/RS (YaKult Honsha), 0.5% Mecerozyme R10 (YaKult Honsha), 0.5M mannitol, 20 mM KCl, 20 mM MES, pH 5.7, 10 mM $CaCl_2$, 0.1% BSA, 5 mM β-mercaptoethanol), wrapped in tin foil and placed in a 28° C. shaker, enzymatically hydrolyzed at 50 rpm in the dark for about 4 hours, and the speed was increased to 100 rpm in the last 2 minutes;

(2) after the enzymatic lysis, an equal volume of W5 solution (formulation: 154 mM NaCl, 125 mM $CaCl_2$), 5 mM KCl, 15 mM MES) was added, shaken horizontally for 10 seconds to release the protoplasts. The cells after enzymatic lysis were filtered through a 300-mesh sieve and centrifuged at 150 g for 5 minutes to collect protoplasts;

(3) the cells were rinsed twice with the W5 solution, and the protoplasts were collected by centrifugation at 150 g for 5 minutes;

(4) the protoplasts were resuspended with an appropriate amount of MMG solution (formulation: 3.05 g/L $MgCl_2$, 1 g/L MES, 91.2 g/L mannitol), and the concentration of the protoplasts was about $2\times10^6$ cells/mL.

The transformation of protoplasts was carried out as follows:

(1) to 200 μL of the aforementioned MMG resuspended protoplasts, endotoxin-free plasmid DNA of high quality (10-20 μg) was added and tapped to mix well;

(2) an equal volume of 40% (w/v) PEG solution (formulation: 40% (w/v) PEG, 0.5M mannitol, 100 mM $CaCl_2$)) was added, tapped to mix well, and kept rest at 28° C. in the dark for 15 minutes;

(3) after the induction of transformation, 1.5 ml of W5 solution was added slowly, tapped to mix the cells well. The cells were collected by centrifugation at 150 g for 3 minutes. This step was repeated once;

(4) 1.5 ml of W5 solution was added to resuspend the cells, and placed in a 28° C. incubator and cultured in the dark for 12-16 hours. For extracting protoplast genomic DNA, the cultivation should be carried out for 48-60 hours.

4. Genome targeting and detecting new gene:

(1) First, protoplast DNAs were extracted by the CTAB method with some modifications. The specific method was as follows: the protoplasts were centrifuged, then the supernatant was discarded. 500 μL of DNA extracting solution (formulation: CTAB 20 g/L, NaCl 81.82 g/L, 100 mM Tris-HCl (pH 8.0), 20 mM EDTA, 0.2% β-mercaptoethanol) was added, shaken to mix well, and incubated in a 65° C. water bath for 1 hour; when the incubated sample was cooled, 500 μL of chloroform was added and mixed upside down and centrifuged at 10,000 rpm for 10 minutes; 400 μL of the supernatant was transferred to a new 1.5 ml centrifuge tube, 1 ml of 70% (v/v) ethanol was added and the mixture was kept at −20° C. for precipitating for 20 minutes; the mixture was centrifuged at 12,000 rpm for 15 minutes to precipitate the DNA; after the precipitate was air dried, 50 μL of ultrapure water was added and stored at −20° C. for later use.

(2) The detection primers in the following table were used to amplify the fragments containing the target sites on both sides or the predicted fragments resulting from the fusion of the UBI2 promoter and the HPPD coding region. The lengths of the PCR products were between 300-1000 bp, in which the primer8-F+primer6-R combination was used to detect the fusion fragment at the middle joint after the doubling of the chromosome fragment, and the product length was expected to be 630 bp.

| Primer | | Sequence (5' to 3') |
|---|---|---|
| OsHPPDduplicated-primer1-F | SEQ ID NO: 35 | CACTACCATCCATCCATTTGC |
| OsHPPDduplicated-primer6-R | SEQ ID NO: 36 | GAGTTCCCCGTGGAGAGGT |
| OsHPPDduplicated-primer3-F | SEQ ID NO: 37 | TCCATTACTACTCTCCCCGATT |
| OsHPPDduplicated-primer7-R | SEQ ID NO: 38 | GTGTGGGGGAGTGGATGAC |
| OsHPPDduplicated-primer5-F | SEQ ID NO: 39 | TGTAGCTTGTGCGTTTCGAT |
| OsHPPDduplicated-primer2-R | SEQ ID NO: 40 | GGGATGCCCTCTTTGTCC |
| OsHPPDduplicated-primer8-F | SEQ ID NO: 41 | TCTGTGTGAAGATTATTGCCACT |
| OsHPPDduplicated-primer4-R | SEQ ID NO: 42 | GGGATGCCCTCCTTATCTTG |

The PCR reaction system was as follows:

| Components | Volume |
|---|---|
| 2 × I5 buffer solution | 5 μL |
| Forward primer (10 μM) | 2 μL |
| Reverse primer (10 μM) | 2 μL |
| Template DNA | 2 μL |
| Ultrapure water | Added to 50 μL |

(3) A PCR reaction was conducted under the following general reaction conditions:

| Step | Temperature | Time |
|---|---|---|
| Denaturation | 98° C. | 30 s |
| | 98° C. | 15 s |
| Amplification for | 58° C. | 15 s |
| 30-35 cycles | 72° C. | 30 s |

-continued

| Step | Temperature | Time |
|---|---|---|
| Final extension | 72° C. | 3 min |
| Finished | 16° C. | 5 min |

(4) The PCR reaction products were detected by 1% agarose gel electrophoresis. The results showed that the 630 bp positive band for the predicted fusion fragment of the UBI2 promoter and the HPPD coding region could be detected in the pQY002066 and pQY002068 transformed samples.

5. The positive samples of the fusion fragment of the UBI2 promoter and the HPPD coding region were sequenced for verification, and the OsHPPDduplicated-primer8-F and OsHPPDduplicated-primer6-R primers were used to sequence from both ends. As shown in FIG. 5, the promoter of the UBI2 gene and the expression region of the HPPD gene could be directly ligated, and the editing event of the fusion of the promoter of rice UBI2 gene and the expression region of the HPPD gene could be detected in the protoplast genomic DNA of the rice transformed with pQY002066 and pQY002068 plasmids, indicating that the scheme of doubling the chromosome fragments to form a new HPPD gene was feasible, a new HPPD gene which expression was driven by a strong promoter could be created, and this was defined as an HPPD doubling event. The sequencing result of the pQY002066 vector transformed protoplast for testing HPPD doubling event was shown in SEQ ID NO: 9; and the sequencing result of the pQY002068 vector transformed protoplast for testing HPPD doubling event was shown in SEQ ID NO: 10.

Figure 6:
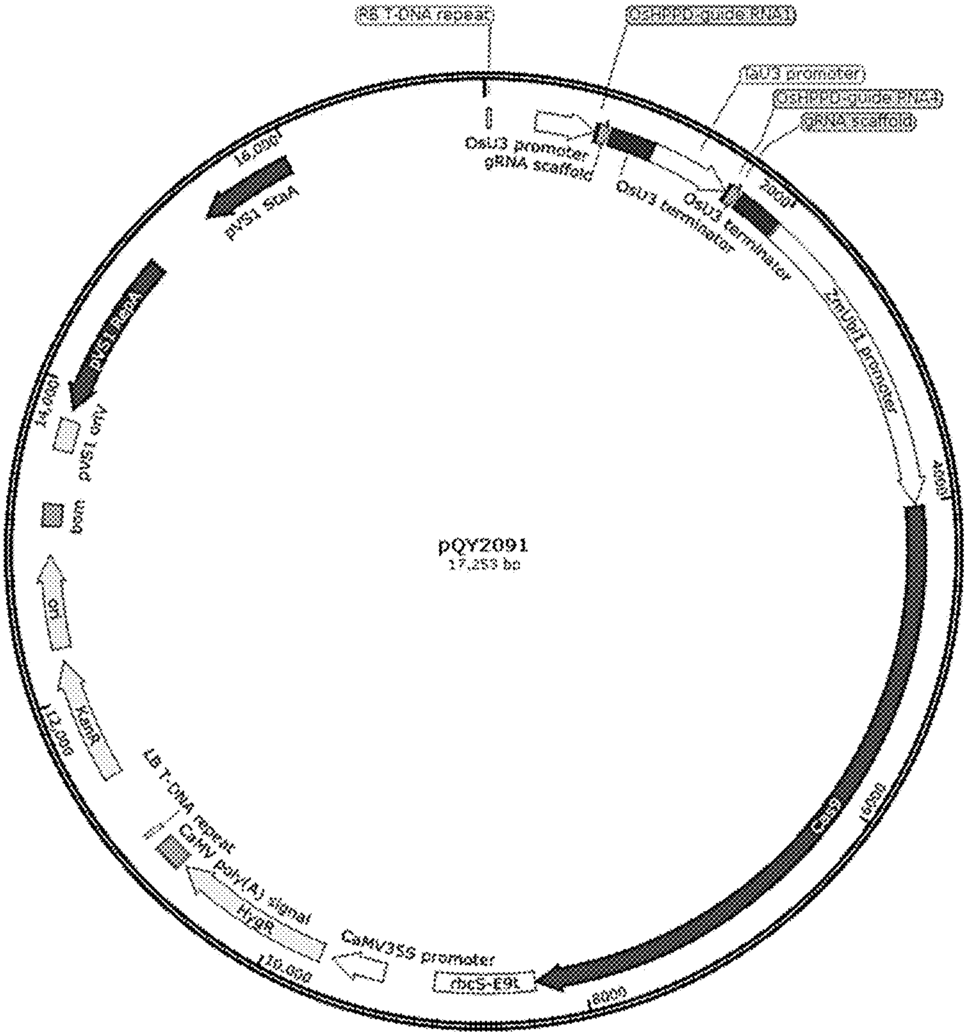
FIG. 6 shows the map of the *Agrobacterium* transformation vector pQY2091 for rice.

Example 2: Creation of Herbicide-Resistant Rice with Knock-Up Expression of Endogenous HPPD Gene by Chromosome Fragment Doubling Through *Agrobacterium*-Mediated Transformation 1. Construction of knock-up editing vector: Based on the results of the protoplast test in Example 1, the dual-target combination OsHPPD-guide RNA1: 5'GTGCTGGTTGCCTTGGCTGC3' (SEQ ID NO: 27) and OsHPPD-guide RNA4: 5'GAAATAATCACCAAACAGAT3' (SEQ ID NO: 30) with a high editing efficiency was selected. The *Agrobacterium* transformation vector pQY2091 was constructed according to Example 1. pHUE411 was used as the vector backbone and subjected to rice codon optimization. The map of the vector was shown in FIG. 6.
2. *Agrobacterium* transformation of rice callus:

1) *Agrobacterium* transformation: 1 μg of the rice knock-up editing vector pQY2091 plasmid was added to 10 μl of *Agrobacterium* EHA105 heat-shock competent cells (Angyu Biotech, Catalog No. G6040), placed on ice for 5 minutes, immersed in liquid nitrogen for quick freezing for 5 minutes, then removed and heated at 37° C. for 5 minutes, and finally placed on ice for 5 minutes. 500 μl of YEB liquid medium (formulation: yeast extract 1 g/L, peptone 5 g/L, beef extract 5 g/L, sucrose 5 g/L, magnesium sulfate 0.5 g/L) was added. The mixture was placed in a shaker and incubated at 28° C., 200 rpm for 2~3 hours; the bacteria were collected by centrifugation at 3500 rpm for 30 seconds, the collected bacteria were spread on YEB (kanamycin 50 mg/L+rifampicin 25 mg/L) plate, and incubated for 2 days in an incubator at 28° C.; the single colonies were picked and placed into liquid culture medium, and the bacteria were stored at −80° C.

2) Cultivation of *Agrobacterium*: The single colonies of the transformed *Agrobacterium* on the YEB plate was picked, added into 20 ml of YEB liquid medium (kanamycin 50 mg/L+rifampicin 25 mg/L), and cultured while stirring at 28° C. until the OD600 was 0.5, then the bacteria cells were collected by centrifugation at 5000 rpm for 10 minutes, 20-40 ml of AAM (Solarbio, lot number LA8580) liquid medium was added to resuspend the bacterial cells to reach OD600 of 0.2-0.3, and then acetosyringone (Solarbio, article number A8110) was added to reach the final concentration of 200 μM for infecting the callus.

3) Induction of rice callus: The varieties of the transformation recipient rice were Huaidao 5 and Jinjing 818, purchased from the seed market in Huai'an, Jiangsu, and expanded in house. 800-2000 clean rice seeds were hulled, then washed with sterile water until the water was clear after washing. Then the seeds were disinfected with 70% alcohol for 30 seconds, then 30 ml of 5% sodium hypochlorite was added and the mixture was placed on a horizontal shaker and shaken at 50 rpm for 20 minutes, then washed with sterile water for 5 times. The seeds were placed on sterile absorbent paper, air-dried to remove the water on the surface of the seeds, inoculated on an induction medium and cultivated at 28° C. to obtain callus.

The formulation of the induction medium: 4.1 g/L N6 powder+0.3 g/L hydrolyzed casein+2.878 g/L proline+2 mg/L 2,4-D+3% sucrose+0.1 g/L inositol+0.5 g glutamine+0.45% phytagel, pH 5.8.

4) Infection of rice callus with *Agrobacterium*: The callus of Huaidao No. 5 or Jinjing 818 subcultured for 10 days with a diameter of 3 mm was selected and collected into a 50 ml centrifuge tube; the resuspension solution of the *Agrobacterium* AAM with the OD600 adjusted to 0.2-0.3 was poured into the centrifuge tube containing the callus, placed in a shaker at 28° C. at a speed of 200 rpm to perform infection for 20 minutes; when the infection was completed, the bacteria solution was discarded, the callus was placed on sterile filter paper and air-dried for about 20 minutes, then placed on a plate containing co-cultivation medium to perform co-cultivation, on which the plate was covered with a sterile filter paper soaked with AAM liquid medium containing 100 μM acetosyringone; after 3 days of co-cultivation, the *Agrobacterium* was removed by washing (firstly washing with sterile water for 5 times, then washing with 500 mg/L cephalosporin antibiotic for 20 minutes), and selective cultured on 50 mg/L hygromycin selection medium.

The formulation of the co-cultivation medium: 4.1 g/L N6 powder+0.3 g/L hydrolyzed casein+0.5 g/L proline+2 mg/L 2,4-D+200 μM AS+10 g/L glucose+3% Sucrose+0.45% phytagel, pH 5.5.

3. Molecular identification and differentiation into seedlings of hygromycin resistant callus:

Different from the selection process of conventional rice transformation, with specific primers of the fusion fragments generated after the chromosome fragment doubling, hygromycin resistant callus could be molecularly identified during the callus selection and culture stage in the present invention, positive doubling events could be determined, and callus containing new genes resulting from fusion of different genetic elements was selected for differentiation cultivation and induced to emerge seedlings. The specific steps were as follows:

1) The co-cultured callus was transferred to the selection medium for the first round of selection (2 weeks). The formulation of the selection medium is: 4.1 g/L N6 powder+0.3 g/L hydrolyzed casein+2.878 g/L proline+2 mg/L 2,4-D+3% sucrose+0.5 g glutamine+30 mg/L hygromycin (HYG)+500 mg/L cephalosporin (cef)+0.1 g/L inositol+0.45% phytagel, pH 5.8.

Figure 7:
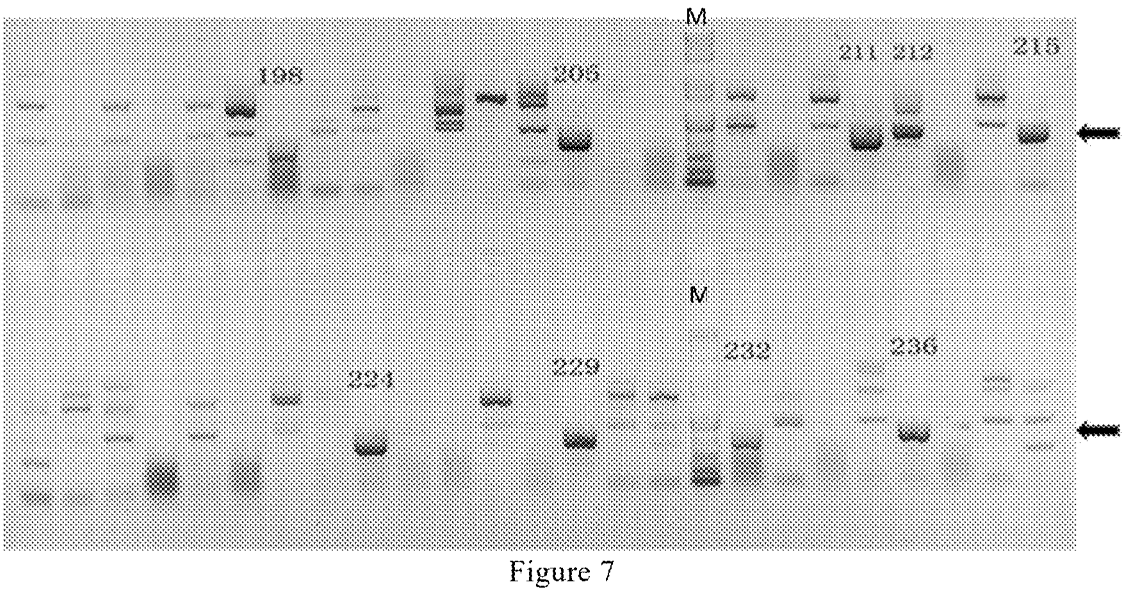
FIG. 7 shows the electrophoresis results of the PCR products for the detection of new gene fragments in pQY2091 transformed hygromycin resistant rice callus. The arrow indicates the PCR band of the new gene created by the fusion of the promoter of the UBI2 gene with the coding region of the HPPD. The numbers are the numbers of the different callus samples. M represents DNA Marker, and the band sizes are 100 bp, 250 bp, 500 bp, 750 bp, 1000 bp, 2000 bp, 2500 bp, 5000 bp, 7500 bp in order.

2) After the first round of selection was completed, the newly grown callus was transferred into a new selection medium for the second round of selection (2 weeks). At this stage, the newly grown callus with a diameter greater than 3 mm was clamped by tweezers to take a small amount of sample, the DNA thereof was extracted with the CTAB method described in Example 1 for the first round of molecular identification. In this example, the primer pair of OsHPPDduplicated-primer8-F (8F) and OsHPPDduplicated-primer6-R (6R) was selected to perform PCR identification for the callus transformed with the pQY2091 vector, in which the reaction system and reaction conditions were similar to those of Example 1. Among the total of 350 calli tested, no positive sample was detected in the calli of Huaidao 5, while 28 positive samples were detected in the calli of Jinjing 818. The PCR detection results of some calli were shown in FIG. 7.

3) The calli identified as positive by PCR were transferred to a new selection medium for the third round of selection and expanding cultivation; after the diameter of the calli was greater than 5 mm, the callus in the expanding cultivation was subjected to the second round of molecular identification using 8F+6R primer pair, the yellow-white callus at good growth status that was identified as positive in the second round was transferred to a differentiation medium to perform differentiation, and the seedlings of about 1 cm could be obtained after 3 to 4 weeks; the differentiated seedlings were transferred to a rooting medium for rooting cultivation; after the seedlings of the rooting cultivation were subjected to hardening off, they were transferred to a flowerpot with soil and placed in a greenhouse for cultivation. The formulation of the differentiation medium is: 4.42 g/L MS powder+0.5 g/L hydrolyzed casein+0.2 mg/L NAA+2 mg/L KT+3% sucrose+3% sorbitol+30 mg/L hygromycin+0.1 g/L inositol+0.45% phytagel, pH 5.8. The formulation of the rooting medium is: 2.3 g/L MS powder+3% sucrose+0.45% phytagel.

Figure 8:
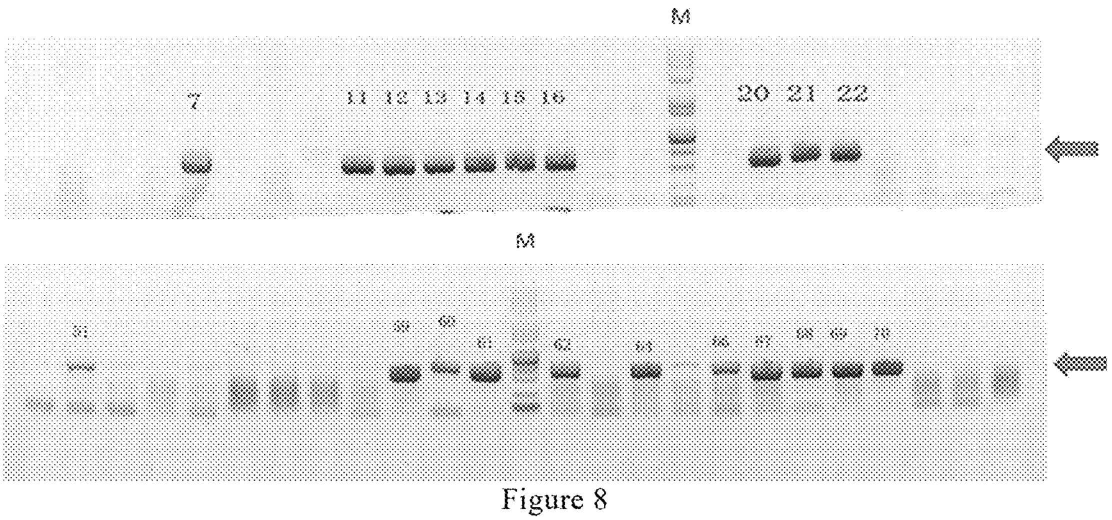
FIG. 8 shows the electrophoresis results of the PCR products for the detection of new gene fragments in pQY2091 transformed rice T0 seedlings. The arrow indicates the PCR band of the new gene created by the fusion of the promoter of the UBI2 gene with the coding region of the HPPD. The numbers are the serial numbers of the different T0 seedlings. M represents DNA Marker, and the band sizes are sequentially 100 bp, 250 bp, 500 bp, 750 bp, 1000 bp, 2000 bp, 2500 bp, 5000 bp, 7500 bp.

4. Molecular detection of HPPD doubling seedlings (T0 generation):

After the second round of molecular identification, 29 doubling event-positive calli were co-differentiated to obtain 403 seedlings of T0 generation, and the 8F+6R primer pair was used for the third round of molecular identification of the 403 seedlings, among which 56 had positive bands. The positive seedlings were moved into a greenhouse for cultivation. The PCR detection results of some T0 seedlings were shown in FIG. 8.

5. HPPD inhibitory herbicide resistance test for HPPD doubled seedlings (T0 generation):

The transformation seedlings of T0 generation identified as doubling event positive were transplanted into large plastic buckets in the greenhouse for expanding propagation to obtain seeds of T1 generation. After the seedlings began to tiller, the tillers were taken from vigorously growing strains, and planted in the same pots with the tillers of the wild-type control varieties at the same growth period. After the plant height reached about 20 cm, the herbicide resistance test was conducted. The herbicide used was Shuangzuocaotong (CAS No. 1622908-18-2) produced by our company, and its field dosage was usually 4 grams of active ingredients per mu (4 g a.i./mu). In this experiment, Shuangzuocaotong was applied at a dosage gradient of 2 g a.i./mu, 4 g a.i./mu, 8 g a.i./mu and 32 g a.i./muwith a walk-in spray tower.

Figure 9:
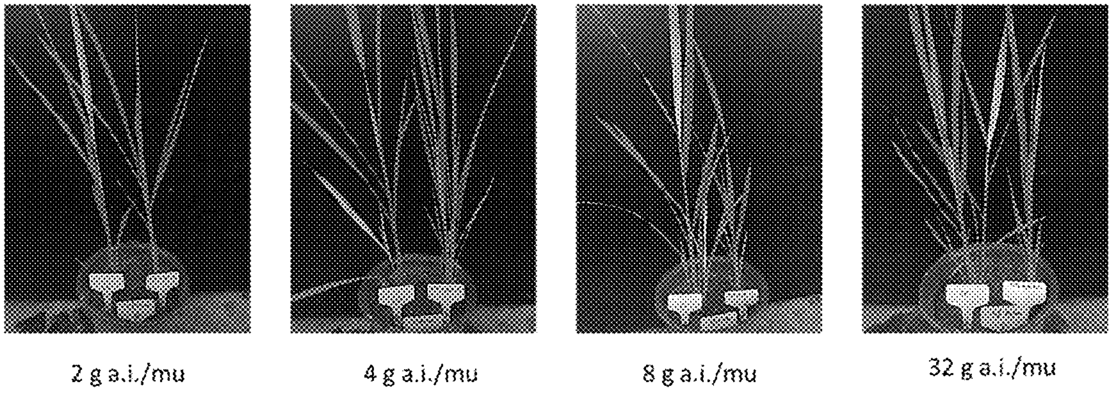
FIG. 9 shows the test results for the resistance to Shuangzuocaotong of the QY2091 T0 generation of the HPPD gene doubling strain. In the same flowerpot, the wild-type Jinjing 818 is on the left, and the HPPD doubling strain is on the right.

The resistance test results were shown in FIG. 9. After 5-7 days of the application, the wild-type control rice seedlings began to show albino, while the strains of the HPPD doubling events all remained normally green. After 4 weeks of the application, the wild-type rice seedlings were close to death, while the strains of the doubling events all continued to remain green and grew normally. The test results showed that the HPPD gene-doubled strains had a significantly improved tolerance to Shuangzuocaotong.

6. Quantitative detection of the relative expression of the HPPD gene in the HPPD doubled seedlings (T0 generation):

It was speculated that the improved resistance of the HPPD gene doubled strain to Shuangzuocaotong was due to the fusion of the strong promoter of UBI2 and the HPPD gene CDS that increased the expression of HPPD, so the T0 generation strains QY2091-13 and QY2091-20 were used to take samples from the primary tillers and the secondary tillers used for herbicide resistance test to detect the expression levels of the HPPD and UBI2 genes, respectively, with the wild-type Jinjing 818 as the control. The specific steps were as follows:

1) Extraction of Total RNA (Trizol Method):

0.1-0.3 g of fresh leaves were taken and ground into powder in liquid nitrogen. 1 ml of Trizol reagent was added for every 50-100 mg of tissue for lysis; the Trizol lysate of the above tissue was transferred into a 1.5 ml centrifuge tube, stood at room temperature (15-30° C.) for 5 minutes; chloroform was added in an amount of 0.2 ml per 1 ml of Trizol; the centrifuge tube was capped, shaken vigorously in hand for 15 seconds, stood at room temperature (15-30° C.) for 2-3 minutes, then centrifuged at 12000 g (4° C.) for 15 minutes; the upper aqueous phase was removed and placed in a new centrifuge tube, isopropanol was added in an amount of 0.5 ml per 1 ml of Trizol, the mixture was kept at room temperature (15-30° C.) for 10 minutes, then centrifuged at 12000 g (2-8° C.) for 10 minutes; the supernatant was discarded, and 75% ethanol was added to the pellet in an amount of 1 ml per 1 ml of Trizol for washing. The mixture was vortexed, and centrifuged at 7500 g (2-8° C.) for 5 minutes. The supernatant was discarded; the precipitated RNA was dried naturally at room temperature for 30 minutes; the RNA precipitate was dissolved by 50 μl of RNase-free water, and stored in the refrigerator at −80° C. after electrophoresis analysis and concentration determination.

2) RNA Electrophoresis Analysis:

An agarose gel at a concentration of 1% was prepared, then 1 μl of the RNA was taken and mixed with 1 μl of 2× Loading Buffer. The mixture was loaded on the gel. The voltage was set to 180V and the time for electrophoresis was 12 minutes. After the electrophoresis was completed, the agarose gel was taken out, and the locations and brightness of fragments were observed with a UV gel imaging system.

3) RNA Purity Detection:

The RNA concentration was measured with a microprotein nucleic acid analyzer. RNA with a good purity had an OD260/OD280 value between 1.8-2.1. The value lower than 1.8 indicated serious protein contamination, and higher than 2.1 indicated serious RNA degradation.

4) Real-Time Fluorescence Quantitative PCR

The extracted total RNA was reverse transcribed into cDNA with a special reverse transcription kit. The main procedure comprised: first determining the concentration of the extracted total RNA, and a portion of 1-4 μg of RNA was used for synthesizing cDNA by reverse transcriptase synthesis. The resulting cDNA was stored at −20° C.

① A solution of the RNA template was prepared on ice as set forth in the following table and subjected to denaturation and annealing reaction in a PCR instrument. This process was conducive to the denaturation of the RNA template and the specific annealing of primers and templates, thereby improving the efficiency of reverse transcription.

TABLE 1

| Reverse transcription, denaturation and annealing reaction system | |
|---|---|
| Component | Amounts (μl) |
| Oligo dT primer (50 μM) | 1 μl |
| dNTP mixture (10 mM each) | 1 μl |
| RNA Template | 1-4 μg |
| RNase free water | Added to 10 μL |
| Reaction conditions for denaturation and annealing: | |
| 65° C. | 5 min |
| 4° C. | 5 min |

② The reverse transcription reaction system was prepared as set forth in Table 2 for synthesizing CDNA:

TABLE 2

| Reverse transcription reaction system | |
|---|---|
| Component | Amount (μl) |
| Reaction solution after the above denaturation and annealing | 10 μl |
| 5× RTase Plus Reaction Buffer | 4 μl |
| RNase Inhibitor | 0.5 μl |
| Evo M-MLV Plus RTase (200 U/μl ) | 1 μl |
| RNase free water | Added to 20 μL |
| Reaction conditions for cDNA synthesis: | |
| 42° C. | 60 min |
| 95° C. | 5 min |

③ The UBQ5 gene of rice was selected as the internal reference gene, and the synthesized cDNA was used as the template to perform fluorescence quantitative PCR. The primers listed in Table 3 were used to prepare the reaction solution according to Table 4.

TABLE 3

| Sequence 5'-3' of the primer for Fluorescence quantitative PCR | | |
|---|---|---|
| UBQ5-F | SEQ ID NO: 43 | ACCACTTCGACCGCCACTACT |
| UBQ5-R | SEQ ID NO: 44 | ACGCCTAAGCCTGCTGGTT |
| RT-OsHPPD-F | SEQ ID NO: 45 | CAGATCTTCACCAAGCCAGTAG |

TABLE 3-continued

| Sequence 5'-3' of the primer for Fluorescence quantitative PCR | | |
|---|---|---|
| RT-OsHPPD-R | SEQ ID NO: 46 | GAGAAGTTGCCCTTCCCAAA |
| RT-OsUbi2-F | SEQ ID NO: 47 | CCTCCGTGGTGGTCAGTAAT |
| RT-OsUbi2-R | SEQ ID NO: 48 | GAACAGAGGCTCGGGACG |

TABLE 4

| Reaction solution for real-time quantitative PCR (Real Time PCR) | |
|---|---|
| Component of mixture | Amount (μl) |
| SYBR Premix ExTaq II | 5 μl |
| Forward primer (10 μM) | 0.2 μl |
| Reverse primer (10 μM) | 0.2 μl |
| cDNA | 1 μl |
| Rox II | 0.2 μl |
| Ultrapure water | 3.4 μl |
| In total | 10 μl |

④ The reaction was performed following the real-time quantitative PCR reaction steps in Table 5. The reaction was conducted for 40 cycles.

TABLE 5

| Real-time quantitative PCR reaction steps | |
|---|---|
| Temperature (° C.) | Time |
| 50° C. | 2 min |
| 95° C. | 10 min |
| 95° C. | 15 s |
| 60° C. | 20 s |
| 95° C. | 15 s |
| 60° C. | 20 s |
| 95° C. | 15 s |

5) Data Processing and Experimental Results

As shown in Table 6, UBQ5 was used as an internal reference, ΔCt was calculated by subtracting the Ct value of UBQ5 from the Ct value of the target gene, and then $2^{-\Delta Ct}$ was calculated, which represented the relative expression level of the target gene. The 818CK1 and 818CK3 were two wild-type Jinjing 818 control plants; 13M and 20M represented the primary tiller leaf samples of QY2091-13 and QY2091-20 T0 plants; 13L and 20L represented the secondary tiller leaf samples of QY2091-13 and QY2091-20 T0 plants used for herbicide resistance testing.

TABLE 6

Ct values and relative expression folds of different genes

| | UBQ5 | Mean | UBI2 | ΔCt | $2^{-\Delta Ct}$ | Mean | HPPD | ΔCt | $2^{-\Delta Ct}$ | Mean |
|---|---|---|---|---|---|---|---|---|---|---|
| | 23.27 | | 17.56 | −5.88 | 58.95 | | 20.81 | −2.63 | 6.20 | |
| | 23.55 | | 17.71 | −5.73 | 53.09 | | 21.01 | −2.43 | 5.40 | |
| 818CK1 | 23.51 | 23.44 | 17.66 | −5.78 | 55.06 | 55.70 | 20.98 | −2.47 | 5.52 | 5.71 |
| | 23.45 | | 17.88 | −5.50 | 45.20 | | 20.93 | −2.44 | 5.43 | |
| | 23.19 | | 17.94 | −5.44 | 43.41 | | 21.13 | −2.24 | 4.74 | |
| 818CK3 | 23.49 | 23.37 | 17.72 | −5.65 | 50.26 | 46.29 | 21.14 | −2.24 | 4.72 | 4.96 |
| | 24.61 | | 19.56 | −4.92 | 30.32 | | 20.23 | −4.25 | 19.07 | |
| | 24.27 | | 19.52 | −4.96 | 31.05 | | 20.29 | −4.19 | 18.28 | |
| 13M | 24.56 | 24.48 | 19.16 | −5.32 | 39.97 | 33.78 | 20.48 | −4.00 | 15.99 | 17.78 |
| | 23.98 | | 18.76 | −5.20 | 36.70 | | 19.02 | −4.94 | 30.64 | |
| | 23.89 | | 18.52 | −5.43 | 43.19 | | 19.07 | −4.89 | 29.56 | |
| 13L | 24.00 | 23.96 | 18.81 | −5.14 | 35.34 | 38.41 | 19.07 | −4.88 | 29.45 | 29.88 |
| | 24.34 | | 19.01 | −5.40 | 42.30 | | 19.37 | −5.04 | 32.98 | |
| | 24.41 | | 19.07 | −5.34 | 40.64 | | 19.33 | −5.09 | 34.05 | |
| 20M | 24.49 | 24.41 | 19.29 | −5.13 | 35.00 | 39.32 | 19.26 | −5.16 | 35.65 | 34.22 |
| | 24.63 | | 19.46 | −5.11 | 34.52 | | 19.88 | −4.69 | 25.83 | |
| | 24.67 | | 19.38 | −5.19 | 36.48 | | 19.91 | −4.66 | 25.31 | |
| 20L | 24.41 | 24.57 | 19.42 | −5.15 | 35.61 | 35.54 | 19.86 | −4.71 | 26.16 | 25.77 |

Figure 10:
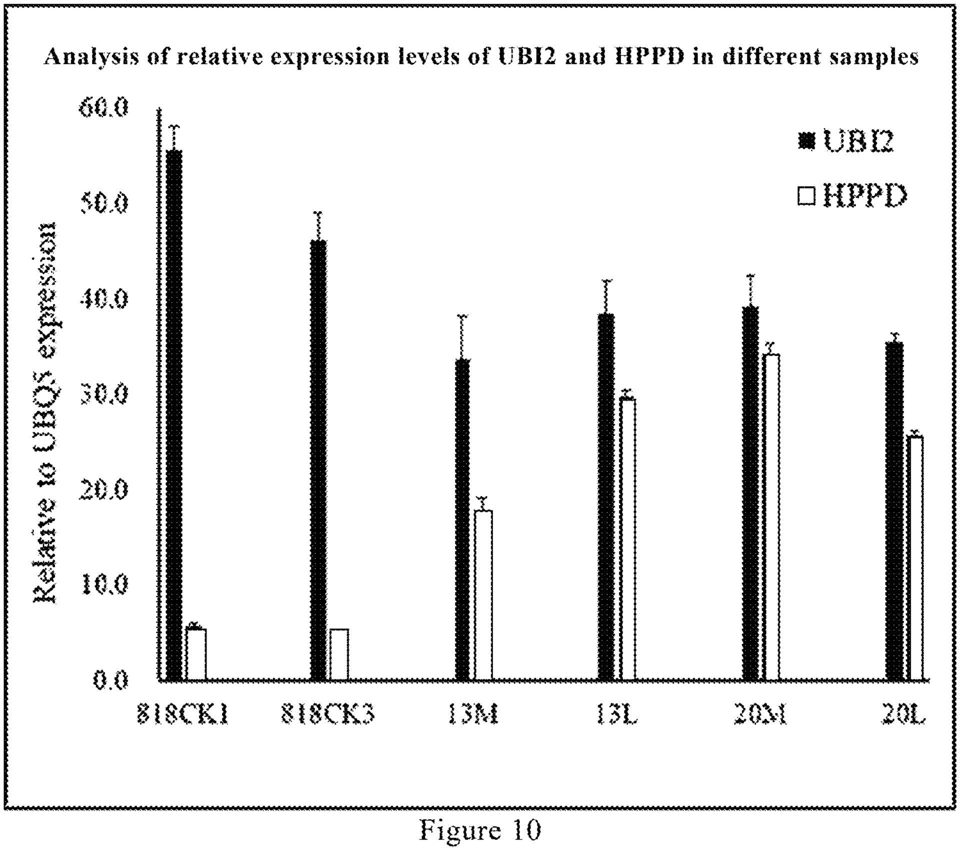
FIG. 10 shows the relative expression levels of the HPPD and UBI2 genes in the QY2091 T0 generation of the HPPD gene doubling strain. 818CK1 and 818CK3 represent two control plants of the wild-type Jinjing 818; 13M and 20M represent the primary tiller leaf samples of the QY2091-13 and the QY2091-20 T0 plants; 13L and 20L represent the secondary tiller leaf samples of the QY2091-13 and the QY2091-20 T0 plants used in the herbicide resistance test.

The results were shown in FIG. 10. The rice UBQ5 was used as an internal reference gene to calculate the relative expression levels of the OsHPPD and UBI2 genes. The results showed that the HPPD expression level of the HPPD doubled strain was significantly higher than that of the wild type, indicating that the fused UBI2 strong promoter did increase the expression level of HPPD, thereby creating a highly-expressing HPPD gene, with the HPPD gene knocked up. The slight decrease in the expression level of UBI2 could be due to the small-scale mutations resulting from the edition of the promoter region, and we had indeed detected base insertions, deletions or small fragment deletions at the UBI2 target site. Compared with the wild type, the expression levels of UBI2 and HPPD significantly tended to be consistent and met the theoretical expectations; among them, the HPPD expression level of the 20M sample was about 6 times higher than that of the wild type CK3 group.

The above results proved that, following the effective chromosome fragment doubling program as tested in protoplasts, calli and transformed seedlings with doubling events could be selected by multiple rounds of molecular identification during the *Agrobacterium* transformation and tissue culturing, and the UBI2 strong promoter in the new HPPD gene fusion generated in the transformed seedlings did increase the expression level of HPPD gene, rendering the plants to get resistance to HPPD inhibitory herbicide Shuangzuocaotong, up to 8 times the field dose, and thus a herbicide-resistant rice with knock-up endogenous HPPD gene was created. Taking this as an example, using the chromosome fragment doubling technical solution of Example 1 and Example 2, a desired promoter could also be introduced into an endogenous gene which gene expression pattern should be changed to create a new gene, and a new variety of plants with desired gene expression pattern could be created through *Agrobacterium*-mediated transformation.

Example 3: Molecular Detection and Herbicide Resistance Test of T1 Generation of Herbicide-Resistant Rice Strain with Knock-Up Expression of the Endogenous HPPD Gene Caused By Chromosome Fragment Doubling The physical distance between the HPPD gene and the UBI2 gene in the wild-type rice genome was 338 kb, as shown in Scheme 1 in FIG. 1. The length of the chromosome was increased by 338 kb after the chromosome fragment between them was doubled by duplication, and a highly-expressing new HPPD gene was generated with a UBI2 promoter at the joint of the duplicated fragment to drive the expression of the HPPD CDS region. In order to determine whether the new gene could be inherited stably and the effect of the doubling chromosome fragment on the genetic stability, molecular detection and herbicide resistance test was conducted for the T1 generation of the HPPD doubled strains.

First of all, it was observed that the doubling event had no significant effect on the fertility of T0 generation plants, as all positive T0 strains were able to produce normal seeds. Planting test of T1 generation seedlings were further conducted for the QY2091-13 and QY2091-20 strains.

1. Sample Preparation:

For QY2091-13, a total of 36 T1 seedlings were planted, among which 27 grew normally and 9 were albino. 32 were selected for DNA extraction and detection, where No. 1-24 were normal seedlings, and No. 25-32 were albino seedlings.

For QY2091-20, a total of 44 T1 seedlings were planted, among which 33 grew normally and 11 were albino. 40 were selected for DNA extraction and detection, where No. 1-32 were normal seedlings, and No. 33-40 were albino seedlings.

Albino seedlings were observed in the T1 generation plants. It was speculated that, since HPPD was a key enzyme in the chlorophyll synthesis pathway of plants, and the T0 generation plants resulting from the dual-target edition possibly could be chimeras of many genotypes such as doubling, deletion, inversion of chromosome fragments, or small fragment mutation at the edited target site. The albino phenotype could be generated in the plants where the HPPD gene was destroyed, for example, the HPPD CDS region was deleted. Different primer pairs were designed for PCR to determine possible genotypes.

2. PCR Molecular Identification:

1) Sequences of detection primers: sequence 5'-3'

```
Primer 8F:
                                        (SEQ ID NO: 49)
TCTGTGTGAAGATTATTGCCACTAGTTC

Primer 6R:
                                        (SEQ ID NO: 50)
GAGTTCCCCGTGGAGAGGT

Test 141-F:
                                        (SEQ ID NO: 51)
CCCCTTCCCTCTAAAAATCAGAACAG

Primer 4R:
                                        (SEQ ID NO: 52)
GGGATGCCCTCCTTATCTTGGATC

Primer 3F:
                                        (SEQ ID NO: 53)
CCTCCATTACTACTCTCCCCGATTC

Primer 7R:
                                        (SEQ ID NO: 54)
GTGTGGGGGAGTGGATGACAG

pg-Hyg-R1:
                                        (SEQ ID NO: 55)
TCGTCCATCACAGTTTGCCA

pg-35S-F:
                                        (SEQ ID NO: 56)
TGACGTAAGGGATGACGCAC
```

Figure 11:
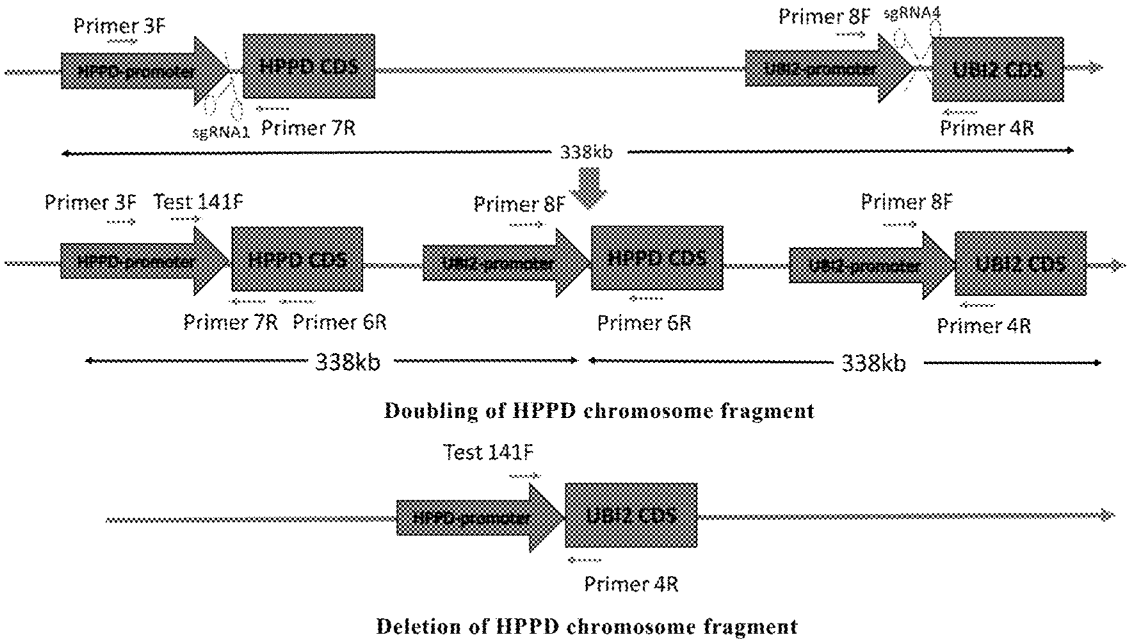
FIG. 11 shows a schematic diagram of the possible genotypes of QY2091 T1 generation and the binding sites of the molecular detection primers. HPPD is SEQ ID NO: 6. UBI2 is SEQ ID NO: 5. Primer 8F is SEQ ID NO: 49. Primer 6R is SEQ ID NO: 50. Test 141-F is SEQ ID NO: 51. Primer 4R is SEQ ID NO: 52. Primer 3F is SEQ ID NO: 53. Primer 7R is SEQ ID NO: 54.

2) The binding sites of the above primers were shown in FIG. 11. Among them, the Primer 8F+Primer 6R were used to detect the fusion fragment of the UBI2 promoter and the HPPD CDS after the chromosome fragment doubling, and the length of the product was 630 bp; the Test 141-F+Primer 4R were used to detect chromosome fragment deletion event, and the length of the product was 222 bp; and the pg-Hyg-R1+pg-35S-F were used to detect the T-DNA fragment of the editing vector, and the length of the product was 660 bp.

3) PCR reaction system, reaction procedure and gel electrophoresis detection were performed according to Example 1.

3. Molecular Detection Results:

The detection results of doubling and deletion events were shown in Table 7. It could be noted that the chromosome fragment doubling events and deletion events were observed in the T1 generation plants, with different rations among different lines. The doubling events in the QY2091-13 (29/32) were higher than that in the QY2091-20 (21/40), possibly due to the different chimeric ratios in the T0 generation plants. The test results indicated that the fusion gene generated by the doubling was heritable.

TABLE 7

| Detection results of doubling and deletion events | | | | | | | | | | | | | | | | | | | | |
|---|---|---|---|---|---|---|---|---|---|---|---|---|---|---|---|---|---|---|---|---|
| QY2091-20 | 1 | 2 | 3 | 4 | 5 | 6 | 7 | 8 | 9 | 10 | 11 | 12 | 13 | 14 | 15 | 16 | 17 | 18 | 19 | 20 |
| Doubling | + | − | − | − | + | + | + | − | − | − | + | − | − | − | − | − | + | + | + | − |
| Deletion | − | − | − | − | − | + | − | − | + | − | − | + | − | − | − | − | − | − | − | − |
| QY2091-20 | 21 | 22 | 23 | 24 | 25 | 26 | 27 | 28 | 29 | 30 | 31 | 32 | 33 | 34 | 35 | 36 | 37 | 38 | 39 | 40 |
| Doubling | − | + | − | − | + | − | + | + | + | − | + | + | + | − | + | + | + | + | + | − |
| Deletion | − | − | + | + | − | + | − | − | − | + | + | − | + | − | + | − | − | − | − | + |

TABLE 7-continued

Detection results of doubling and deletion events

| QY2091-13 | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Doubling | + | − | + | + | + | + | + | − | + | + | + | + | + | + | + | + | + | + | + | + |
| Deletion | − | + | − | + | + | + | − | + | − | − | + | − | − | − | − | − | − | − | − | + |

| QY2091-13 | 21 | 22 | 23 | 24 | 25 | 26 | 27 | 28 | 29 | 30 | 31 | 32 |
|---|---|---|---|---|---|---|---|---|---|---|---|---|
| Doubling | − | + | + | + | + | + | + | + | + | + | + | + |
| Deletion | − | − | + | − | − | + | − | − | + | + | − | + |

The pg-Hyg-R1+pg-35S-F primers were used to detect the T-DNA fragment of the editing vector for the above T1 seedlings. The electrophoresis results of the PCR products of QY2091-20-17 and QY2091-13-7 were negative for the T-DNA fragment, indicating that it was a homozygous doubling. It could be seen that doubling-homozygous non-transgenic strains could be segregated from the T1 generation of the doubling events.

4. Detection of Editing Events by Sequencing:

The doubling fusion fragments were sequenced for the doubling-homozygous positive T1 generation samples 1, 5, 7, 11, 18 and 19 for QY2091-20 and for the doubling-homozygous positive T1 samples 1, 3, 7, 9, 10 and 12 for QY2091-13. The left target site of the HPPD gene and the right target site of the UBI2 were amplified at the same time for sequencing to detect the editing events at the target sites. Among them, the Primer 3F+Primer 7R were used to detect the editing event of the left HPPD target site, where the wild-type control product was 481 bp in length; the Primer 8F+Primer 4R were used to detect the editing event of the right UBI2 target site, where the wild-type control product was 329 bp in length.

Figure 12:
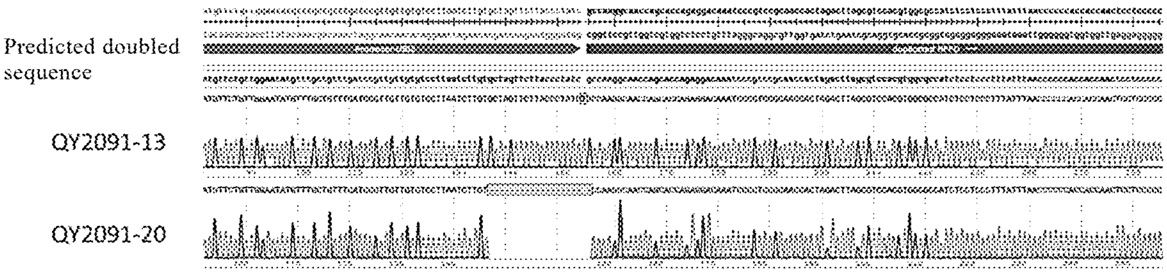
FIG. 12 shows the comparison of the sequencing results detecting the HPPD doubling and the predicted doubled sequences for QY2091-13 (SEQ ID NO: 18) and QY2091-20 (SEQ ID NO: 19).

1) Genotype of the doubling events:

The sequencing result of the HPPD doubling in QY2091-13 was shown in SEQ ID NO: 18, and the sequencing result of the HPPD doubling in QY2091-20 was shown in SEQ ID NO: 19, see FIG. 12. Compared with the predicted linker sequences of the doubling, one T base was inserted at the linker in QY2091-13, 19 bases were deleted from the linker in QY2091-20, and both of the insertion and deletion occurred in the promoter region of UBI2 and had no effect on the coding region of the HPPD protein. From the detection results on the expression levels of the HPPD gene in Example 2, it can be seen that the expression levels of these new HPPD genes where the UBI2 promoters were fused to the HPPD CDS region was significantly increased.

2) Editing events at the original HPPD and UBI2 target sites on both sides:

There were more types of editing events at the target sites on both sides. In two lines, three editing types occurred in the HPPD promoter region, namely insertion of single base, deletion of 17 bases, and deletion of 16 bases; and two editing types occurred in the UBI2 promoter region, namely insertion of 7 bases and deletion of 3 bases. The T1 plants used for testing and sampling were all green seedlings and grew normally, indicating that small-scale mutations in these promoter regions had no significant effect on gene function, and herbicide-resistant rice varieties could be selected from their offspring.

5. Herbicide Resistance Test on Seedlings of T1 Generation:

The herbicide resistance of the T1 generation of the QY2091 HPPD doubled strain was tested at the seedling stage. After the T1 generation seeds were subjected to surface disinfection, they germinated on ½ MS medium containing 1.2 μM Shuangzuocaotong, and cultivated at 28° C., 16 hours light/8 hours dark, in which wild-type Jinjing 818 was used as a control.

Figure 13:
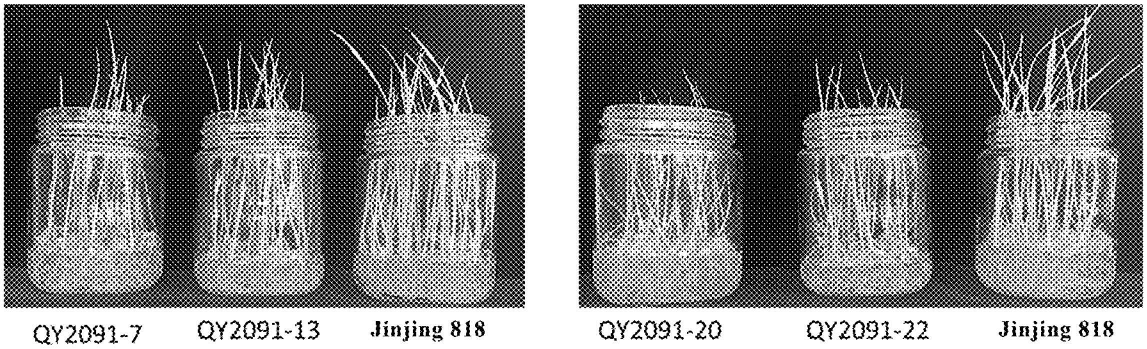
FIG. 13 shows the results of the herbicide resistance test for the T1 generation of the QY2091 HPPD doubling strain at the seedling stage.

The test results of resistance were shown in FIG. 13. After 10 days of cultivation in light, the wild-type control rice seedlings showed phenotypes of albinism and were almost all albino, while the lines of the HPPD doubling events QY2091-7, 13, 20, 22 showed phenotype segregation of chlorosis and green seedlings. According to the aforementioned molecular detection results, there was genotype segregation in the T1 generation. Albino seedlings appeared in the absence of herbicide treatment, while green seedlings continued to remain green and grew normally after the addition of 1.2 μM Shuangzuocaotong. The test results indicated that the high resistance to Shuangzuocaotong of the HPPD gene-doubled lines could be stably inherited to the T1 generation.

Example 4: An Editing Method for Knocking Up the Expression of the Endogenous PPO Gene By Inducing Chromosome Fragment Inversion—Rice Protoplast Test The rice PPO1 (also known as PPOX1) gene (as shown in SEQ ID NO: 7, in which 1-1065 bp was the promoter, the rest was the coding region) was located on chromosome 1, and the calvin cycle protein CP12 gene (as shown in SEQ ID NO: ID NO: 8, in which 1-2088 bp was the promoter, and the rest was the coding region) was located 911 kb downstream of the PPO1 gene with opposite directions. According to the rice gene expression profile data provided by the International Rice Genome Sequencing Project, the expression intensity of the CP12 gene in rice leaves was 50 times that of the PPO1 gene, and the CP12 gene promoter was a strong promoter highly expressing in leaves.

Figure 4:
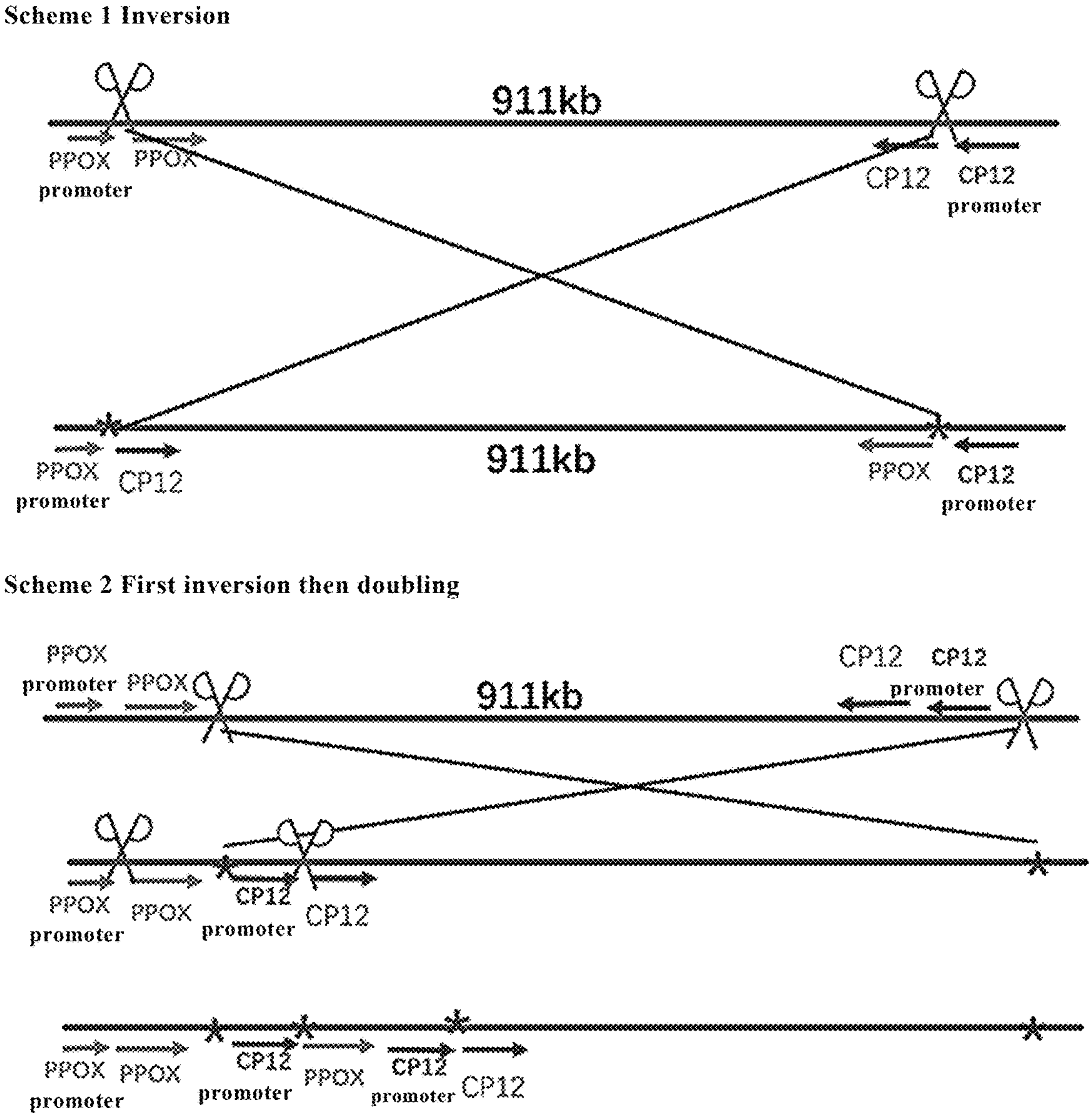
FIG. 4 shows a schematic diagram of creating a new PPOX gene in rice. PPOX is SEQ ID NO: 7. CP12 is SEQ ID NO: 8.

As shown in Scheme 1 of FIG. 4, by simultaneously inducing double-strand breaks between the respective promoters and the CDS region of the two genes and screening, the region between the two breaks could be reversed, with the promoter of PPO1 gene replaced with the promoter of CP12 gene, increasing the expression level of the PPO1 gene and achieving the resistance to PPO inhibitory herbicides, thereby herbicide-resistant lines could be selected. In addition, as shown in Scheme 2 of FIG. 4, a new gene of PPO1 driven by the promoter of CP12 gene could also be created by first inversion and then doubling.

1. First, the rice PPO1 and CP12 genomic DNA sequences were input into the CRISPOR online tool to search for available editing target sites. After online scoring, the following target sites were selected between the promoters and the CDS regions of the PPO1 and CP12 genes for testing:

| Name of target sgRNA | | Sequence (5' to 3) |
|---|---|---|
| OsPPO-guide RNA1 | SEQ ID NO: 57 | CCATGTCCGTCGCTGACGAG |
| OsPPO-guide RNA2 | SEQ ID NO: 58 | CCGCTCGTCAGCGACGGACA |
| OsPPO-guide RNA3 | SEQ ID NO: 59 | GCCATGGCTGGCTGTTGATG |
| OsPPO-guide RNA4 | SEQ ID NO: 60 | CGGATTTCTGCGTGTGATGT |

The guide RNA1 and guide RNA2 located between the promoter and the CDS region of the PPO1 gene, close to the PPO1 start codon, and the guide RNA3 and guide RNA4 located between the promoter and the CDS region of the CP12 gene, close to the CP12 start codon.

As described in Example 1, primers were designed for the above target sites to construct dual-target vectors, with pHUE411 as the backbone:

| Primer No. | | DNA sequence (5' to 3') |
|---|---|---|
| OsPPO1-sgRNA1-F | SEQ ID NO: 61 | ATATGGTCTCGGGCGCCATGTCCGTCGCTG ACGAGGTTTTAGAGCTAGAAATAGCAAG |
| OsPPO1-sgRNA2-F | SEQ ID NO: 62 | ATATGGTCTCGGGCGCCGCTCGTCAGCGAC GGACAGTTTTAGAGCTAGAAATAGCAAG |
| OsPPO1-sgRNA3-R | SEQ ID NO: 63 | TATTGGTCTCTAAACCATCAACAGCCAGCC ATGGCGCTTCTTGGTGCCGCGCCTC |
| OsPPO1-sgRNA4-R | SEQ ID NO: 64 | TATTGGTCTCTAAACACATCACACGCAGAA ATCCGGCTTCTTGGTGCCGCGCCTC |

Specifically, the pCBC-MTIT2 plasmid was used as the template to amplify the sgRNA1+3, sgRNA1+4, sgRNA2+3, sgRNA2+4 dual-target fragments and construct sgRNA expression cassettes, respectively. The pHUE411 vector backbone was digested with BsaI and recovered from gel, and the target fragment was directly used for the ligation reaction after digestion. T4 DNA ligase was used to ligate the vector backbone and the target fragment, the ligation product was transformed into Trans5a competent cells, different monoclones were selected and sequenced. The Sparkjade High Purity Plasmid Mini Extraction Kit was used to extract plasmids with correct sequencing results, thereby obtaining recombinant plasmids, respectively named as pQY002095, pQY002096, pQY002097, pQY002098, as shown below:

pQY002095 pHUE411-PPO-sgRNA1+3 containing OsPPO-guide RNA1, guide RNA3 combination pQY002096 pHUE411-PPO-sgRNA2+3 containing OsPPO-guide RNA2, guide RNA3 combination pQY002097 pHUE411-PPO-sgRNA1+4 containing OsPPO-guide RNA1, guide RNA4 combination pQY002098 pHUE411-PPO-sgRNA2+4 containing OsPPO-guide RNA2, guide RNA4 combination 2. Plasmids of high-purity and high-concentration were prepared for the above-mentioned pQY002095-002098 vectors as described in the step 2 of Example 1.
3. Rice protoplasts were prepared and subjected to PEG-mediated transformation with the above-mentioned vectors as described in step 3 of Example 1.
4. Genomic targeting and detection of new gene with the detection primers shown in the table below for the PCR detection as described in the step 4 of Example 1.

| Primer | | Sequence (5' to 3') |
|---|---|---|
| OsPPOinversion-checkF1 (PPO-F1) | SEQ ID NO: 65 | GCTATGCCGTCGCTCTTTCTC |
| OsPPOinversion-checkF2 (PPO-F2) | SEQ ID NO: 66 | CGGACTTATTCCCACCAGAA |
| OsPPOinversion-checkR1 (PPO-R1) | SEQ ID NO: 67 | GAGAAGGGGAGCAAGAAGACGT |
| OsPPOinversion-checkR2 (PPO-R2) | SEQ ID NO: 68 | AAGGCTGGAAGCTGTTGGG |
| OsCPinversion-checkF1 (CP-F1) | SEQ ID NO: 69 | CATTCCACCAAACTCCCCTCTG |
| OsCPinversion-checkF2 (CP-F2) | SEQ ID NO:70 | AGGTCTCCTTGAGCTTGTCG |
| OsCPinversion-checkR1 (CP-R1) | SEQ ID NO: 71 | GTCATCTGCTCATGTTTTCACGGTC |
| OsCPinversion-checkR2 (CP-R2) | SEQ ID NO: 72 | CTGAGGAGGCGATAAGAAACGA |

Among them, the combination of PPO-R2 and CP-R2 was used to amplify the CP12 promoter-driven PPO1 CDS new gene fragment that was generated on the right side after chromosome fragment inversion, and the combination of PPO-F2 and CP-F2 was used to amplify the PPO1 promoter-driven CP12 CDS new gene fragment that was generated on the left side after inversion. The possible genotypes resulting from the dual-target editing and the binding sites of the molecular detection primers were shown in FIG. 14.

5. The PCR and sequencing results showed that the expected new gene in which the CP12 promoter drove the expression of PPO1 was created from the transformation of rice protoplasts. The editing event where the rice CP12 gene promoter was fused to the PPO1 gene expression region could be detected in the genomic DNA of the transformed rice protoplasts. This indicated that the scheme to form a new PPO gene through chromosome fragment inversion was feasible, and a new PPO gene driven by a strong promoter could be created, which was defined as a PPO1 inversion event. The sequencing results for the chromosome fragment inversion in protoplasts transformed with the pQY002095 vector were shown in SEQ ID NO: 15; the sequencing results for the chromosome fragment deletion in protoplasts transformed with the pQY002095 vector were shown in SEQ ID NO: 16; and the sequencing results for the chromosome fragment inversion in protoplasts transformed with the pQY002098 vector were shown in SEQ ID NO: 17.

Figure 16:
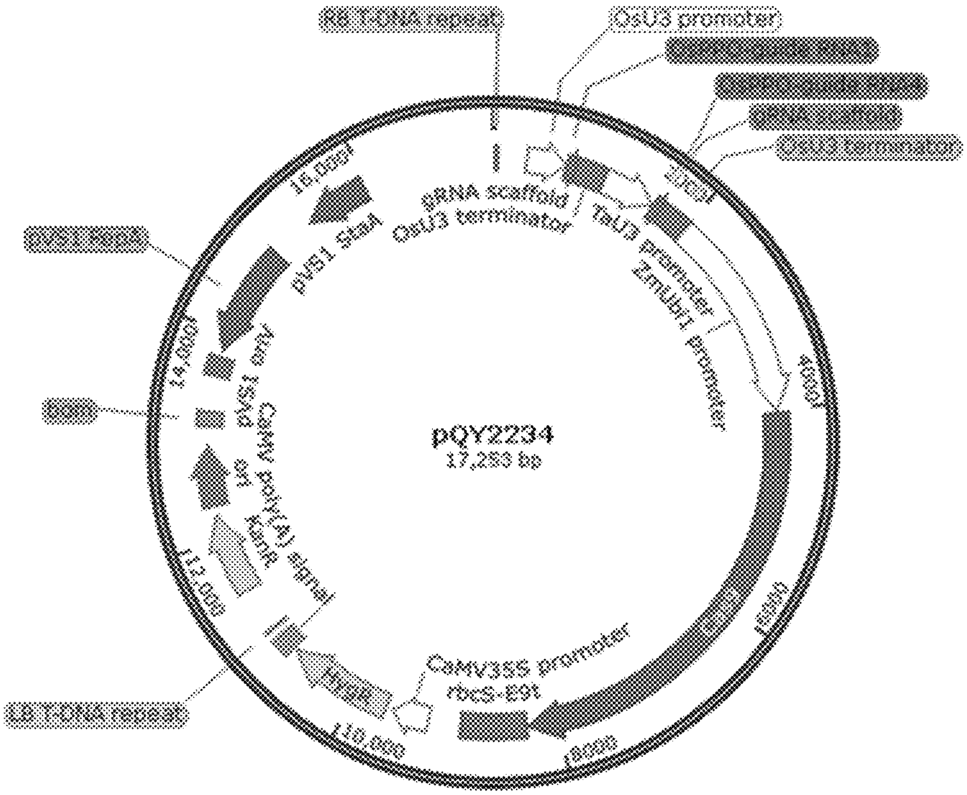
FIG. 16 shows the map of the rice *Agrobacterium* transformation vector pQY2234.
Figure 17:
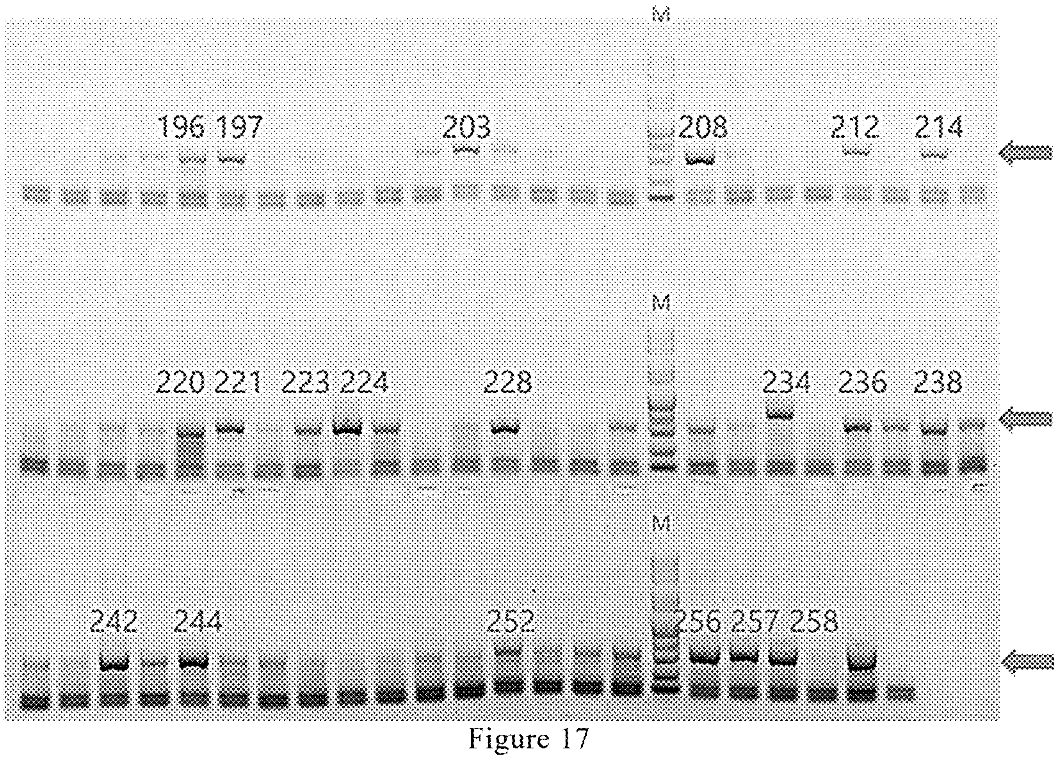
FIG. 17 shows the electrophoresis results of the PCR products for the detection of new gene fragments of hygromycin resistant rice callus transformed with pQY2234. The arrow indicates the PCR band of the new gene created by the fusion of the promoter of the CP12 gene with the coding region of the PPO1. The numbers are the serial numbers of different callus samples. M represents DNA Marker, and the band sizes are sequentially 100 bp, 250 bp, 500 bp, 750 bp, 1000 bp, 2000 bp, 2500 bp, 5000 bp, 7500 bp.

Example 5: Creation of Herbicide-Resistant Rice with Knock-Up Expression of the Endogenous PPO Gene Caused by Chromosome Fragment Inversion Through *Agrobacterium*-Mediated Transformation 1. Construction of knock-up editing vector: Based on the results of the protoplast testing, the dual-target combination of OsPPO-guide RNA1: 5'CCATGTCCGTCGCTGACGAG3' (SEQ ID NO: 57) and OsPPO-guide RNA4: 5'CGGATTTCTGCGT-GT-GATGT3' (SEQ ID NO: 60) with high editing efficiency was selected to construct the *Agrobacterium* transformation vector pQY2234. pHUE411 was used as the vector backbone and the rice codon optimization was performed. The vector map was shown in FIG. 16.
2. *Agrobacterium* transformed rice callus and two rounds of molecular identification:

The pQY2234 plasmid was used to transform rice callus according to the method described in step 2 of Example 2. The recipient varieties were Huaidao No. 5 and Jinjing 818. In the callus selection stage, two rounds of molecular identification were performed on hygromycin-resistant callus, and the calli positive in inversion event were differentiated. During the molecular detection of callus, the amplification of the CP12 promoter-driven PPO1 CDS new gene fragment generated on the right side after chromosome fragment inversion by the combination of PPO-R2 and CP-R2 was deemed as the positive standard for the inversion event, while the CP12 new gene generated on the left side after inversion was considered after differentiation and seedling emergence of the callus. A total of 734 calli from Huaidao No. 5 were tested, in which 24 calli were positive for the inversion event, and 259 calli from Jinjing 818 were tested, in which 29 calli were positive for the inversion event. FIG. 17 showed the PCR detection results of Jinjing 818 calli No. 192-259.

3. A total of 53 inversion event-positive calli were subjected to two rounds of molecular identification and then co-differentiated, and 9 doubling event-positive calli were identified, which were subjected to two rounds of molecular identification and then co-differentiated to produce 1,875 T0 seedlings, in which 768 strains were from Huaidao No. 5 background, and 1107 strains were from Jinjing 818 background. These 1875 seedlings were further subjected to the third round of molecular identification with the PPO-R2 and CP-R2 primer pair, in which 184 lines from Huaidao No. 5 background showed inversion-positive bands, 350 strains from Jinjing 818 background showed inversion-positive bands. The positive seedlings were moved to the greenhouse for cultivation.
4. PPO inhibitory herbicide resistance test of PPO1 inversion seedlings (T0 generation):

Transformation seedlings of QY2234 T0 generation identified as inversion event-positive were transplanted into large plastic buckets in the greenhouse to grow seeds of T1 generation. There were a large number of positive seedlings, so some T0 seedlings and wild-type control lines with similar growth period and status were selected. When the plant height reached about 20 cm, the herbicide resistance test was directly carried out. The herbicide used was a high-efficiency PPO inhibitory herbicide

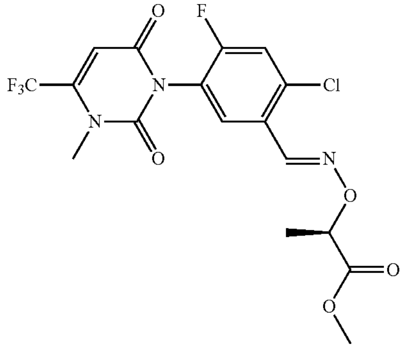 [SMILES: COC(=O)[C@@H](C)O/N=C/c1cc(-n2c(=O)cc(C(F)(F)F)n(C)c2=O)c(F)cc1Cl]

produced by the company (code 2081, see Chinse Patent Application for Invention No. 202010281666.4). In this experiment, the herbicide was applied at the gradients of three levels, namely 0.18, 0.4, and 0.6 g ai/mu, by a walk-in type spray tower.

Figure 18:
FIG. 18 shows the resistance test results of the PPO1 gene inversion strain 2081 of the QY2234 T0 generation. Under the same treatment dose, the left flowerpot is the wild-type Huaidao No. 5 control, and the right is the PPO1 inversion strain.

The resistance test results were shown in FIG. 18. 3-5 days after the application, the wild-type control rice seedlings began to wither from tip of leaf, necrotic spots appeared on the leaves, and the plants gradually withered, while most of the lines of the PPO1 inversion event maintained normal growth, the leaves had no obvious phytotoxicity. In addition, some lines showed phytotoxicity, probably due to the polygenotypic mosaicism of editing events and the low expression level of PPO1 in the T0 generation lines. Two weeks after the application, the wild-type rice seedlings died, and most of the inversion event strains continued to remain green and grew normally. The test results showed that the PPO1 inversion lines could significantly improve the tolerance of plants to 2081.

5. Quantitative detection of relative expression level of PPO1 gene in PPO1 inversion seedlings (T0 generation):

It was speculated that the increased resistance of the PPO1 gene inversion lines to 2081 was due to the fusion of the strong CP12 promoter and the CDS of the PPO1 gene which would increase the expression level of PPO1. Therefore, the lines of T0 generation QY2234-252, QY2234-304 and QY2234-329 from Huaidao No. 5 background were selected, their primary tillers and secondary tillers were sampled and subjected to the detection of expression levels of PPO1 and CP12 genes. The wild-type Huaidao No. 5 was used as the control. The specific protocols followed step 6 of Example 2, with the rice UBQ5 gene as the internal reference gene, the fluorescence quantitative primers were as follows: 5'-3'

| | | |
|---|---|---|
| UBQ5-F | SEQ ID NO: 43 | ACCACTTCGACCGCCACTACT |
| UBQ5-R | SEQ ID NO: 44 | ACGCCTAAGCCTGCTGGTT |
| RT-OsPPO1-F | SEQ ID NO: 73 | GCAGCAGATGCTCTGTCAATA |
| RT-OsPPO1-R | SEQ ID NO: 74 | CTGGAGCTCTCCGTCAATTAAG |
| RT-OsCP12-F1 | SEQ ID NO: 75 | CCGGACATCTCGGACAA |
| RT-OsCP12-R1 | SEQ ID NO: 76 | CTCAGCTCCTCCACCTC |

The UBQ5 was used as an internal reference. ΔCt was calculated by subtracting the Ct value of UBQ5 from the Ct value of the target gene. Then $2^{-\Delta Ct}$ was calculated, which represented the relative expression level of the target gene.

The H5CK1 and H5CK2 were two wild-type control plants of Huaidao No. 5, the 252M, 304M and 329M represented the primary tiller leaf samples of QY2234-252, QY2234-304 and QY2234-329 T0 plants, and the 252L, 304L, and 329L represented their secondary tiller leaf samples. The results were shown in Table 8 below:

TABLE 8

| Ct values and relative expression folds of different genes | | | | | | | | | | |
|---|---|---|---|---|---|---|---|---|---|---|
| | UBQ5 | Mean | PPO1 | ΔCt | $2^{-\Delta Ct}$ | Mean | CP12 | ΔCt | $2^{-\Delta Ct}$ | Mean |
| | 28.18 | | 25.83 | −2.43 | 5.39 | | 22.28 | −3.98 | 15.77 | |
| | 28.37 | | 25.98 | −2.28 | 4.85 | | 22.06 | −4.20 | 18.44 | |
| H5CK1 | 28.23 | 28.26 | 25.93 | −2.33 | 5.03 | 5.09 | 22.11 | −4.15 | 17.76 | 17.32 |
| | 28.23 | | 25.73 | −2.36 | 5.15 | | 21.63 | −6.47 | 88.58 | |
| | 27.98 | | 26.02 | −2.07 | 4.20 | | 21.53 | −6.57 | 94.87 | |
| H5CK2 | 28.07 | 28.09 | 25.92 | −2.18 | 4.52 | 4.62 | 21.54 | −6.55 | 93.83 | 92.43 |
| | 25.51 | | 25.17 | −0.54 | 1.45 | | 22.26 | −3.45 | 10.95 | |
| | 25.82 | | 25.22 | −0.49 | 1.41 | | 22.36 | −3.36 | 10.23 | |
| 252M | 25.80 | 25.71 | 25.22 | −0.49 | 1.41 | 1.42 | 22.43 | −3.29 | 9.76 | 10.31 |
| | 26.41 | | 23.36 | −3.14 | 8.84 | | 22.30 | −4.21 | 18.49 | |
| | 26.64 | | 23.41 | −3.10 | 8.56 | | 21.95 | −4.56 | 23.55 | |
| 252L | 26.47 | 26.51 | 23.46 | −3.05 | 8.28 | 8.56 | 21.78 | −4.73 | 26.47 | 22.84 |
| | 25.74 | | 24.55 | −1.29 | 2.44 | | 22.51 | −3.32 | 10.02 | |
| | 25.99 | | 24.53 | −1.31 | 2.48 | | 22.45 | −3.39 | 10.47 | |
| 304M | 25.78 | 25.84 | 24.48 | −1.36 | 2.57 | 2.50 | 22.56 | −3.28 | 9.71 | 10.07 |
| | 25.97 | | 23.63 | −2.36 | 5.14 | | 21.60 | −4.39 | 20.97 | |
| | 26.00 | | 23.75 | −2.25 | 4.74 | | 21.43 | −4.56 | 23.55 | |
| 304L | 26.00 | 25.99 | 23.56 | −2.43 | 5.39 | 5.09 | 22.32 | −3.68 | 12.78 | 19.10 |
| | 26.94 | | 23.11 | −3.89 | 14.84 | | 22.23 | −4.76 | 27.16 | |
| | 26.99 | | 23.25 | −3.75 | 13.42 | | 21.85 | −5.15 | 35.39 | |
| 329M | 27.07 | 27.00 | 23.22 | −3.78 | 13.71 | 13.99 | 21.82 | −5.18 | 36.29 | 32.95 |
| | 26.50 | | 23.64 | −2.63 | 6.19 | | 22.00 | −4.27 | 19.30 | |
| | 26.52 | | 23.74 | −2.53 | 5.79 | | 21.97 | −4.30 | 19.71 | |
| 329L | 25.79 | 26.27 | 23.77 | −2.50 | 5.65 | 5.87 | 22.15 | −4.12 | 17.42 | 18.81 |

Figure 19:
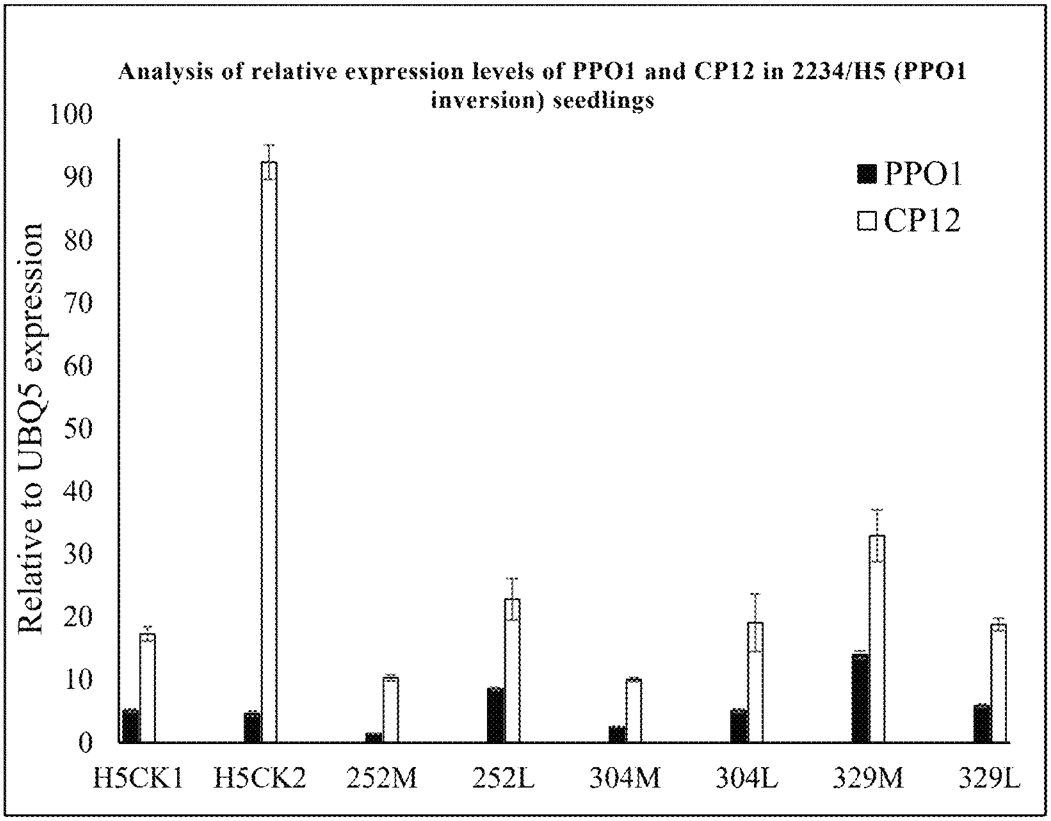
FIG. 19 shows the relative expression levels of PPO1 and CP12 genes in the QY2234 T0 generation PPO1 inversion strain. H5CK1 and H5CK2 represent two wild-type Huaidao No. 5 control plants; 252M, 304M and 329M represent the primary tiller leaf samples of QY2234-252, QY2234-304 and QY2234-329 T0 plants; 252L, 304L and 329L represent secondary tiller leaf samples.

The relative expression levels of PPO1 and CP12 in different strains were shown in FIG. 19. As the results showed, unlike the doubling event in Example 2, the gene expression levels of these inversion event strains were significantly different. The expression levels of CP12 are very different between the two Huaidao No. 5 CK groups, possibly because of the different growth rates of the seedlings. Compared with the H5CK2 control group, the expression levels of CP12 in the experimental groups all showed a tendency of decrease, while the expression levels of PPO1 for 252L and 329M increased significantly, and the expression levels of PPO1 for 304L and 329L modestly increased, and the expression levels of PPO1 for 252M and 304M decreased. Different from the doubling of chromosome fragments which mainly increased the gene expression level, the inversion of chromosome fragments generated new genes on both sides, so various editing events might occur at the targets on both sides, and the changes in the transcription direction might also affect gene expression level at the same time. That is to say, the T0 generation plants were complex chimeras. There might also be significant differences in gene expression levels between primary and secondary tillers of the same plant. It could be seen from the results of quantitative PCR that the PPO1 inversion events showed a higher likelihood of increasing the PPO1 gene expression level, and thus herbicide-resistant strains with high expression level of PPO1 could be selected out by herbicide resistance selection for the inversion events.

The above results proved that, following the scheme of detecting effective chromosome fragment inversion in protoplasts, calli and transformed seedlings with inversion events could be selected through the multiple rounds of molecular identification during the *Agrobacterium* transformation and tissue culturing, and the CP12 strong promoter fused with the new PPO1 gene generated in the transformant seedlings could indeed increase the expression level of the PPO1 gene, which could confer the plants with resistance to the PPO inhibitory herbicide 2081, thereby herbicide-resistant rice with knock-up endogenous PPO gene was created. Taking this as an example, the chromosome fragment inversion protocol of Example 4 and Example 5 also applied to other endogenous genes which gene expression pattern needed to be changed by introducing and fusing with a required promoter, thereby a new gene can be created, and new varieties with a desired gene expression pattern could be created through *Agrobacterium*-mediated transformation in plants.

Figure 14:
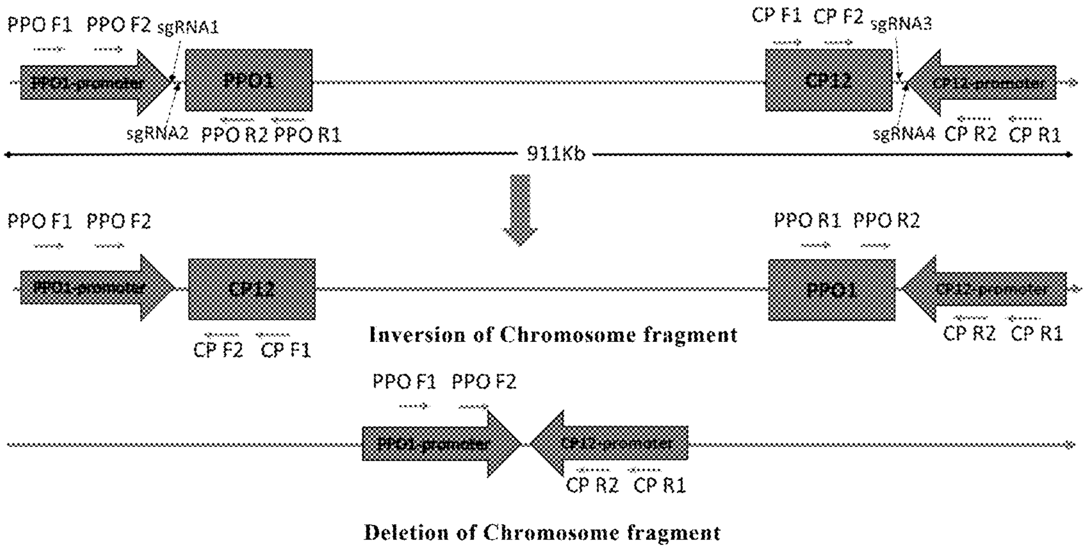
FIG. 14 shows a schematic diagram of the types of the possible editing event of rice PPO1 gene chromosome fragment inversion and the binding sites of molecular detection primers. PPO1 is SEQ ID NO: 7. CP12 is SEQ ID NO: 8.

Example 6: Molecular Detection and Herbicide Resistance Test of the T1 Generation Plants Of the Herbicide-Resistant Rice Lines with Knock-Up Expression of the Endogenous PPO1 Gene Through Chromosome Fragment Inversion The physical distance between the wild-type rice genome PPO1 gene and CP12 gene was 911 kb. As shown in FIG. 14, a highly-expressing PPO1 gene with a CP12 promoter-driven PPO1 CDS region was generated on the right side after the inversion of the chromosome fragment between the two genes. A deletion of chromosome fragment could also occur. In order to test whether the new gene could be inherited stably and the influence of the chromosome fragment inversion on genetic stability, molecular detection and herbicide resistance test was carried out on the T1 generation of the PPO1 inversion strain.

First of all, it was observed that the inversion event had no significant effect on the fertility of the T0 generation plants, as all positive T0 strains were able to produce seeds normally. The T1 generations of QY2234/H5-851 strains with the Huaidao No. 5 background were selected for detection.

1. Sample Preparation:

For QY2234/H5-851, a total of 48 T1 seedlings were planted. All the plants grew normally.

2. PCR Molecular Identification:

1) Detection primer sequence: 5'-3'

```
PPO-R2:
                                    (SEQ ID NO: 77)
AAGGCTGGAAGCTGTTGGG

CP-R2:
                                    (SEQ ID NO: 78)
CTGAGGAGGCGATAAGAAACGA

PPO-F2:
                                    (SEQ ID NO: 79)
CGGACTTATTTCCCACCAGAA

CP-F2:
                                    (SEQ ID NO: 80)
AGGTCTCCTTGAGCTTGTCG

pg-Hyg-R1:
                                    (SEQ ID NO: 55)
TCGTCCATCACAGTTTGCCA

pg-35S-F:
                                    (SEQ ID NO: 56)
TGACGTAAGGGATGACGCAC
```

2) The binding sites of the above primers were shown in FIG. 14, wherein the PPO-R2+CP-R2 was used to detect the fusion fragment of the right CP12 promoter and the PPO1 coding region after the inversion of the chromosome fragment, and the length of the product was 507 bp; the PPO-F2+CP-F2 was used to detect the fusion fragment of the left PPO1 promoter and the CP12 coding region after the inversion of the chromosome fragment, and the length of the product was 560 bp; the PPO-F2+PPO-R2 was used to detect the left PPO target site before the inversion, and the length of the product in the wild-type control was 586 bp; the CP-F2+CP-R2 was used to detect the right CP12 target site before the inversion, and the length of the product in the wild-type control was 481 bp. The pg-Hyg-R1+pg-35S-F was used to detect the T-DNA fragment of the editing vector, and the length of the product was 660 bp.

3) PCR reaction system and reaction conditions:

Reaction system (10 μL system):

| | |
|---|---|
| 2*KOD buffer | 5 μL |
| 2 mM dNTPs | 2 μL |
| KOD enzyme | 0.2 μL |
| Primer F | 0.2 μL |
| Primer R | 0.2 μL |
| Water | 2.1 μL |
| Sample | 0.3 μL |

Reaction Conditions:

| | | |
|---|---|---|
| 94° C. | 2 minutes | |
| 98° C. | 20 seconds | |
| 60° C. | 20 seconds | 40 cycles |
| 68° C. | 20 seconds | |
| 68° C. | 2 minutes | |
| 12° C. | 5 minutes | |

The PCR products were subjected to electrophoresis on a 1% agarose gel with a voltage of 180V for 10 minutes.

3. Molecular Detection Results:

The detection results were shown in Table 9. A total of 48 plants were detected, of which 12 plants (2/7/11/16/26/36/37/40/41/44/46/47) were homozygous in inversion, 21 plants (1/3/4/5/6/8/9/15/17/20/22/23/24/27/30/31/33/34/39/42/43) were heterozygous in inversion, and 15 plants (10/12/13/14/18/19/21/25/28/29/32/35/38/45/48) were homozygous in non-inversion. The ratio of homozygous inversion: heterozygous inversion:homozygous non-inversion was 1:1.75:1.25, approximately 1:2:1. So the detection results met the Mendel's law of inheritance, indicating that the new PPO1 gene generated by inversion was heritable.

TABLE 9

Results of molecular detection

| QY2234-851 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|---|---|---|---|
| Right side of inversion | + | + | + | + | + | + | + | + | + | − | + | − | − | − | + | + | + | − | − | + | + | + | + | − | + | + | − | − |
| Left side of inversion | + | + | + | + | + | + | + | + | + | − | + | − | − | − | + | + | + | − | − | + | − | + | + | + | − | + | + | − |
| PPO WT | + | − | + | + | + | + | − | + | + | + | − | + | + | + | + | − | + | + | + | + | + | + | + | + | + | − | + | + |
| CP12 WT | + | − | + | + | + | + | − | + | + | + | − | + | + | + | + | − | + | + | + | + | + | + | + | + | + | − | + | + |

| QY2234-851 | 29 | 30 | 31 | 32 | 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|---|---|---|---|---|
| Right side of inversion | + | + | − | + | + | − | + | + | − | + | + | | + | + | + | + | − | + | + | − |
| Left side of inversion | − | + | + | − | + | + | − | + | + | − | + | + | + | + | + | + | − | + | + | − |
| PPO WT | + | + | + | + | + | + | + | − | − | + | + | − | − | + | + | − | + | − | − | + |
| CP12 WT | + | + | + | + | + | + | + | − | − | + | + | − | − | + | + | − | + | − | − | + |

For the above T1 seedlings, the Pg-Hyg-R1+pg-35S-F primers were used to detect the T-DNA fragment of the editing vector. The electrophoresis results of 16 and 41 were negative for T-DNA fragment, indicating homozygous inversion. It could be seen that non-transgenic strains of homozygous inversion could be segregated from the T1 generation of the inversion event.

4. Sequencing Detection of the Editing Events:

The genotype detection of the inversion events focused on the editing events of the new PPO gene on the right side. The mutation events with the complete protein coding frame of the PPO1 gene were retained. The CP12 site editing events on the left side that did not affect the normal growth of plants through the phenotype observation in the greenhouse and field were retained. The genotypes of the editing events detected in the inversion event-positive lines were listed below, in which seamless indicated identical to the predicted fusion fragment sequence after inversion. The genotypes of the successful QY2234 inversion events in Huaidao No. 5 background were as follows:

| No. | Genotype | No. | Genotype |
|---|---|---|---|
| 2234/H5-295 | Right side −1 bp; left side −32 bp | 2234/H5-650 | Right side seamless; left side +1 bp (G) |
| 2234/H5-381 | Right side +18 bp | 2234/H5-263 | Right side seamless; left side seamless |
| 2234/H5-410 | Right side −1 bp; left side +1 bp | 2234/H5-555 | Right side −23 bp |
| 2234/H5-159 | Right side −16 bp | 2234/H5-645 | Right side −5 bp, +20 bp, |
| 2234/H5-232 | Right side −4 bp | | |

Figure 20:
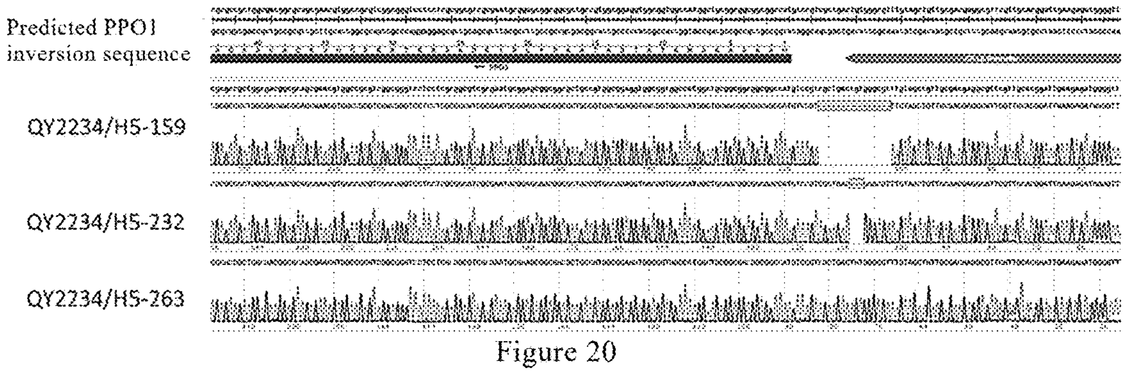
FIG. 20 shows the comparison of the sequencing result of the PPO1 inversion with the predicted inversion sequence in the Huaidao 5 background. QY2234/H5-159 is SEQ ID NO: 24. QY2234/H5-232 is SEQ ID NO: 25. QY2234/H5-263 is SEQ ID NO: 26.

Some of the sequencing peak maps and sequence comparison results were shown in FIG. 20.

The genotypes of the successful QY2234 inversion in the Jinjing818 background were as follows:

| No. | Right side PPO genotype | No. | Right side PPO genotype |
|---|---|---|---|
| 2234/818-5 | Right side seamless | 2234/818-144 | Right side +1 bp |
| 2234/818-42 | Right side −16 bp | 2234/818-151 | Sight side +2 bp, −26 bp, pure peak |
| 2234/818-108 | Right side −15 bp | 2234/818-257 | Sight side +1 bp |
| 2234/818-134 | Right side +5 bp, −15 bp | | |

Figure 21:
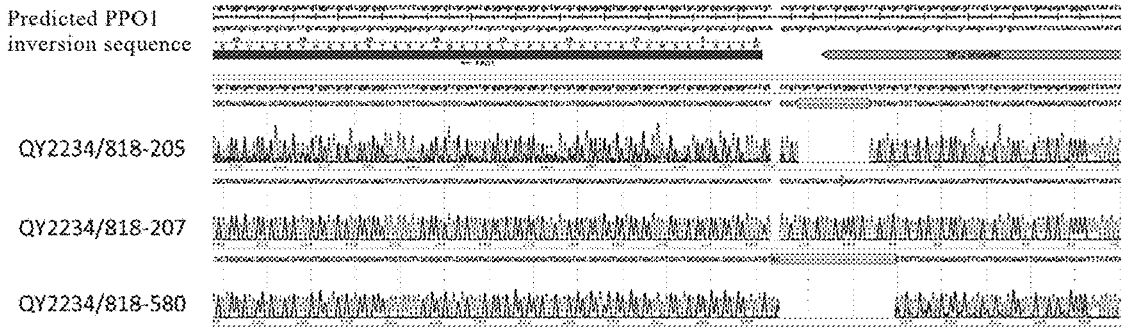
FIG. 21 shows the comparison of the sequencing result of the PPO1 inversion with the predicted inversion sequence in the Jinjing 818 background. QY2234/818-205 is SEQ ID NO: 21. QY2234/818-207 is SEQ ID NO: 22. QY2234/818-580 is SEQ ID NO: 23.

Some of the sequencing peak maps and sequence comparison results were shown in FIG. 21.

The sequencing results of the above different new PPO1 genes with the CP12 promoter fused to the PPO1 coding region were shown in SEQ ID NO: 20, SEQ ID NO: 21, SEQ ID NO: 22, SEQ ID NO: 23, SEQ ID NO: 24, SEQ ID NO: 25, and SEQ ID NO: 26.

5. Herbicide Resistance Test of T1 Generation Seedlings:

The herbicide resistance test was performed on the T1 generation of the QY2234/H5-851 PPO1 inversion lines at seedling stage. The wild-type Huaidao No. 5 was used as a control, and planted simultaneously with the T1 generation seeds of the inversion lines. When the seedlings reached a plant height of 15 cm, 2081 was applied by spraying at four levels of 0.3, 0.6, 0.9 and 1.2 g a.i./mu. The culture conditions were 28° C., with 16 hours of light and 8 hours of darkness.

Figure 22:
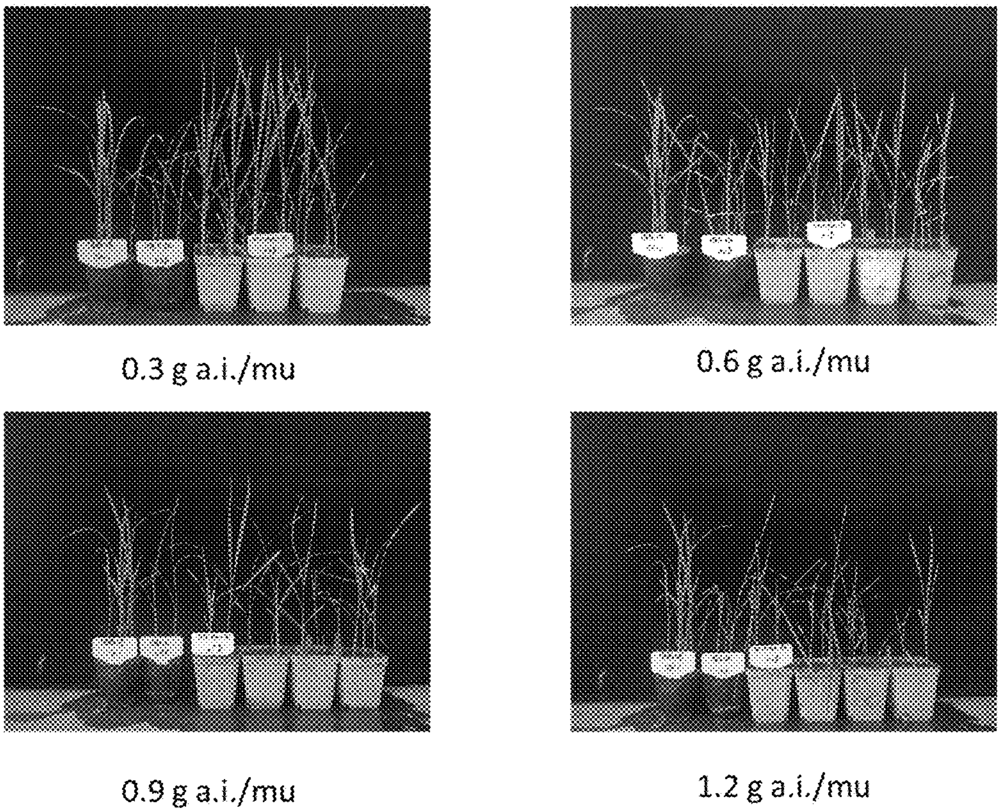
FIG. 22 shows the herbicide resistance test results for the T1 generation of the QY2234 PPO1 inversion strain at seedling stage.

The resistance test results were shown in FIG. 22. After 5 days of the application, the wild-type control rice seedlings showed obvious phytotoxicity at a dose of 0.3 g a.i./mu. They began to wither from the tip of leaf, and necrotic spots appeared on the leaves; at a dose of 0.6 g a.i./mu, the plants died quickly. However, QY2234/H5-851 T1 seedlings could maintain normal growth at a dose of 0.3 g a.i./mu, and no obvious phytotoxicity could be observed on the leaves; at doses of 0.6 and 0.9 g ai/mu, some T1 seedlings showed dry leaf tips, but most T1 seedlings could keep green and continue to grow, while the control substantially died off. At a dose of 1.2 g a.i./mu, the control plants were all dead, while some of the T1 seedlings could keep green and continue to grow. The test results indicated that the resistance of the PPO1 gene inversionlines to 2081 could be stably inherited to their T1 generation.

Example 7: An Editing Method for Knocking Up the Expression of the Endogenous EPSPS Gene in Plant EPSPS was a key enzyme in the pathway of aromatic amino acid synthesis in plants and the target site of the biocidal herbicide glyphosate. The high expression level of EPSPS gene could endow plants with resistance to glyphosate. The EPSPS gene (as shown in SEQ ID NO: 4, in which 1-1897 bp was the promoter, and the rest was the expression region) was located on chromosome 6 in rice. The gene upstream was transketolase (TKT, as shown in SEQ ID NO: 3, in which 1-2091 bp was the promoter, and the rest was the expression region) with an opposite direction. The expression intensity of TKT gene in leaves was 20-50 times that of the EPSPS gene. As shown in FIG. 2, by simultaneously inducing double-strand breaks between the promoter and the CDS region of the two genes respectively, the inversion (Scheme 1) or inversion doubling (Scheme 2) of the region between the two breaks could be obtained after screening. In both cases, the promoter of the EPSPS gene would be replaced with the promoter of the TKT gene, thereby increasing the expression level of the EPSPS gene and obtaining the resistance to glyphosate. In addition, the Schemes 3, 4 and 5 as shown in FIG. 2 could also create new EPSPS genes driven by the TKT gene promoter. The gene structure of EPSPS adjacent to and opposite in direction relative to TKT was conserved in monocotyledonous plants (Table 10). While in dicotyledonous plants, both genes were also adjacent yet in the same direction; therefore, this method was universal in plants.

TABLE 10

Distance between the EPSPS gene and the adjacent TKT gene in different plants

| Species | Location (chromosome) | Distance from CD region start site (kb) | Direction |
|---|---|---|---|
| Rice | 6 | 4 | Reverse <TKT-EPSPS> |
| Wheat | 7A | 35 | Reverse <TKT-EPSPS> |
| | 7D | 15 | Reverse <TKT-EPSPS> |
| | 4A? | 50 | Reverse <TKT-EPSPS> |
| Maize | 9 | 22 | Reverse <TKT-EPSPS> |
| *Brachypodium distachyon* | 1 | 5 | Reverse <TKT-EPSPS> |
| Sorghum | 10 | 15 | Reverse <TKT-EPSPS> |
| Millet | 4 | 5 | Reverse <TKT-EPSPS> |
| Soybean | 3 | 6 | Forward TKT>EPSPS> |

TABLE 10-continued

| Distance between the EPSPS gene and the adjacent TKT gene in different plants | | | |
|---|---|---|---|
| Species | Location (chromosome) | Distance from CD region start site (kb) | Direction |
| Tomato | 5 | 6 | Forward TKT>EPSPS> |
| Peanut | 2 | 6 | Forward TKT>EPSPS> |
| | 12 | 5 | Forward TKT>EPSPS> |
| Cotton | 9 | 22 | Forward TKT>EPSPS> |
| Alfalfa | 4 | 8 | Forward TKT>EPSPS> |
| *Arabidopsis* | 2 | 5 | Forward TKT>EPSPS> |
| Grape | 15 | 17 | Forward TKT>EPSPS> |

To this end, pHUE411 was used as the backbone, and the following as targets:

| Name of target sgRNA | | Sequence (5' to 3) |
|---|---|---|
| OsEPSPS-guide RNA1 | SEQ ID NO: 81 | CCACACCACTCCTCTCGCCA |
| OsEPSPS-guide RNA2 | SEQ ID NO: 82 | CCATGGCGAGAGGAGTGGTG |
| OsEPSPS-guide RNA3 | SEQ ID NO: 83 | ATGGTCGCCGCCATTGCCGG |
| OsEPSPS-guide RNA4 | SEQ ID NO: 84 | GACCTCCACGCCGCCGGCAA |
| OsEPSPS-guide RNA5 | SEQ ID NO: 85 | TAGTCATGTGACCATCCCTG |
| OsEPSPS-guide RNA6 | SEQ ID NO: 86 | TTGACTCTTTGGTTCATGCT |

Several different dual-target vectors had been constructed:

$$pQY002061pHUE411-EPSPS-sgRNA1+3$$

$$pQY002062pHUE411-EPSPS-sgRNA2+3$$

$$pQY002063pHUE411-EPSPS-sgRNA1+4$$

$$pQY002064pHUE411-EPSPS-sgRNA2+4$$

$$pQY002093pHUE411-EPSPS-sgRNA2+5$$

$$pQY002094pHUE411-EPSPS-sgRNA2+6$$

(2) With the relevant detection primers shown in the following table, the fragments containing the target sites on both sides or the predicated fragments generated by the fusion of the UBI2 promoter and the HPPD coding region were amplified, and the length of the products is between 300-1000 bp.

| Primer | | Sequence (5' to 3') |
|---|---|---|
| EPSPSinversion checkF1 | SEQ ID NO: 87 | ATCCAAGTTACCCCCTCTGC |
| EPSPSinversion checkR1 | SEQ ID NO: 88 | CACAAACACAGCCACCTCAC |
| EPSPSinversion check-nestF2 | SEQ ID NO: 89 | ATGTCCACGTCCACACCATA |

-continued

| Primer | | Sequence (5' to 3') |
|---|---|---|
| EPSPSinversion check-nestR2 | SEQ ID NO: 90 | AATGGAATTCACGCAAGAGG |
| EPSPSinversion checkF3 | SEQ ID NO: 91 | GTAGGGGTTCTTGGGGTTGT |
| EPSPSinversion checkR3 | SEQ ID NO: 92 | CGCATGCTAACTTGAGACGA |
| EPSPSinversion check-nestF4 | SEQ ID NO: 93 | GGATCGTGTTCACCGACTTC |
| EPSPSinversion check-nestR4 | SEQ ID NO: 94 | CCGGTACAACGCACGAGTAT |
| EPSPSinversion checkF5 | SEQ ID NO: 95 | GGCGTCATTCCATGGTTGATT GT |
| EPSPSinversion checknestF6 | SEQ ID NO: 96 | GATAGACCCAGATGGGCATA GAATC |
| EPSPSinversion checkR5 | SEQ ID NO: 97 | TGCATGCATTGATGGTTGGTG C |
| EPSPSinversion checknestR6 | SEQ ID NO: 98 | CCGGCCCTTAGAATAAAGGT AGTAG |

After protoplast transformation, the detection results showed that the expected inversion events were obtained. As shown in FIG. 15, the sequencing result of the inversion detection of pQY002062 vector transformed protoplast was shown in SEQ ID NO: 11; the sequencing result of the deletion detection of pQY002062 vector transformed protoplast was shown in SEQ ID No: 12; the sequencing result of the inversion detection of the pQY002093 vector transformed protoplast was shown in SEQ ID NO: 13; and the sequencing result of the deletion detection of pQY002093 vector transformed protoplast was shown in SEQ ID NO: 14.

These vectors were transferred into *Agrobacterium* for transforming calli of rice. Plants containing the new EPSPS gene were obtained. The herbicide bioassay results showed that the plants had obvious resistance to glyphosate herbicide.

Example 8: An Editing Method for Knocking Up the Expression of the Endogenous PPO Gene in *Arabidopsis*

Protoporphyrinogen oxidase (PPO) was one of the main targets of herbicides. By highly expressing plant endogenous PPO, the resistance to PPO inhibitory herbicides could be significantly increased. The *Arabidopsis* PPO gene (as shown in SEQ ID NO: 1, in which 1-2058 bp was the promoter, and the rest was the expression region) located on chromosome 4, and the ubiquitin10 gene (as shown in SEQ ID NO: 2, in which 1-2078 bp was the promoter, and the rest was the expression region) located 1.9M downstream with the same direction as the PPO gene.

Figure 3:
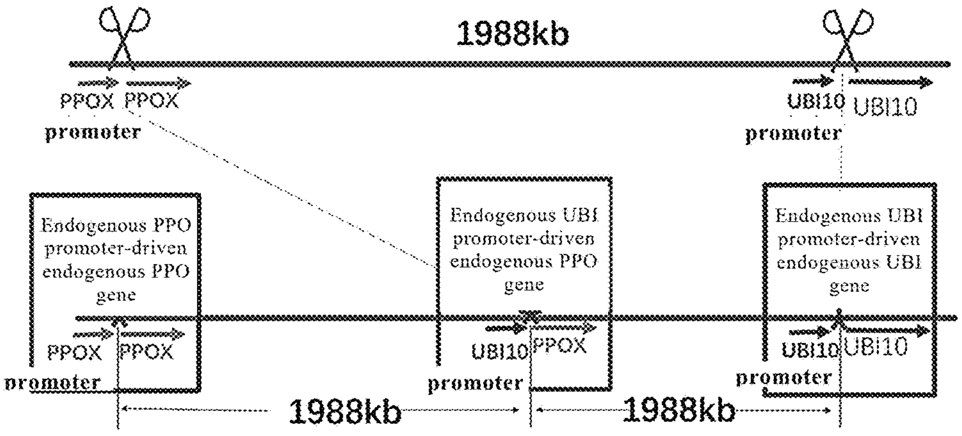
FIG. 3 shows a schematic diagram of creating a new PPOX gene in *Arabidopsis thaliana*. PPOX is SEQ ID NO: 1. UBI10 is SEQ ID NO: 2.

As shown in the Scheme as shown in FIG. 3, simultaneously generating double-strand breaks at the sites between the promoter and the CDS region of the PPO and the ubiquitin10 genes respectively. Doubling events of the region between the two breaks could be obtained by screening, namely a new gene generated by fusing the ubiquitin10 promoter and the PPO coding region. In addition, following Scheme 2 as shown in FIG. 1, a new gene in which the ubiquitin10 promoter and the PPO coding region were fused together could also be created.

To this end, pHEE401E was used as the backbone, and the following locations were used as target sites:

| Name of target sgRNA | | Sequence (5' to 3) |
|---|---|---|
| AtPPO-guide RNA1 | SEQ ID NO: 99 | CAAACCAAAGAAAAAGTATA |
| AtPPO-guide RNA2 | SEQ ID NO: 100 | GGTAATCTTCTTCAGAAGAA |
| AtPPO-guide RNA3 | SEQ ID NO: 101 | ATCATCTTAATTCTCGATTA |
| AtPPO-guide RNA4 | SEQ ID NO: 102 | TTGTGATTTCTATCTAGATC |

The dual-target vectors were constructed following the method described by "Wang Z P, Xing H L, Dong L, Zhang H Y, Han C Y, Wang X C, Chen Q J. Egg cell-specific promoter-controlled CRISPR/Cas9 efficiently generates homozygous mutants for multiple target genes in *Arabidopsis* in a single generation. Genome Biol. 2015 Jul. 21; 16:144.":

| | |
|---|---|
| pQY002076 | pHEE401E-AtPPO-sgRNA1 + 3 |
| pQY002077 | pHEE401E-AtPPO-sgRNA1 + 4 |
| pQY002078 | pHEE401E-AtPPO-sgRNA2 + 3 |
| pQY002079 | pHEE401E-AtPPO-sgRNA2 + 4 |

*Arabidopsis* was transformed according to the method as follows:

(1) *Agrobacterium* Transformation

*Agrobacterium* GV3101 competent cells were transformed with the recombinant plasmids to obtain recombinant *Agrobacterium.*

(2) Preparation of *Agrobacterium* Infection Solution

1) Activated *Agrobacterium* was inoculated in 30 ml of YEP liquid medium (containing 25 mg/L Rif and 50 mg/L Kan), cultured at 28° C. under shaking at 200 rpm overnight until the OD600 value was about 1.0-1.5.
2) The bacteria were collected by centrifugation at 6000 rpm for 10 minutes, and the supernatant was discarded.
3) The bacteria was resuspended in the infection solution (no need to adjust the pH) to reach OD600-0.8 for later use.

(3) Transformation of *Arabidopsis*

1) Before the plant transformation, the plants should grow well with luxuriant inflorescence and no stress response. The first transformation could be carried out as long as the plant height reached 20 cm. When the soil was dry, watering was carried out as appropriate. On the day before the transformation, the grown siliques were cut with scissors.
2) The inflorescence of the plant to be transformed was immersed in the above solution for 30 seconds to 1 minute with gentle stirring. The infiltrated plant should have a layer of liquid film thereon.
3) After transformation, the plant was cultured in the dark for 24 hours, and then removed to a normal light environment for growth.
4) After one week, the second transformation was carried out in the same way.

(4) Seed Harvest

Seeds were harvested when they were mature. The harvested seeds were dried in an oven at 37° C. for about one week.

(5) Selection of Transgenic Plants

The seeds were treated with disinfectant for 5 minutes, washed with $ddH_2O$ for 5 times, and then evenly spread on MS selection medium (containing 30 μg/ml Hyg, 100 μg/ml Cef). Then the medium was placed in a light incubator (at a temperature of 22° C., 16 hours of light and 8 hours of darkness, light intensity 100-150 $\mu mol/m^2/s$, and a humidity of 75%) for cultivation. The positive seedlings were selected and transplanted to the soil after one week.

(6) Detection of T1 Mutant Plants (6.1) Genomic DNA Extraction

1) About 200 mg of *Arabidopsis* leaves was cut and placed into a 2 ml centrifuge tube. Steel balls were added, and the leaves were ground with a high-throughput tissue disruptor.
2) After thorough grinding, 400 μL of SDS extraction buffer was added and mixed upside down. The mixture was incubated in a 65° C. water bath for 15 minutes, and mixed upside down every 5 minutes during the period.
3) The mixture was centrifuged at 13000 rpm for 5 minutes.
4) 300 μL of supernatant was removed and transferred to a new 1.5 ml centrifuge tube, an equal volume of isopropanol pre-cooled at −20° C. was added into the centrifuge tube, and then the centrifuge tube was kept at −20° C. for 1 hour or overnight.
5) The mixture was centrifuged at 13000 rpm for 10 minutes, and the supernatant was discarded.
6) 500 μL of 70% ethanol was added to the centrifuge tube to wash the precipitate, the washing solution was discarded after centrifugation (carefully not discarding the precipitate). After the precipitate was dried at room temperature, 30 μL of $ddH_2O$ was added to dissolve the DNA, and then stored at −20° C.

(6.2) PCR Amplification

With the extracted genome of the T1 plant as template, the target fragment was amplified with the detection primers. 5 μL of the amplification product was taken and detected by 1% agarose gel electrophoresis, and then imaged by a gel imager. The remaining product was directly sequenced by a sequencing company.

The sequencing results showed that the AtPPO1 gene doubling was successfully achieved in *Arabidopsis*, and the herbicide resistance test showed that the doubling plant had resistance to PPO herbicides.

Example 9: Creation of GH1 Gene with New Expression Characteristics in Zebrafish The growth hormone (GH) genes in fishes controlled their growth and development speed. At present, highly expressing the GH gene in Atlantic salmons through the transgenic technology could significantly increase their growth rates. The technique was of great economical value, but only approved for marketing after decades. The GH1 gene was the growth hormone gene in zebrafish. In the present invention, suitable promoters in zebrafish (suitable in terms of continuous expression, strength, and tissue specificity) were fused together in vivo through deletion, inversion, doubling, inversion doubling, chromosome transfer, etc., to create a fast-growing fish variety.

All publications and patent applications mentioned in the description are incorporated herein by reference, as if each publication or patent application is individually and specifically incorporated herein by reference.

Although the foregoing invention has been described in more detail by way of examples and embodiments for clear understanding, it is obvious that certain changes and modifications can be implemented within the scope of the appended claims, such changes and modifications are all within the scope of the present invention.

What is claimed is:

1. A method for creating a new gene in a plant, comprising the following steps:

simultaneously generating DNA breaks at two or more different specific sites in the plant's genome by delivering a CRISPR-based gene editing system into a cell of the plant which targets the two or more different specific sites of the genomic DNA, wherein the CRISPR-based gene editing system comprises a nuclease or a polynucleotide encoding thereof, and two or more guide RNAs which target the two or more different specific sites respectively or one or more polynucleotide encoding the guide RNAs, wherein the nuclease and the guide RNAs contact the two or more different specific sites and creates cleavage at the two or more different specific sites, and wherein the specific sites are genomic sites separating different genetic elements, wherein the genetic element is selected from a group consisting of a promoter, a 5' untranslated region, a coding region (CDS), a region encoding a non-coding RNA, a 3' untranslated region, and a terminator of the gene, providing a condition allowing the DNA breaks to be ligated to each other by a non-homologous end joining (NHEJ), detecting a new combination of the different genetic elements different from the original genomic sequence, wherein the combination of different genetic elements is a combination of a promoter of a first gene and a coding region of a second gene, wherein the two genes have different expression patterns, wherein the transcription of the second gene is driven by the promoter of the first gene, wherein the promoter of the first gene and the coding region of the second gene have nucleotide sequences selected from:

(1) the promoter of the first gene is a promoter of CP12 gene, wherein the CP12 gene comprises a nucleotide sequence of SEQ ID NO: 8, and the coding region of the second gene is a coding region of PPO gene, wherein the PPO gene comprises a nucleotide sequence of SEQ ID NO: 7;

(2) the promoter of the first gene is a promoter of Ubiquitin gene, wherein the Ubiquitin gene comprises a nucleotide sequence of SEQ ID NO: 2, and the coding region of the second gene is a coding region of PPO gene, wherein the PPO gene comprises a nucleotide sequence of SEQ ID NO: 1;

(3) the promoter of the first gene is a promoter of UBI2 gene, wherein the UBI2 gene comprises a nucleotide sequence of SEQ ID NO: 5, and the coding region of the second gene is a coding region of HPPD gene, wherein the HPPD gene comprises a nucleotide sequence of SEQ ID NO: 6; and (4) the promoter of the first gene is a promoter of TKT gene, wherein the TKT gene comprises a nucleotide sequence of SEQ ID NO: 3, and the coding region of the second gene is a coding region of EPSPS gene, wherein the EPSPS gene comprises a nucleotide sequence of SEQ ID NO: 4, the new gene is created if the new combination of the different genetic elements is detected, wherein the new gene improves the resistance or tolerance to an herbicide, wherein the method does not involve the provision of a foreign DNA template.

2. The method according to claim 1, characterized in that said DNA breaks are achieved by delivering a nuclease with targeting property into a cell of the plant to contact with the specific sites of the genomic DNA.

3. The method according to claim 2, characterized in that said nuclease with targeting property is selected from the group consisting of Meganuclease, Zinc finger nuclease, TALEN, and CRISPR/Cas system.

4. The method according to claim 2, characterized in that the nucleases with targeting property are delivered into the cell by: 1) a PEG-mediated cell transfection method; 2) a liposome-mediated cell transfection method; 3) an electric shock transformation method; 4) a microinjection; 5) a gene gun bombardment; or 6) an *Agrobacterium*-mediated transformation method.

5. An editing method for increasing the gene expression level of a target endogenous gene in a plant, which is independent of an exogenous DNA donor fragment, by creating a new highly-expressing endogenous gene in the plant according to the method in claim 1, comprising the following steps:

simultaneously generating DNA breaks separately at selected sites between the promoter and the coding region of each of the target endogenous gene and an endogenous highly-expressing gene; ligating the DNA breaks to each other by means of non-homologous end joining (NHEJ), thereby generating an in vivo fusion of the coding region of the target endogenous gene and the strong endogenous promoter to form the new highly-expressing endogenous gene, wherein the promoter of the endogenous highly-expressing gene and the coding region of the target endogenous gene have nucleotide sequences selected from:

(1) the promoter of the endogenous highly-expressing gene is a promoter of CP12 gene, wherein the CP12 gene comprises a nucleotide sequence of SEQ ID NO: 8, and the coding region of the target endogenous gene is a coding region of PPO gene, wherein the PPO gene comprises a nucleotide sequence of SEQ ID NO: 7;

(2) the promoter of the endogenous highly-expressing gene is a promoter of Ubiquitin gene, wherein the Ubiquitin gene comprises a nucleotide sequence of SEQ ID NO: 2, and the coding region of the target endogenous gene is a coding region of PPO gene, wherein the PPO gene comprises a nucleotide sequence of SEQ ID NO: 1;

(3) the promoter of the endogenous highly-expressing gene is a promoter of UBI2 gene, wherein the UBI2 gene comprises a nucleotide sequence of SEQ ID NO: 5, and the coding region of the target endogenous gene is a coding region of HPPD gene, wherein the HPPD gene comprises a nucleotide sequence of SEQ ID NO: 6; and (4) the promoter of the endogenous highly-expressing gene is a promoter of TKT gene, wherein the TKT gene comprises a nucleotide sequence of SEQ ID NO: 3, and the coding region of the target endogenous gene is a coding region of EPSPS gene, wherein the EPSPS gene comprises a nucleotide sequence of SEQ ID NO: 4, wherein the target endogenous gene and the endogenous highly-expressing gene are located on the same chromosome.

6. An editing method for knocking up the expression of an endogenous HPPD, EPSPS or PPO gene in a plant by creating a new highly-expressing plant endogenous HPPD, EPSPS or PPO gene in the plant according to the method in claim 1, characterized in that it comprises fusing the coding region of the HPPD, EPSPS or PPO gene with a strong endogenous promoter of a plant in vivo to form the new highly-expressing plant endogenous HPPD, EPSPS or PPO gene, respectively; wherein the method comprises the following steps: simultaneously generating DNA breaks respectively in selected specific sites between the promoter and the coding region of each of the HPPD, EPSPS or PPO gene and an optional endogenous highly-expressing gene, ligating the DNA breaks to each other through an intracellular repair pathway, generating in vivo a fusion of the coding region of the HPPD, EPSPS or PPO gene and the optional strong endogenous promoter to form the new highly-expressing HPPD, EPSPS or PPO gene, respectively.

7. The method according to claim 1, characterized in that said two or more different specific sites locate on the same chromosome, wherein said at least two different genes may have the same or different transcription directions.

8. The method according to claim 2, characterized in that the nuclease with targeting property" is in the form of DNA, or exists in the form of mRNA or protein, but not DNA.

9. The method of claim 1, characterized in that, in the new combination of the different genetic elements, the promoter of the first gene is a promoter of CP12 gene, wherein the CP12 gene comprises a nucleotide sequence of SEQ ID NO: 8, and the coding region of the second gene is a coding region of PPO gene, wherein the PPO gene comprises a nucleotide sequence of SEQ ID NO: 7; or the promoter of the first gene is a promoter of Ubiquitin gene, wherein the Ubiquitin gene comprises a nucleotide sequence of SEQ ID NO: 2, and the coding region of the second gene is a coding region of PPO gene, wherein the PPO gene comprises a nucleotide sequence of SEQ ID NO: 1; wherein an expression level of the PPO gene in a genome comprising the new combination is higher than an expression level of the PPO gene in a wild-type genome.

10. A new gene obtainable by the method according to claim 1, characterized in that compared with the original gene, the new gene either has a different promoter and therefore is expressed with a different spatial-temporal characteristics or a different intensity characteristics or a different developmental stage characteristics.

11. The editing method according to claim 6, characterized in that it comprises fusing the coding region of the HPPD gene with a strong endogenous promoter of a rice, wherein the strong promoter is a promoter of ubiquitin2 gene, it comprises fusing the coding region of the EPSPS gene with a strong endogenous promoter of a rice, wherein the strong promoter is a promoter of TKT gene, or it comprises fusing the coding region of the PPO gene with a strong endogenous promoter of a rice or an *Arabidopsis*, wherein in rice, the strong promoter is a promoter of CP12 gene, and in *Arabidopsis*, the strong promoter is a promoter of ubiquitin10 gene.

12. A highly-expressing plant endogenous HPPD, EPSPS or PPO gene obtainable by the editing method according to claim 6.

13. A method for producing a plant with an increased resistance or tolerance to an herbicide, which comprises regenerating the plant host cell into a plant and a progeny derived therefrom, wherein the plant host cell comprises the expression cassette comprising the gene according to claim 12.

14. A method for controlling a weed in a cultivation site of a plant, wherein the plant is selected from the group consisting of a plant prepared by the method according to claim 13, wherein the method comprises applying to the cultivation site one or more of HPPD, EPSPS or PPO inhibitory herbicides in an amount for effectively controlling the weed.

* * * * *

SEQUENCE LISTING

<160> NUMBER OF SEQ ID NOS: 102

<210> SEQ ID NO 1
<211> LENGTH: 4439
<212> TYPE: DNA
<213> ORGANISM: Arabidopsis thaliana
<220> FEATURE:
<221> NAME/KEY: gene
<222> LOCATION: (1)..(4439)
<223> OTHER INFORMATION: Arabidopsis thaliana PPO gene(Genbank number AT4G01690 sequence)

<400> SEQUENCE: 1

```
gatattttga tgtcgtatgt atatcaatgt tgttagctgt aaactgtcca atgaaaatcc     60
atttaatatt tggacaaatt attattaggg aaattaatgt aatgtggagt attttatatg    120
aaatgtgtat taatgacgac gaccttactt gatcccggaa gtgtgtatta atttaatcgc    180
ggtgcatcgc tgtccacacg gttgggttca tgcgtacgtg gtatttgctg gcaagtggca    240
gtgaagtttc ttgtttgata ctgtatgttc cattcatgtc tttccctaga tgcatgtttc    300
ttctattttt atatattaat attttttttgt ttttcttatt atgttttctt tccctttgtg    360
aggagaataa ttgcgatacg attatttgtt ttaacagaaa aaagtgaagc gaaaaagatg    420
attcgaagtt tgaagtacga ttaaaatttt tctttttccg gatccgagtt tgatcttctt    480
tagaaacaaa aattatattt gtttagaaag tctgtcagtt gggttttggc ccaattgatt    540
tacctggtag tcagaaatgt aagtgacctg actacccttg acattagtca gaaaacattc    600
taaactcgag ataaacactg tggtagttct ttagaaagaa gtcgactcta aagtactttg    660
gcgtaaaaca aaaaaatttc ccttgaaatt atactttatt tgtttgacat aaatgtttca    720
aatataatct tcttttaatc aatgtagtta aattttttttg atagaagcac gtcagaattt    780
cacactagta atgtataagt ggtaatcatc attgcctaaa acaatgatta attaaaattt    840
tagaattcgt cgtcgacaaa gaatttttct tatgatgaag gttttgtgca taattatgaa    900
cggatccatt tatttcactc taactaggaa tagatgtttg atgggataca agtgaacacg    960
acacaaagta acaaaaaattc atttaacgtc acaaattatt ctcaatcgaa tttcgaagta   1020
tcaagaaaaa gggcaattaa aaacgtaatc tcattatgtc tttgaaatct aaattaaaag   1080
ttgagtttat tttaattatt aatttccttt ttgatgatgt aggggatgac aattgacaac   1140
caatttgatt tgaaagatta acataaatca ttttgagcat acatatattg cttaaatcac   1200
acccgtttat ctctaaaaac ctccataatt tatatcagga aaataaatct agttattgat   1260
atcgccatca aatatttttt tcttaaattg tttttttttg ttgttgttga aaatttaatt   1320
agaaagataa gtggacaacg acgcgagaca aagacacaat ctttagggcc ttgagtaaat   1380
tagggacagc ataaacacat gcactagtcc tgtctttatt taattatgtg gtgtttactc   1440
taatgacgtc gctttgatta accaagtggt cataattaat atatcgatcg aattatataa   1500
ttatcataaa tttgaataag catgttgcct tttattaaag aggtttaata aagtttggta   1560
ataatggact ttgacttcaa actcgattct catgtaatta attaatattt acatcaaaat   1620
ttggtcacta atattaccaa attaatatac taaaatgtta attcgcaaat aaaacactaa   1680
ttccaaataa agggtcatta tgataaacac gtattgaact tgataaagca aagcaaaaat   1740
aatgggtttc aaggtttggt tatatatgac aaaaaaaaaa aaaggtttgg ttatatatct   1800
attgggccta taaccatgtt ataacaaatt tgggcctaac taaaataata aaataaacgt   1860
aatggtcctt tttatatttg ggtcaaaccc aactctaaac ccaaaccaaa gaaaaagtat   1920
```

-continued

```
acggtacggt acacagactt atggtgtgtg tgattgcagg tgaatatttc tcgtcgtctt   1980
ctcctttctt ctgaagaaga ttacccaatc tgaaaaaaac caagaagctg acaaaattcc   2040
gaattctctg cgatttccat ggagttatct cttctccgtc cgacgactca atcgcttctt   2100
ccgtcgtttt cgaagcccaa tctccgatta aatgtttata agcctcttag actccgttgt   2160
tcagtggccg gtggaccaac cgtcggatct tcaaaaatcg aaggcggagg aggcaccacc   2220
atcacgacgg attgtgtgat tgtcggcgga ggtattagtg gtctttgcat cgctcaggcg   2280
cttgctacta agcatcctga tgctgctccg aatttaattg tgaccgaggc taaggatcgt   2340
gttggaggca acattatcac tcgtgaagag aatggttttc tctgggaaga aggtcccaat   2400
agttttcaac cgtctgatcc tatgctcact atggtggtaa gttcttgaaa caatctgatt   2460
cgttaatact gagaacaatg tatttgtgaa ttgtttgatt tgtggattta gccttctctg   2520
tttatggtta gagtaggtag atagtggttt gaaggatgat ttggtgttgg gagatcctac   2580
tgcgccaagg tttgtgttgt ggaatgggaa attgaggccg gttccatcga agctaacaga   2640
cttaccgttc tttgatttga tgagtattgg tgggaagatt agagctggtt ttggtgcact   2700
tggcattcga ccgtcacctc cagtgtgtat tcttacgacc ttttagatca atatgatttt   2760
tagggcttta tgttggtaga atctgctcat gttcttagag tttggcaaag gtgacagggt   2820
cgtgaagaat ctgtggagga gtttgtacgg cgtaacctcg gtgatgaggt tttgagcgc    2880
ctgattgaac cgttttgttc aggtagagtt atagataaaa cttcatgtga accatttatt   2940
catttagatg tcagcgaatc tgattatcta gcagttttca tttttgttct agtgcaccct   3000
taatgcttta gattttatgc ttttaggtgt ttatgctggt gatccttcaa aactgagcat   3060
gaaagcagcg tttgggaagg tttggaaact agagcaaaat ggtggaagca taataggtgg   3120
tacttttaag gcaattcagg agaggaaaaa cgctcccaag gcagaacgag acccgtgagt   3180
aacatcaaac ttttctgttg cttgggtctt ttgtcccttc atatatatat ttgtaaaaca   3240
actcaacctg cttcttcagg cgcctgccaa aaccacaggg ccaaacagtt ggttctttca   3300
ggaagggact tcgaatgttg ccagaagcaa tatctgcaag gtatccagta cttgtctctc   3360
tctattgttg gaagggaaaa gggaaaaact ttcaaatgtt ttctgaaatc ttttgcactt   3420
tgacagatta ggtagcaaag ttaagttgtc ttggaagctc tcaggtatca ctaagctgga   3480
gagcggagga tacaacttaa catatgagac tccagatggt ttagtttccg tgcagagcaa   3540
aagtgttgta atgacggtgc catctcatgt tgcaagtggt ctcttgcgcc ctctttctgt   3600
aagtttctca ttttgcgaac taggaatttg ctcaaaattc atagattcga caaatatggg   3660
ttcttaaatc gtgtgctgca actgttatct tctcaggaat ctgctgcaaa tgcactctca   3720
aaactatatt acccaccagt tgcagcagta tctatctcgt acccgaaaga agcaatccga   3780
acagaatgtt tgatagatgg tgaactaaag ggttttgggc aattgcatcc acgcacgcaa   3840
ggagttgaaa cattaggtat atatcttgta gttataatcg tcaattatgt caaaatgttc   3900
atagaatctt catgctgttg ctcgtatttc ttcaggaact atctacagct cctcactctt   3960
tccaaatcgc gcaccgcccg gaagaatttt gctgttgaac tacattggcg ggtctacaaa   4020
caccggaatt ctgtccaagg taaaaaacag caaacacttg taacacatct ttattcaacc   4080
aagtaaacct aagaactgat agttttcttc tctctctctc ttttgttttg attccgcagt   4140
ctgaaggtga gttagtggaa gcagttgaca gagatttgag gaaaatgcta attaagccta   4200
attcgaccga tccacttaaa ttaggagtta gggtatggcc tcaagccatt cctcagtttc   4260
tagttggtca ctttgatatc cttgacacgg ctaaatcatc tctaacgtct tcgggctacg   4320
```

aagggctatt tttgggtggc aattacgtcg ctggtgtagc cttaggccgg tgtgtagaag 4380
gcgcatatga aaccgcgatt gaggtcaaca acttcatgtc acggtacgct tacaagtaa 4439

<210> SEQ ID NO 2
<211> LENGTH: 3452
<212> TYPE: DNA
<213> ORGANISM: Arabidopsis thaliana
<220> FEATURE:
<221> NAME/KEY: gene
<222> LOCATION: (1)..(3452)
<223> OTHER INFORMATION: Arabidopsis thaliana Ubiquitin10 gene(Genbank number AT4G05320 sequence)

<400> SEQUENCE: 2
aaacaagact accaatatga tgaactgatg attttttttt ttttttttt ggctcaacaa 60 caaactttcc attcacccat ttatggatac acagtctagc tcaacagagc ttttaaccca 120
aattggtaca atagaataca actttagatc ataattctca aaagaaagag attccttagc 180
tattctatct gccactccat ttccttctcg gcttgtatgc acaagcataa aatcctcaaa 240
cttgctaagt agatacttta tgtcttggat aattggattg agacttgaca agcataactt 300
tcatgtaacc aaagacacaa gttgctgaga atccacctca aaaatgatct tcctataatt 360
gaatcgggat aatgacagca cagcccatct aagagcctcc acttctactt ccagcacgct 420
tcttactttt accacagctc ttgcacctaa ccataacacc ttccctgtat gatcgcgaag 480
cacccaccct aagccacatt ttaatccttc tgttggccat gccccatcaa agttgcactt 540
aacccaagat tgtggtggag cttcccatgt ttctcgtctg tcccgacggt gttgtggttg 600
gtgctttcct tacattctga gcctctttcc ttctaatcca ctcatctgca tcttcttgtg 660
tccttactaa tacctcattg gttccaaatt ccctcccttt aagcaccagc tcgtttctgt 720
tcttccacag cctcccaagt atccaaggga ctaaagcctc cacattcttc agatcaggat 780
attcttgttt aagatgttga actctatgga ggtttgtatg aactgatgat ctaggaccgg 840
ataagttccc ttcttcatag cgaacttatt caaagaatgt tttgtgtatc attcttgtta 900
cattgttatt aatgaaaaaa tattattggt cattggactg aacacgagtg ttaaatatgg 960
accaggcccc aaataagatc cattgatata tgaattaaat aacaagaata aatcgagtca 1020
ccaaaccact tgcctttttt aacgagactt gttcaccaac ttgatacaaa agtcattatc 1080
ctatgcaaat caataatcat acaaaaatat ccaataacac taaaaaatta aaagaaatgg 1140
ataatttcac aatatgttat acgataaaga agttactttt ccaagaaatt cactgatttt 1200
ataagcccac ttgcattaga taaatggcaa aaaaaaacaa aaaggaaaag aaataaagca 1260
cgaagaattc tagaaaatac gaaatacgct tcaatgcagt gggacccacg gttcaattat 1320
tgccaatttt cagctccacc gtatatttaa aaaataaaac gataatgcta aaaaaatata 1380
aatcgtaacg atcgttaaat ctcaacggct ggatcttatg acgaccgtta gaaattgtgg 1440
ttgtcgacga gtcagtaata aacggcgtca aagtggttgc agccggcaca cacgagtcgt 1500
gtttatcaac tcaaagcaca aatacttttc ctcaacctaa aaataaggca attagccaaa 1560
aacaactttg cgtgtaaaca acgctcaata cacgtgtcat tttattatta gctattgctt 1620
caccgcctta gctttctcgt gacctagtcg tcctcgtctt ttcttcttct tcttctataa 1680
aacaataccc aaagagctct tcttcttcac aattcagatt tcaatttctc aaaatcttaa 1740
aaactttctc tcaattctct ctaccgtgat caaggtaaat ttctgtgttc cttattctct 1800
caaaatcttc gattttgttt tcgttcgatc ccaatttcgt atatgttctt tggtttagat 1860

-continued

```
tctgttaatc ttagatcgaa gacgattttc tgggtttgat cgttagatat catcttaatt   1920

ctcgattagg gtttcataga tatcatccga tttgttcaaa taatttgagt tttgtcgaat   1980

aattactctt cgatttgtga tttctatcta gatctggtgt tagtttctag tttgtgcgat   2040

cgaatttgtc gattaatctg agtttttctg attaacagat gcagatcttt gttaagactc   2100

tcaccggaaa gacaatcacc ctcgaggtgg aaagctccga caccatcgac aacgttaagg   2160

ccaagatcca ggataaggag ggcattcctc cggatcagca gaggcttatt ttcgccggca   2220

agcagctaga ggatggccgt acgttggctg attacaatat ccagaaggaa tccaccctcc   2280

acttggtcct caggctccgt ggtggtatgc agattttcgt taaaacccta acgggaaaga   2340

cgattactct tgaggtggag agttctgaca ccatcgacaa cgtcaaggcc aagatccaag   2400

acaaagaggg tattcctccg gaccagcaga ggctgatctt cgccggaaag cagttggagg   2460

atggcagaac tcttgctgac tacaatatcc agaaggagtc cacccttcat cttgttctca   2520

ggctccgtgg tggtatgcag attttcgtta agacgttgac tgggaaaact atcactttgg   2580

aggtggagag ttctgacacc attgataacg tgaaagccaa gatccaagac aaagagggta   2640

ttcctccgga ccagcagaga ttgatcttcg ccggaaaaca acttgaagat ggcagaactt   2700

tggccgacta caacattcag aaggagtcca cactccactt ggtcttgcgt ctgcgtggag   2760

gtatgcagat cttcgtgaag actctcaccg gaaagaccat cactttggag gtggagagtt   2820

ctgacaccat tgataacgtg aaagccaaga tccaggacaa agagggtatc ccaccggacc   2880

agcagagatt gatcttcgcc ggaaagcaac ttgaagatgg aagaactttg gctgactaca   2940

acattcagaa ggagtccaca cttcacttgg tcttgcgtct gcgtggaggt atgcagatct   3000

tcgtgaagac tctcaccgga aagactatca ctttggaggt agagagctct gacaccattg   3060

acaacgtgaa ggccaagatc caggataagg aaggaatccc tccggaccag cagaggttga   3120

tctttgccgg aaaacaattg gaggatggtc gtactttggc ggattacaac atccagaagg   3180

agtcgaccct tcacttggtg ttgcgtctgc gtggaggtat gcagatcttc gtcaagactt   3240

tgaccggaaa gaccatcacc cttgaagtgg aaagctccga caccattgac aacgtcaagg   3300

ccaagatcca ggacaaggaa ggtattcctc cggaccagca gcgtctcatc ttcgctggaa   3360

agcagcttga ggatggacgt actttggccg actacaacat ccagaaggag tctactcttc   3420

acttggtcct gcgtcttcgt ggtggtttct aa                                 3452
```

<210> SEQ ID NO 3
<211> LENGTH: 5159
<212> TYPE: DNA
<213> ORGANISM: Oryza sativa
<220> FEATURE:
<221> NAME/KEY: gene
<222> LOCATION: (1)..(5159)
<223> OTHER INFORMATION: Sequence of rice transketolase(TKT)
gene(GenBank number LOC4340025)

<400> SEQUENCE: 3

```
catgaaccaa agagtcaaat tcaagatggc gtgctgctct tggtcttttg aatgtggcag     60

cagccaggat caatgcatcc taatatatct atgttggctt agtgaatgac taattaaaca    120

caattaaccc cagggatggt cacatgacta ctgatctctt caaactgttt taatttccca    180

tgtcagaatc tacatctgta cgtacaattt aagctctcct ttttttttt ttaaaaaaaa    240

aagacgaggt taaactaact aactaagctt gagcatcttc taatgtagta aggtatataa    300

atcagaagca aaaacaacat caaaactgtt acaaaaacaa gcaaaccata taaataagaa    360
```

-continued

```
tattccacaa aggtagattc ctgctgaata gattctatgc ccatctgggt ctatcttgtt    420
atttattctc gtgtggctcg gtttcatcat ccatcttggc gaatcacaga aaagagcggt    480
ttgcaattta tatttggttg aaaagaatgg caattttaca tgccaggatc atatacctct    540
gcatctaaaa agttgatttt tttgacccca aattttcaac ataaacatca caatcaacca    600
tggaatgacg ccagaaaaca actgtgacgg cgacgacccc aacatacaca aggagccagg    660
acaatcttta cattattttt atctcttaga aaaaaatatg tcccataaca attttttttt    720
caaaaggctc accagaccac taacaaatag gcgaaaatat ctttaataat atccaatcgt    780
ttcctaccct cttccaacgg ccaggatcat cttgtttgcc atatcaacgg tcatggctga    840
tatcctcatc caccaaccca cctcaccaca cccatcccca cataaaccca gtccatacac    900
gcaaatctaa tcaaaaccac atgtatagct gcagaatata tataacaatt ctatcatata    960
tacatactac aaacttgcac tttattattc caagaattga taccatttcc agcatctttt   1020
ttaaacctaa ctgtagaatt ttgtgaaagc tacaaaatca gtcaggtcaa tgttcatgta   1080
aaacgaacta attctcatca gattagtgtg ctataaacat aagcaaaata tataaagaaa   1140
ttagtaagat cactcctcta tgtgaatatt ttcacacctt tgccaaatat gcataaattt   1200
tttatccaag atgttgcata tacttcctcc gtttcacaat gtaagtcact ctagcatttt   1260
ccacatttat attgatgtta acgaatctag acagtctaga ttcgtgtcta gcttcattaa   1320
catcaatatg aatgtgggaa atgctagaat gacttacatt gtgaaacgga gggagtactt   1380
acctaggtta acatttgtta agtttttttt attgtgtcat attttcatca tttgttgata   1440
atgctatact ttcttttcag tatagactat gtaagtaagt agctatagct tctgttaaaa   1500
caaatgtcag gttttatcta ttatctaaaa acatccaagt tacccccctct gcttcatatt   1560
ataagtcgtt tatttttttc ctaatcaaat attgttaatt tcgacaaaat ttatagaaaa   1620
aattaacaac atctaagata ttaaattagt tttattaaat ctaagttgta tatattttga   1680
taatatgatt gttgtgttga aaatactaat atatttttct acatatttag ttaaacttaa   1740
aaaaagtttg ataaaatttt tttaaaggat ttataatata aaaggaggga gtaacatttg   1800
ttaactacaa tataaaaact aatttaaaga tcaaataagt acaataacta ctttataaag   1860
attataggtt caataattgc ggcgaagaaa gtgctcctaa tctcaccagc catggcggct   1920
taggatgctg gtccatgcac catgtccacg tccacaccat agccccctcc tttttattgg   1980
ctacgagtcc ccccaaaacg cacccccaag tctatacata acccatccca tctcccaccc   2040
cacaacctcg ccatctccgc ctctcctcgc caccacacca ctcctctcgc catggccgcg   2100
cactccgtcg ccgccgcgca cgccaccatc gccgcgcgcg cgggtgccgc cgcgccagcg   2160
cccgcgccgc cggagcgcct cgggttccgc ctcagcgcgc tcgccggccg cggcctccgc   2220
tccccgctcc cgcctcgccg cggcgcgcca tcggcgtccg cgtcgcgccg ccgccacaac   2280
aaccgcgtgc gcgcggcggc ggtcgagacg ctcgaggggc aggcggcgac gggggcgctg   2340
ctcgagaagt cggtgaacac gatccggttc ctcgccatcg acgccgtcga gaaggccaac   2400
tcggggcacc ccggcctgcc catggggtgc gcgcccatgg ggcacatcct ctacgacgag   2460
gtcatgcggt acaaccccaa gaacccctac tggttcaacc gcgaccgctt catcctctcc   2520
gccggccacg gctgcatgct ccagtacgcc ctgctccacc tcgccggcta cgacgccgtc   2580
ttggtaagcg cttcccatat ccctttgctc cttgcatctc tctttcgctt ctcgagttgg   2640
ttggtttggg gcggataaat cgggagtagg ttcgtgcaag tttcggatct tgttaggtga   2700
```

-continued

```
agcagtggaa agtgtggatc ttgactgcta tttttgtgtg gcggcttcgt tttttttccta   2760
gtaaaagtgt gcaccttttc cagtcgtcag agatctgttt agtggaattt aatcttatgt   2820
aatacttcct aggaagatta gttggaagat gctattaagt cgagcaattg ttcactgtaa   2880
attctggagt gatcggtgaa gtgtttaata tggttgactt cagtttcaac tgatttgttc   2940
atcgagcttg ctgtaactat ggccgcatat tgctgcagga ggaggacttg aagcaattca   3000
ggcaatgggg aagcaagact ccaggccatc ccgagaactt cgagacgccc ggagttgaag   3060
ttaccactgg tctgtcatct caactgaagc tcatagcacc tttaagtttc tatgcttgaa   3120
tacatacaga actgaatgtt tcggtttctt gtttggtttc gttctgtagg acctcttggt   3180
cagggtattg caaatgcagt tgggctggcc cttgctgaga agcacctggc tgctcgtttc   3240
aacaagcccg acagcgagat tgttgatcac tacacgtaat ttttttttta tcatgaatac   3300
ctttagtttt cactttagtt atggtggtgc aaccttggta acatgattca tggattttgt   3360
gcagctactg tattttggga gatgggtgcc agatggaggg tatctccaat gaagcttgct   3420
cgttggctgg ccattggggt cttggcaagc tgattgcatt ctatgatgac aaccacattt   3480
ccattgacgg agacacagag attgcattca ctgaggatgt gagtgctcgc tttgaggctc   3540
ttgggtggca tacaatctgg gttaagaatg gaaacgatgg ctatgatgag attcgtgccg   3600
ccattaagga agcaaaggcg gtaactgaca agccaacact aatcaaggtt agattcctgt   3660
acattctgtt atgctgtgtt ttgttataga gcttatcata tttagccaaa atgtactctt   3720
tttaggtgac caccacaatc ggttttggat cacccaacaa ggccaactca tacagcgtcc   3780
acggaagtgc tttgggtacc aaagaggttg aagcaaccag agagaacctt ggatggccct   3840
atgagccatt ctttgtgcct gaggatgtga agaggtttgt ctattgttgt tttggttatc   3900
tgaatgagat gttgaaattt catagcactc accttatggt ttatttgcat gggctgttac   3960
agccactgga gccgccatgt gcctcaaggt gctgcttttg aggctgactg gaatgctaag   4020
ttcgccgagt atgagaagaa gtacccagaa gatgcagcga ccttgaagag cattgtctca   4080
ggggagttgc ctgctggctg ggctgacgct cttcctgtaa gtcttttacc atttctactc   4140
ataacatttg agctggtatg tgaatgatga cattctaatg gtagattact tgatttgtac   4200
agaaatacac tccagagagc cctgcagatg ccaccaggaa tctgtcacag cagtgcttaa   4260
acgcacttgc taaagttgtt cctggtcttc ttggaggaag tgctgatctt gcatcctcca   4320
acatgacatt gcttaagatg ttcggtgact tccagaagga tacgcctgag gagcgcaatg   4380
tccgatttgg agtcagggag catggaatgg gcgccatttg caacggcatt gctctgcaca   4440
gcccaggact cattccatac tgtgctactt tctttgtttt cactgattac atgagagctg   4500
ccatgaggat ctcagccttg tgtgaagccg gagttatcta tgttatgacc catgactcta   4560
ttggtcttgg agaagatggt ccaacccatc agcccattga gcacttggtg agcttccgtg   4620
cgatgcccaa cattctgatg cttcgtcctg ctgatggtaa cgagactgct ggggcataca   4680
aaatcgcggt cctcaacagg aagaggccat ccgtccttgc tctctccagg caaaagcttg   4740
ctcagctgcc tggtacctcg attgagggtg ttgagaaggg tgggtacatc gtctctgaca   4800
actcaactgg caacaagcct gacttcattg tgatgagcac tggctctgaa ctagagattg   4860
tcgccaaggc tgctgatgag ttgaggaagg aggggaagac tgtccgtgtc gtgtcatttg   4920
tttgctggga gcttttcgat gaacagtcgg ctgagtacaa ggagagtgtt ctccctgagg   4980
ctgttactgc aagagtcagc cttgaagcag ggtctactct tggatggcag aagtacgtcg   5040
gaagcaaagg caaggctatt ggcatcgaca aattcggtgc aagtgctcct gctggaaaga   5100
```

-continued tctaccagga gtatggcatc accgcggaga acgtcatcgc aacagcaaag agcctgtaa 5159

<210> SEQ ID NO 4
<211> LENGTH: 5164
<212> TYPE: DNA
<213> ORGANISM: Oryza sativa
<220> FEATURE:
<221> NAME/KEY: gene
<222> LOCATION: (1)..(5164)
<223> OTHER INFORMATION: Rice EPSPS gene (GenBank number LOC4340026)

<400> SEQUENCE: 4
gctgggtagc ctttcaaagc cccaaaagat tgggtcgggt ctctctttcg gctctcgtcg 60
gtggctgctt cccacaaaga ccgccatcag acgtgaatga actgcaagtc tgcaactacg 120
actccagttg ctatcccctt aaattacttt actactacct ttattctaag ggccggttcg 180
gataattgcc aaaatcaatc gtaccaaatt ttaataatat taggatgaaa taaatatgtt 240
gcgccaaaat tttctactgt tactgaaatt tggtaacaaa ctaaacacaa ccgtatattt 300
atcaatttta ccaaatagtg gtatggttta aaatgacatt aatctaaata ggtcctgaaa 360
tataaaaatg caccaaccat caatgcatgc agttacattc caaagttctc ctaggacaca 420
tatgccatat attttcgatg gatagcctta atgtctgact actctcttca tcgcaacaaa 480
tctaatataa tacaaatctg aataggagct tatataaata tatagtagta gaatatgtca 540
taatattaca gtggtattcc atattggatt tgttgattat agaacgacga aagtatgcgt 600
taacttacaa ggttgtttac attatgacga aatgaagaga aggaacgcac ctactgcgaa 660
gagctcaaca actacttcct ccaaatttcc actcaccaac tgatcaccac caattcactt 720
gtgcagtgcc acctacccaa tttcattcca gtggcgtggt acgtaggttc cgcatgtcag 780
tgtgacaatc gtacggactg ccatgtgtat tgtgttcagg taggtgcact ggtcgtggtc 840
tcaccatctc tcctccagtc gtacggcgcc acgtaggcag tacacgtaga cggccttctt 900
cctcctccct cgagttgagt tggttggtga gagtgagaca ccgacggaac ggaaggagaa 960
ccacgccgct tggatttttc ttttttacct tttcaaattt taatttaaaa aataaaacca 1020
ttttaaaaac ttatcttcaa atacaaatct tttaaaaaca ctaacacgtg acacacagcg 1080
ggcacgtcac ccaaacgggc gtgacaatat tgttttgcca caccaatcca gctggtgtgg 1140
acaaaatgtt catatattga aaataaaatt taaaacaatt tatatttttt atctatatca 1200
ttataaaaat tgaagatgtt tttaccggta ttttgttact catttgtgca tgagtcggtt 1260
tttaagtttg ttcgcttttg gaaatacata tccgtatttg agtatgtttt taagttcgtt 1320 cgtttttttga aatacaaaag gaatcgtaaa ataaatctat tttaaaaaac tcgcatgcta 1380
acttgagacg atcgaactgc taattgcagc tcataatttt ccaaaaaaaa atatatccaa 1440
acgagttctt atagtagatt tcaccttaat taaaacatat aaatgttcac ccggtacaac 1500
gcacgagtat ttttataagt aaaattaaaa gtttaaaata aataaaaatc ccgccaccac 1560
ggcgcgatgg taaaaggggg acgcttctaa acgggccggg cacgggacga tcggccccga 1620
acccggccca tctaaccgct gtaggcccac cgcccaccaa tccaactccg tactacgtga 1680
agcgctggat ccgcaacccg ttaagcagtc cacacgactc gactcgactc gcgcactcgc 1740
cgtggtaggt ggcaaccctt cttcctcctc tatttcttct tcttcctccc ttctccgcct 1800
caccacacca accgcaccaa ccccaacccc gcgcgcgctc tcccctctcc cctcccacca 1860
accccacccc atcctcccga cctccacgcc gccggcaatg gcggcgacca tggcgtccaa 1920

-continued

```
cgccgcggct gcggcggcgg tgtccctgga ccaggccgtg gcggcgtcgg cggcgttctc   1980
gtcgcggaag cagctgcggc tgcccgccgc ggcgcgcggg gggatgcggg tgcgggtgcg   2040
ggcgcggggg cggcgggagg cggtggtggt ggcgtccgcg tcgtcgtcgt cggtggcagc   2100
gccggcggcg aaggcggagg agatcgtgct ccagcccatc agggagatct ccggggcggt   2160
tcagctgcca gggtccaagt cgctctccaa caggatcctc ctcctctccg ccctctccga   2220
ggtgagacgc ggatcccttc ctcttgcgtg aattccattt ctggagatga gattttaggg   2280
ggtttattag gtgaggtggc tgtgtttgtg aaatcctagg aattatctct caagtcaatc   2340
taacgatgag atataactga ggttctggtt ttaatcacac actcatataa ccaatttatt   2400
gaaacatttt ggtttggcat aagaaactgc ttacgaaggt atgatatcct cctacatgtc   2460
aggctactaa attttcacga cggtatgatc cactcaaaac aagtttctta acgagtctgg   2520
tgaggtctgt tatgaaattt gtgtaaacta aggcaacttt ggaggtttcg cactgtacca   2580
atgttatgtt tgaacatttt gcaagcagtg ctttctccca aaattatgca attttgaggc   2640
tcctctacat cattataatt ccccaataca ttgctcttta ttcttaatag ctttgatcgc   2700
gaaatttaac attttaattc ttgagctgtt attttgtagc atcagtttat catgagccat   2760
gtttggtact aaatatacaa tcccttgggt ttatttgttt ccaagcatgt cattaactta   2820
tcttaatgtg gacaagaaac tgatgcctgc ttacattgct attatttcaa gcgggtattg   2880
atcctttgac atgtgattga tcattttttt ttctctggtt attagggcac aacagtggtg   2940
gacaacttgc tgaacagtga ggatgttcac tacatgcttg aggccctgaa agccctcggg   3000
ctctctgtgg aagcagataa agttgcaaaa agagctgtag tcgttggctg tggtggcaag   3060
tttcctgttg agaaggatgc gaaagaggaa gtgcaactct tcttggggaa cgctggaact   3120
gcaatgcgac cattgacagc agccgtgact gctgctggtg gaaatgcaac gtatgttttt   3180
tttttaatg tttatgaaaa tatgtatgga attcatgggg tatgttttat gacctttttc    3240
tttaccatca gttatgtgct tgatggagtg ccacgaatga gggagagacc gattggtgac   3300
ttggttgtcg ggttgaaaca acttggtgcg gatgtcgact gtttccttgg cactgaatgc   3360
ccacctgttc gtgtcaaggg aattggagga cttcctggtg gcaaggttag ttactcctaa   3420
actgcatcct ttgtacttct gtatgcacct caattctttg tcaaccttct gcatttataa   3480
ggaacattct atgatgcaat tcgaccttac actgcacagt aacttgaaat gtttcatgct   3540
taatcaatat gccatattcc tgccaagctc aagcgagcaa tatttgtttg aatttggtac   3600
catatttttg tatatttggg cattcctttt tggtcttgat gtcttctttt gaattagcat   3660
ttaactgaat tacactcaac aggttaagct ctctggttcc atcagcagtc agtacttgag   3720
tgccttgctg atggctgctc ctttggccct tggggatgtg gagatcgaaa tcattgacaa   3780
actaatctcc attccttacg ttgaaatgac attgagattg atggagcgtt ttggtgtgaa   3840
ggcagagcat tctgatagtt gggacagatt ctatattaag ggagggcaga agtacaagta   3900
agcttctacc tgccttactg agctgaatta ttcgggtgtt tatgattaac tccctaaact   3960
aacccttttt cttttctttg gcattgacag atctcctgga aatgcctatg ttgaaggtga   4020
tgcctcaagc gcgagctatt tcttggctgg tgctgcaatc actggaggca ctgtgacagt   4080
tcaaggttgt ggtacgacca gtttgcaggt ataactgtag tgcctgtttt gacattctac   4140
cgtttagtca agtttagtca gtagtcacat attcagaata tagcacaatc tgtattatgc   4200
cactgttaat caaatacgct tgacctagag agtgctatat accctagctt aatcttcaaa   4260
ctaaacagtt ctcttgtggc ttgctgtgct gttatgttcc ctgacctaca tgttaatatt   4320
```

-continued acagggtgat gtcaaatttg ctgaggtact tgagatgatg ggagcaaagg ttacatggac 4380
tgacaccagt gtaaccgtaa ctggtccacc acgtgagcct tatgggaaga aacacctgaa 4440
agctgttgat gtcaacatga acaaaatgcc tgatgttgcc atgacccttg ccgttgttgc 4500
actcttcgct gatggtccaa ctgctatcag agatggtaaa cattaaggcc tattatacct 4560
gttctatcat actagcaatt actgcttagc attgtgacaa aacaaataac caaactttct 4620
tcaaaataac ttagaaatat aagaaaggtt cgttttgtgt ggtaaacagt actactgtag 4680
tttcagctat gaagtttgct gctggcaatt ttctgaacgg tttcagctaa attgcatgtt 4740
tgttcatcat acttatccat tgtcttccac agtggcttcc tggagagtaa aggaaaccga 4800
aaggatggtt gcaattcgga ccgagctaac aaaggtaaat tcattaggtc ccgtgtcctt 4860
tcattcttca agtagtttgt tcataagttg aattctcctt caatgatgtt taaattcatc 4920
atcttctttt ttggtgttgt gccagctggg agcatcggtt gaagaaggtc ctgactactg 4980
catcatcacc ccaccggaga agctgaacat cacggcaatc gacacctacg atgatcacag 5040
gatggccatg gccttctccc tcgctgcctg cgccgacgtg cccgtgacga tcagggaccc 5100
tggttgcacc cgcaagacct tccccaacta cttcgacgtt ctaagcactt tcgtcaggaa 5160
ctga 5164

<210> SEQ ID NO 5
<211> LENGTH: 3481
<212> TYPE: DNA
<213> ORGANISM: Oryza sativa
<220> FEATURE:
<221> NAME/KEY: gene
<222> LOCATION: (1)..(3481)
<223> OTHER INFORMATION: Rice ubiquitin2 gene(GenBank number LOC4328390)

<400> SEQUENCE: 5
gaaatcaaaa gggaaatgca ccatcttata tctccagttt atatgaacag attggataag 60
atcataagat caagtggttt atattatttt gaggaatata acatggattc atcctaatca 120
ctcgtctagg cagtatgtgt attcatgatg gatatggtac tatactacgg agttttttct 180
tcacaaaata acctgttatt ttgacctcca accaaacacg aattatacca aaaattgggt 240
tatttcatct atagtacaac tctattataa acatgcagta aattatccta cacatatacc 300
aaaattcaag tgtaataatc ctaatacaca gacttaaaaa acaaactatt tcctttttaa 360
gaaaaggaaa accatttttt taacggaagg aaaacaaatt cgggtcaagg cggaagccag 420
cgcgccaccc cacgtcagca aatacggagg cgcggggttg acggcgtcac ccggtcctaa 480
cggcgaccaa caaaccagcc agaagaaatt acagtaaaaa aaaagtaaat tgcactttga 540
tccacctttt attacctaag tctcaatttg gatcaccctt aaacctatct tttcaatttg 600
ggccgggttg tggtttggac taccatgaac aacttttcgt catgtctaac ttccctttca 660
gcaaacatat gaaccatata tagaggagat cggccgtata ctagagctga tgtgtttaag 720
gtcgttgatt gcacgagaaa aaaaaatcca aatcgcaaca atagcaaatt tatctggttc 780
aaagtgaaaa gatatgttta aaggtagtcc aaagtaaaac ttatagataa taaaatgtgg 840
tccaaagcgt aattcactca aaaaaaatca acgagacgtg taccaaacgg agacaaacgg 900
catcttctcg aaatttccca accgctcgct cgcccgcctc gtcttcccgg aaaccgcggt 960
ggtttcagcg tggcggattc tccaagcaga cggagacgtc acggcacggg actcctccca 1020
ccacccaacc gccataaata ccagccccct catctcctct cctcgcatca gctccacccc 1080

-continued

```
cgaaaaattt ctccccaatc tcgcgaggct ctcgtcgtcg aatcgaatcc tctcgcgtcc   1140
tcaaggtacg ctgcttctcc tctcctcgct tcgtttcgat tcgatttcgg acgggtgagg   1200
ttgttttgtt gctagatccg attggtggtt agggttgtcg atgtgattat cgtgagatgt   1260
ttaggggttg tagatctgat ggttgtgatt tgggcacggt tggttcgata ggtggaatcg   1320
tggttaggtt ttgggattgg atgttggttc tgatgattgg ggggaatttt tacggttaga   1380
tgaattgttg gatgattcga ttggggaaat cggtgtagat ctgttgggga attgtggaac   1440
tagtcatgcc tgagtgattg gtgcgatttg tagcgtgttc catcttgtag gccttgttgc   1500
gagcatgttc agatctactg ttccgctctt gattgagtta ttggtgccat gggttggtgc   1560
aaacacaggc tttaatatgt tatatctgtt ttgtgtttga tgtagatctg tagggtagtt   1620
cttcttagac atggttcaat tatgtagctt gtgcgtttcg atttgatttc atatgttcac   1680
agattagata atgatgaact cttttaatta attgtcaatg gtaaatagga agtcttgtcg   1740
ctatatctgt cataatgatc tcatgttact atctgccagt aatttatgct aagaactata   1800
ttagaatatc atgttacaat ctgtagtaat atcatgttac aatctgtagt tcatctatat   1860
aatctattgt ggtaatttct ttttactatc tgtgtgaaga ttattgccac tagttcattc   1920
tacttatttc tgaagttcag gatacgtgtg ctgttactac ctatctgaat acatgtgtga   1980
tgtgcctgtt actatctttt tgaatacatg tatgttctgt tggaatatgt ttgctgtttg   2040
atccgttgtt gtgtccttaa tcttgtgcta gttcttaccc tatctgtttg gtgattattt   2100
cttgcagatg cagatctttg tgaagacatt gaccggcaag actatcaccc tcgaggtgga   2160
gtcctctgac accatcgata atgtcaaggc taagatccaa gataaggagg gcatcccccc   2220
ggaccagcag cgtctcatct tcgctggcaa gcagctggag gatggcagga cccttgctga   2280
ctacaacatc cagaaggagt cgacccttca ccttgtcctc cgcctccgtg gtggcatgca   2340
gatctttgtc aagactctga ccggcaagac tatcaccctt gaggtggagt cttctgacac   2400
catcgacaac gtcaaggcca agatccagga caaagagggc atcccccccag accagcagcg   2460
tctcatcttc gccggcaagc agctggagga tggcaggacc cttgctgact acaacatcca   2520
gaaggagtcc accctccacc ttgtcctccg cctccgtggt ggcatgcaga tctttgtcaa   2580
gacactgacc ggcaagacca tcaccctcga ggtggaatct tctgacacca tcgacaacgt   2640
caaggccaag atccaggaca aggagggcat tcccccggac cagcagcgtc tcatctttgc   2700
cggcaagcag cttgaggacg gcaggaccct tgctgactac aacatccaga aggagtcaac   2760
gcttcacctt gtcctccgtc tcaggggagg catgcaaatc ttcgtgaaga ctctgaccgg   2820
caagaccatc accctcgagg tggagtcttc tgataccatc gacaatgtca aggccaagat   2880
ccaggacaag gagggcattc cccggacca gcagcgcctc atctttgctg gcaagcagct   2940
ggaggatggc aggacccttg ctgactacaa catccagaag gagtccaccc tccaccttgt   3000
gctccgcctt cgtggtggta tgcagatctt tgtcaagacc ctcacaggca agaccatcac   3060
cctggaggtt gagagctcgg acaccatcga caacgtcaag gccaagatcc aggacaagga   3120
gggcatcccc ccagaccagc agcgtctcat cttcgccggc aagcagctcg aggatggccg   3180
caccctcgcc gactacaaca tccagaagga gtctaccctc cacctggtgc ttcgtctccg   3240
tggtggtatg cagatcttcg tgaagacctt gactgggaag accatcactt tggaggttga   3300
gagctccgac accattgata atgtgaaggc caagatccag gacaaggagg ggattccccc   3360
agaccagcag cgtctgatct tcgctggcaa gcagctggag gatggacgca ccctcgccga   3420
ctacaacatc cagaaggagt ccaccctcca cctggtgctc cgcctccgtg gtggtcagta   3480
```

-continued a 3481

<210> SEQ ID NO 6
<211> LENGTH: 3166
<212> TYPE: DNA
<213> ORGANISM: Oryza sativa
<220> FEATURE:
<221> NAME/KEY: gene
<222> LOCATION: (1)..(3166)
<223> OTHER INFORMATION: Rice HPPD gene(GenBank number LOC4328425)

<400> SEQUENCE: 6
aaatggtatt gtttagaagt ttagaaaacg ttctgccgga cggaatggtt ccatccctta 60
aaaaaggacg ctgtttcaaa ttcgaaaaaa agaagagcca tcacgataac cagacggtta 120
ctgacgattt tgccgaaggt gattatcgat ggtcagtcaa caaagtataa accctgctta 180
gcggtaataa acacttgatg ttttacgtaa aatcttttga aacttagacg gccaacgact 240
atcaaaatat ttacatcgaa atcatgaaaa aatgttgtgt tcatttgtct ttgcaaataa 300
tttcaaggcc tcataaactt attttaatac aaaataatgg ctaacgtcac actaaatcaa 360
aatccaatat caaatgcttt taaggaagca gtagagatat cttcaattga gattttgact 420
gtttgagaca gctcattcta ccgcttttca tatgtctatc gagaccgagg taatatatgt 480
ggcacaaaac gttttagaga agtgatgtga aaaacactac catccatcca tttgcaataa 540
gaaaatcctc cattactact ctccccgatt cttaatagat aacactatca atttttaaaa 600
atatatattt atcattcatc taattaagga atataattat cttttatttt tttaacttgg 660
tttatcatta aaaacacttt taaatatgac ttatattttc ttatgtttac acatgttttt 720
aaaataaaac aaatgattga acatataatc acctagtaaa aacaagagct ttactccaag 780
ttaccacaaa atttgtttcc ccttccctct aaaaatcaga acagtcacca actttttctca 840 aaaaaaaaaa aagtaacaaa ctcatcagct tcacaaattc accagcagcc aaggcaacca 900
gcaccagagg acaaatcccg tccgcaacca ctagacttag cgtccacgtg gcgccatctc 960
ctccctttat ttaacccccc accaccaact cctcccccca cgccgccact gtcatccact 1020
cccccacacc ccacgacgcg ccacgccacg ccgcgccgcg ccgcgccatg cctcccactc 1080
ccacccccac cgccaccacc ggcgccgtct cggccgctgc ggcggcgggg gagaacgcgg 1140
ggttccgcct cgtcgggcac cgccgcttcg tccgcgccaa cccgcggagc gaccggttcc 1200
aggcgctcgc gttccaccac gtcgagctct ggtgcgccga cgccgcgtcc gccgcgggcc 1260
ggttcgcctt cgccctgggc gcgccgctcg ccgccaggtc cgacctctcc acggggaact 1320
ccgcgcacgc ctccctcctc ctccgctccg cctccgtcgc gttcctcttc accgcccccct 1380 acggcggcga ccacggcgtc ggcgcggacg cggccaccac cgcctccatc ccttccttct 1440
ccccaggcgc cgcgcggagg ttcgccgcgg accacggcct cgcggtgcac gccgtggcgc 1500
tgcgcgtcgc cgacgcggcc gacgccttcc gcgccagcgt cgcggccggt gcgcgcccgg 1560
cgttccagcc cgccgacctc ggcggtggct tcggcctcgc ggaggtggag ctctacggcg 1620
acgtcgtgct ccgcttcgtc agccacccgg acggcgccga cgcgcccttc ctcccgggtt 1680
tcgagggcgt cagcaacccg ggcgccgtgg actacggcct ccgccggttc gaccacgtcg 1740
tcggcaacgt gccggagctc gctccggtag ccgcgtacat ctccgggttc accgggttcc 1800
acgagttcgc cgagttcacc gccgaggacg tgggcaccgc cgagagcggc ctcaactcgg 1860
tggtgctcgc caacaacgcg gagaccgtgc tgctgccgct caacgagccg gtgcacggca 1920

-continued

```
ccaagcggcg gagccagata cagacgtacc tggaccacca cggcggcccg ggggtgcagc   1980

acatcgcgct ggccagcgac gacgtgctcg ggacgctgag ggagatgcgg gcgcgctccg   2040

ccatgggcgg cttcgagttc ttggcgccgc cgccgcccaa ctactacgac ggcgtgcggc   2100

ggcgcgccgg ggacgtgctc tcggaggagc agatcaacga gtgccaggag ctcggggtgc   2160

tcgtggacag ggatgaccag ggggtgttgc tccagatctt caccaagcca gtaggagaca   2220

ggtaaaatcc tcacctcttt catgatgaaa atggcttatg aattcagatt tgcagttatt   2280

tgttggcaca tagcatcgat taggcgcaga aaggtgtcaa gcattatgaa attaatccag   2340

aatgcttgaa taatacagta taatatatga tagtgagctc tgtgatactc catggatact   2400

ctttatgtgt ctccatgaat ccatgatgcg cctttctgaa gattgtgaca ctagaaaggg   2460

aataaagctg aatgtgcata ggaaaaaaat gaaaagccaa tgtgtgtctg tttatgcctt   2520

cttgcaagca tatcccagtt cctttttgcc ggcatgttgt aatgcagata gccagccaca   2580

tatagctact taattagtga gtactccctc tcacaatgta agtcattcta gtattttcca   2640

cattcatatt gatgctaatc tatctagatt cattagcatc aatatgaata tgggaaatac   2700

tagaatgact tacattgtga aacggaggaa gtattactta ctacatctaa ggtccatgga   2760

ttcctttttt tacaaaagaa agaaagaatc ttatggcaac tccatcagca taaaccagca   2820

atgctgctgg gaacaactta aactttaggt tcaggaggtt gtaattgtct ttaagcttaa   2880

tagtctgatt cagtcagtat tctaatttct gctgcatctt tgctattgtt atttcctctc   2940

tgtgactcca aatctaactg gatcagctat ttcactcagg ccaacctttt tcttggagat   3000

gatacaaagg attgggtgca tggagaagga tgagagtggg caggagtacc agaagggcgg   3060

ctgcggcggg tttgggaagg gcaacttctc ggagctgttc aagtccattg aggagtatga   3120

gaaatccctt gaagccaagc aagcccctac agttcaagga tcctag                 3166


<210> SEQ ID NO 7
<211> LENGTH: 4311
<212> TYPE: DNA
<213> ORGANISM: Oryza sativa
<220> FEATURE:
<221> NAME/KEY: gene
<222> LOCATION: (1)..(4311)
<223> OTHER INFORMATION: Rice PPO gene(GenBank number LOC4327918)

<400> SEQUENCE: 7

caaaaaaaat tattcaaaag gaagcaggca gggcagcaca ttgtgaggga atcaggcggc     60

ggcgcacagt tctctccctt ggcaccctcc tttccctcat atgcaatgga ctcaaaaggg    120

cggctgcagc gtatgccggt ggattaggtt tcgagggtgg atccagtgag agcaaaggtg    180

gtggggtgac ccaaggacgc tgcttcgctc aagtccacat gtgcttcgcc tcaaggccag    240

gatgccgccg ccctactcga gactaggtag ctgacttgag actaggccgt tgtcgcgcgt    300

cggggccgcc cagccgctgc tccaccttgg gtcacgctgt cactctatct caaggctggg    360

ccatcgccac tatgcttgaa gccgcactac cgtcccacct caaggccggc accctgtcac    420

tccacctcga ggctacctag acgttatttt gttccgctgc tacgccttag agacacccca    480

ctgccgctct accttgggct atgccgtcgc tctttctcca aggcgcgctg ctacaactcc    540

gccctgagtc tccatgtgcc tgtgtggaga aaggagaggg aagaaagaaa gaaaggagaa    600

agaagtggga ggaatcacta acatgtgagc tctgtatatt gatttggtca gttggattag    660

gtcaacgagc catccaagag aaaacaaccc ttaaaatcat tgagaaaatc atttttaact    720

gttttaatag ttaagagatg aagatatatt ttttttata gaaagagatg aagatatccg    780
```

-continued

```
atatccaata tgataggaat cagaaaacgt atatttttga gggagtcaat gcggacttat    840
tcccaccaga aactgcagca tattggacgc agtggttcct tccgcggtag ctgcgcccgc    900
gcccacggga atgcgattcc cagcccattc caccccccttc ccattccggt gggccattcc    960
gaatccaacc aaccaaccaa ccatcgaacc cgcacccgca tcgtatccac tcctctccag   1020
tctccccgcc gctccgcatc ccgcagccgc tcgtcagcga cggacatggc cgccgccgcc   1080
gcagccatgg ccaccgccac ctccgccacg gcagcgccgc cgctccgcat tcgcgacgcc   1140
gcgaggagga cccgccgacg cggccacgtt cgctgcgccg tcgccagcgg cgcggccgag   1200
gcgcccgcgg cgcccggggc gcgggtgtcg gcggactgcg tcgtggtggg cggcggcatc   1260
agcgggctct gcaccgcgca ggcgctggcc acaaagcacg gcgtcggcga cgtgctcgtc   1320
acggaggccc gcgcccgccc cggcggcaac atcaccaccg ccgagcgcgc cggcgagggc   1380
tacctctggg aggaggggcc caacagcttc cagccttccg accccgtcct caccatggcc   1440
gtacgtcttc ttgctcccct tctcttctga ttctctcgcg gcggagacga catgaatggg   1500
aatggtggtg catggattgg ggcgcgcagg tggacagcgg gctcaaggac gatctcgtgt   1560
tcggggaccc caacgcgccg cggttcgtgc tgtgggaggg gaagctaagg ccggtgccgt   1620
ccaagcccgg cgacctgccg ttcttcgacc tcatgagcat ccccggcaag ctcagggccg   1680
gccttggcgc gctcggcgtt cgagcgccac ctccagtttg tgtgctctcc ccgctgtgca   1740
ttcttgattc acttgtgaaa ttcgattgtg ctgagcgttt ccggcgaagg tttcaggggc   1800
gtgaggagtc ggtggaggac ttcgtgcggc gcaacctcgg cgcggaggtc tttgagcgcc   1860
tcattgagcc tttctgctca ggtgtttatt gtagtgtgca attgctgttt tgtttttgat   1920
gattcagata agaatacggt gatttcggtg cttaggtgtg tatgctggtg atccttcaaa   1980
gctcagtatg aaggctgcat ttgggaaggt gtggaggctg gaggatactg gaggtagcat   2040
tattggtgga accatcaaaa caatccagga gaggggggaaa aaccccaaac cgccgaggga   2100
tccgtgagtg agaaattgcc ttctttgttg gattaattgt ccattgtgtt acactgatat   2160
gccttcacca tttttagccg ccttccaacg ccaaaggggc agacagttgc atctttcagg   2220
aagggtctga ctatgctccc ggatgctatt acatctaggt ttgttatcat tgtctttgta   2280
atttacctag ttcttcaact atggatatta ggtgctgtag attgttcaga tagatgcaca   2340
ttgtacaaca atctaggtag attgattgct atggcttgtt gaattaactg tttcacttgc   2400
atcattgcct cagcacatat gaagcatatg gatagattct tcaatcattt atccctcaat   2460
aacacaattt tgacaccagt gcttctcctt tttttcatcc tgcttcatct ggctatccac   2520
aatataatta agcatacaaa agaggcactc tttgatggac aattcatagt gttgtgggtt   2580
aatattcatt tgcattcttt gagggacaat tcgttacacc ctaacatgaa ctagtaatga   2640
ttggggtgct taaccatttg ttctgcattt cctccatttt caggttgggt agcaaagtca   2700
aactttcatg gaagttgaca agcattacaa agtcagacaa caaaggatat gcattagtgt   2760
atgaaacacc agaaggggtg gtctcggtgc aagctaaaac tgttgtcatg accatcccat   2820
catatgttgc tagtgatatc ttgcggccac tttcagtaag ttatatatat ttaattaact   2880
ttctgttccc aaaatacact gcagcacttc attgcttcct gaggtcctcg attcattttt   2940
cggtagacag gaagtagtat tcatttgcac tttttaaggg attaattcaa catatccact   3000
ggaaatatac atatcctaca catcctgtca acatacttgc taaacagcat tttgtttgag   3060
ttgactggca tctcagcagc caattactat ctttagggga caagccacat tcttaataaa   3120
```

-continued

```
tcctgtcgga aatcactttt tgatttttat agattagtgt tgtcatagaa tttggcttgg   3180

tgatctactt ggtaaggtta actgattcac aagtcggaca atttcttcac caatctagca   3240

gtatgtttaa gtgtgttggt acttaattct aaatgtcctg cgcatggtaa catatcatat   3300

gcaaaaattc ctcagtaacc gaaatttata ctgtaagttt taactgtctt tacactgtta   3360

attttagaca tacttcttcc ttgcttgttc attgaacttg tttcccccctt ccacagagtg   3420

atgcagcaga tgctctgtca atattctatt atccaccagt tgctgctgta actgtttcat   3480

atccaaaaga agcaattaga aaagaatgct taattgacgg agagctccag ggtttcggcc   3540

agctgcatcc gcgtagtcag ggagttgaga ctttaggtac ttataggaat tcaaccttat   3600

tattcttcta acatataaat gaactaatct ttcttgtcta gtttgcattt attgtggatt   3660

aagtttggtt atattgttct tacaagtttg tggtattatt ttgtatagga acaatatata   3720

gctcatcact ctttccaaat cgtgctccag ctggaagggt gttacttctg aactacatag   3780

gaggttctac aaatacaggg attgtttcca aggtatcgct gtcaagttgt ttattttgcg   3840

actatatgat tacagtatcc tgtttttcaa ctccagctgc tgttagactg tcataataaa   3900

tctgctacta catgtttgca cactatttga ctgcatttaa aaactcagat agcctatatt   3960

tttagttgcc tgctactggg tgtatttcta atgatcccat catgtttgca gactgaaagt   4020

gagctggtag aagcagttga ccgtgacctc aggaagatgc tgataaatcc taaagcagtg   4080

gaccctttgg tccttggcgt ccgggtatgg ccacaagcca taccacagtt cctcattggc   4140

catcttgatc atcttgaggc tgcaaaatct gccctgggca aaggtggtta tgatggattg   4200

ttcctcggag ggaactatgt tgcaggagtt gccctgggcc gatgcgttga aggtgcatat   4260

gagagtgcct cacaaatatc tgactacttg accaagtacg cctacaagtg a            4311
```

<210> SEQ ID NO 8
<211> LENGTH: 2463
<212> TYPE: DNA
<213> ORGANISM: Oryza sativa
<220> FEATURE:
<221> NAME/KEY: gene
<222> LOCATION: (1)..(2463)
<223> OTHER INFORMATION: Rice CP12 gene(GenBank number LOC4325791)

<400> SEQUENCE: 8

```
tttaaatcgt atttctactt ggactctcct ttccttttct aattttggat ttttttttg     60

aattttgatt aatctcgtat tgggttctta tatggaaact tctttcaata ttgcttattt    120

tcaattccga atttcagcta tttttaaatc gtatttctac ttggactctc cttttctttt    180

tttctttttc ttcgattaat gtgggaattt ctagccccca cagcgaacgt ggtgactatt    240

ttcaaagctg ttttaataat ataatagatt ttattttagg gcctgttcag attgtagcca    300

aaataaacct tatcaaaatt tgacaatacc aaaattttgt caagttgaca atattgccaa    360

aattttggca ggatttctta cgtatttatc aaatttggca acaaactaaa catagatatt    420

tttttggcaa ctttaccaaa aaagttgtat gattgaaaat gacatcaatc tgaacagccc    480

cttagaactt agaactacaa tctgaacagc cccttagaac ttagaactac agtggaatcc    540

atcttggcat atgtacttgg cagggaattt tttttacatt tttattatta aaaaattaca    600

aaattttttt tcgaaaattt acaaatctag acgcctaaca tcctttagga gggcgttttt    660

ttaaatcgcc cttctaaagg gcgttaaggg acctaaatgc aaaattttta tttgtattcg    720

aaccctttcc accagtttta attgcttaaa agctaataat gcttatttga cactccaaat    780

aattttaaat gaaaaggtaa taaactacaa agttgtagat ctcatcgaga tctatatctt    840
```

ttttataaag tttatctcca tccaatgtcg tttgaaatgt agttctgaga attttttttaa 900 ataggtttta gattttgtaa cgaatatttg gacatctaaa cgatcttaaa tgaaagttgt 960
taattacaaa cttgtagatc ttctccagct ctacaatttt gatataaact ttaatttcat 1020
atggctttat atgatatagt tttaaattgt aaaatcatag aggtagcaag ctatgatgga 1080
aaatttgtat ttaggtccct aacgccctct ggaagggtga tttgaaaaaa gccctctagg 1140
aggacgtgag gcacgactag atttgtaaat tttcggaatg aaaaattatt tttaaatatt 1200
ttaatcaaaa aatgtaaaaa taaaaaaaat tctcggcagg gtggcagcat gggcctaagg 1260
cccagtcaac tgtgggccta taagcgacta atccggctgt aactgggcct tgcaagaggc 1320
ttgtcttgtt ggtccgaact caggaagtcc aggttgcggg gacaacttca aggccatctg 1380
gtttccactt ctcttaccac ctcaattccg ctcttgatcc gagctagctt agtcccaatc 1440
taaaaacttt acaaagaaag aaccatacgc acctattggg caaaatgaaa aataatttgc 1500
tactcaccaa ataatttgag cacctctgca cctgtacact aaataactct gttccaccaa 1560
aatagttgag atatctagga cgtttcattt tgtccgttct tcaccaaact tttccatagt 1620
atctcagata ttttcgagac cgaaagtgat ctttctggcc ttagaccgag ttcacttccc 1680
tacaagccat tctttgctgg cacaacacga acctctacat caatttcgta tccaacctga 1740
acttctgcat acatgtacac acccacagtc atctgctcat gttttcacgg tcaaattaaa 1800
actgcttctc tcaccttaga ttcacccaag ggaaaagaaa aagatctcct ttgccaagtc 1860
cccatttcgc atgaaatatc tcaaaataca gcccacgtgg cacacgacga ttggctgagg 1920
aggcgataag aaacgagtgc acgtcgtcga atcctctctc cccttctccc ccaccccacg 1980
gagctatata tatataaacc ccatctcttc aatccgtgca acgaacgcct cgtcgcaaca 2040
gctacaaacg cccacatcac acgcagaaat ccgcatcaac agccagccat ggcgtccacg 2100
ctgaccaacg tcggcctgtc taccccggcg gcggcggcgt cgtccctcgt taggccggtc 2160
gccggagctg gacgcgtggt gtttccccgt gttggccgcg gcgggttcgc ggcggtgagg 2220
gcgagcgggc cggcgacgcc gccggacatc tcggacaaga tgtcggagag catcgacaag 2280
gcgaaggagg cgtgcgcgga ggacacggcg agcggcgagt gcgcggcggc gtgggacgag 2340
gtggaggagc tgagcgcggc ggcgagccac gcgcgcgaca agctcaagga gacctccgac 2400
ccgctcgagg cctactgcaa ggacaacccg gagaccgacg agtgccgcac ctacgacaac 2460
tga 2463

<210> SEQ ID NO 9
<211> LENGTH: 744
<212> TYPE: DNA
<213> ORGANISM: Artificial Sequence
<220> FEATURE:
<223> OTHER INFORMATION: Sequence of doubling resulting from pQY002066 transforming protoplast

<400> SEQUENCE: 9
ttcaagtcca taggcgaggc gaccggcccg cggcggacgc ggcgtcggcg caccagagct 60
cgacgtggtg gaacgcgagc gcctggaacc ggtcgctccg cgggttggcg cggacgaagc 120
ggcggtgccc gacgaggcgg aacccccgcgt tctccccccgc cgccgcagcg gccgagacgg 180
cgccggtggt ggcggtgggg gtgggagtgg gaggcatggc gcggcgcggc gcggcgtggc 240
gtggcgcgtc gtggggtgtg gggggagtgga tgacagtggc ggcgtggggg gaggagttgg 300
tggtgggggg ttaaataaag ggaggagatg gcgccacgtg gacgctaagt ctagtggttg 360

```
cggacgggat ttgtcctctg gtgctggttg ccttggcaga tagggtaaga actagcacaa    420

gattaaggac acaacaacgg atcaaacagc aaacatattc caacagaaca tacatgtatt    480

caaaaagata gtaacaggca catcacacat gtattcagat aggtagtaac agcacacgta    540

tcctgaactt cataaataag tagaatgaac tagtggcaat aacttttcac acagaacatc    600

tcccttgttt tcaaatatgt agtaacagca cacgtatcct gtacttcaaa acttagtaga    660

atgaactagt ggcagtaatc tttcacacag aaagaatgaa ctagtggcaa taatctttca    720

cacagaatgt tggttgatgg atag                                           744


<210> SEQ ID NO 10
<211> LENGTH: 603
<212> TYPE: DNA
<213> ORGANISM: Artificial Sequence
<220> FEATURE:
<223> OTHER INFORMATION: Sequence of doubling resulting from pQY002068
      transforming protoplast

<400> SEQUENCE: 10

caacgtgcct taggcgaggc gaccggcccg cggcggacgc ggcgtcggcg caccagagct     60

cgacgtggtg gaacgcgagc gcctggaacc ggtcgctccg cgggttggcg cggacgaagc    120

ggcggtgccc gacgaggcgg aaccccgcgt tctcccccgc cgccgcagcg gccgagacgg    180

cgccggtggt ggcggtgggg gtgggagtgg gaggcatggc gcggcgcggc gcggcgtggc    240

gtggcgcgtc gtggggtgtg ggggagtgga tgacagtggc ggcgtggggg gaggagttgg    300

tggtgggggg ttaaataaag ggaggagatg gcgccacgtg gacgctaagt ctagtggttg    360

cggacgggat ttgtcctctg gtgctggttg ccttggagat agggtaagaa ctagcacaag    420

attaaggaca caacaacgga tcaaacagca aacatattcc aacagaacat acatgtattc    480

aaaaagatag taacaggcac atcacacatg tattcagata ggtagtaaca gcacacgtat    540

cctgaacttc agaaataagt agaatgaact agtggcaata acttttcccc ccaaaaacct    600

gtc                                                                  603


<210> SEQ ID NO 11
<211> LENGTH: 477
<212> TYPE: DNA
<213> ORGANISM: Artificial Sequence
<220> FEATURE:
<223> OTHER INFORMATION: Sequence of reversion resulting from pQY002062
      transforming protoplast

<400> SEQUENCE: 11

gggcggattt cgacggaggg gcggagagga ggaggatcct gttggagagc gacttggacc     60

ctggcagctg aaccgccccg gagatctccc tgatgggctg gagcacgatc tcctccgcct    120

tcgccgccgg cgctgccacc gacgacgacg acgcggacgc caccaccacc gcctcccgcc    180

gcccccgcgc ccgcacccgc acccgcatcc ccccgcgcgc cgcggcgggc agccgcagct    240

gcttccgcga cgagaacgcc gccgacgccg ccacggcctg gtccagggac accgccgccg    300

cagccgcggc gttggacgcc atggtcgccg ccattgcggt gtggtggcga ggagaggcgg    360

agatggcgag gttgtggggt gggagatggg atgggttatg tatagacttg ggggtgcgtt    420

ttggggggac tcgtagccaa taaaaaggag ggggctatgg tgtggccgtt tggacat       477


<210> SEQ ID NO 12
<211> LENGTH: 670
<212> TYPE: DNA
```

<213> ORGANISM: Artificial Sequence
<220> FEATURE:
<223> OTHER INFORMATION: Sequence of deletion resulting from pQY002062
      transforming protoplast

<400> SEQUENCE: 12

```
ttttcgttgg aggggcggag aggaggagga tcctgttgga gagcgacttg gaccctggca     60

gctgaaccgc cccggagatc tccctgatgg gctggagcac gatctcctcc gccttcgccg    120

ccggcgctgc caccgacgac gacgacgcgg acgccaccac caccgcctcc cgccgccccc    180

gcgcccgcac ccgcacccgc atccccccgc gcgccgcggc gggcagccgc agctgcttcc    240

gcgacgagaa cgccgccgac gccgccacgg cctggtccag ggacaccgcc gccgcagccg    300

cggcgttgga cgccatggtc gccgccattg gacgagtcgg aatcgcagac cgataccagg    360

atcttgccat cctatggaac tgcctcggtc catggccgcg cactccgtcg ccgccgcgca    420

cgccaccatc gccgcgcgcg cgggtgccgc cgcgccagcg cccgcgccgc cggagcgcct    480

cgggttccgc ctcagcgcgc tcgccggccg cggcctccgc tccccgctcc cgcctcgccg    540

cggcgcgcca tcggcgtccg cgtcgcgccg ccgccacaac aaccgcgtgc gcgcggcggc    600

ggtcgagacg ctcgaggggc aggcggcgac gggggcgctg ctcgagaagt cggaaacccc    660

cgaatccaaa                                                           670
```

<210> SEQ ID NO 13
<211> LENGTH: 777
<212> TYPE: DNA
<213> ORGANISM: Artificial Sequence
<220> FEATURE:
<223> OTHER INFORMATION: Sequence of reversion resulting from pQY002093
      transforming protoplast

<400> SEQUENCE: 13

```
gaacgatgcg agccccacgc tcgaccgccg ccgcgcgcac gcggttgttg tggcggcggc     60

gcgacgcgga cgccgatggc gcgccgcggc gaggcgggag cggggagcgg aggccgcggc    120

cggcgagcgc gctgaggcgg aacccgaggc gctccggcgg cgcgggcgct ggcgcggcgg    180

cacccgcgcg cgcggcgatg gtggcgtgcg cggcggcgac ggagtgcgcg gccatggcga    240

gaggagtgga tggtcacctg actaccggtc ccctcaaact ggtttaattt cccctggcaa    300

aatccacctc cggacctaca atttaagctc cccttttttt ttttaaaaaa aaaaaaaaag    360

agggtaaacc aactaaccta gcttggacct tttttaatgg agtaagggat ttaaaacaaa    420

aacaaaaaaa aaatccaaac tggtaaaaaa acaaacaaac catttaaata aaaattttcc    480

ccaaagggaa attcctggcg aaaaaaatct atgcccctct gggtctatct tggtattttt    540

tccccggggc tccgtttcat ccttcatttt ggcgaataca aaaaaaaccg tttgaatttt    600

ttttggttga aagaatggca atttactggc caggatcatg tactctgcat ctaagaattg    660

attttttgac cccaaatttc aacttagcct ccatcgcagt agtgcgcaca cacaggctga    720

aggtgactct tagacccaat gtcactatct cagcaatatg cagagagaat gacccaa       777
```

<210> SEQ ID NO 14
<211> LENGTH: 635
<212> TYPE: DNA
<213> ORGANISM: Artificial Sequence
<220> FEATURE:
<223> OTHER INFORMATION: Sequence of deletion resulting from pQY002093
      transforming protoplast

<400> SEQUENCE: 14

-continued agaacgatgc gcagcctcgg cgtctcgacc gccgccgcgc gcacgcggtt gttgtggcgg 60
cggcgcgacg cggacgccga tggcgcgccg cggcgaggcg ggagcgggga gcggaggccg 120
cggccggcga gcgcgctgag gcggaacccg aggcgctccg gcggcgcggg cgctggcgcg 180
gcggcacccg cgcgcgcggc gatggtggcg tgcgcggcgg cgacggagtg cgcggccatg 240
gcgagaggag tgtggtgggt accctttcaa acccccaaaa gagtgggtcg ggtctctctt 300
tcggctctcg gcgggggctg cttcccacaa agaccgccat cagacgtgag tgaactgcaa 360
gtctgcaact accactccag gtgctctccc cttaaattac tttactacta cctttattct 420
aggggccggt tcagataatt gccaaaatca ctcgcaccat tttttaataa tattaggatg 480
aaatatatat gtcgcgccaa atttttctac tgttactgaa atttggacac aaactacaca 540
ccaccgtata tttatctttt ttaccaaata ggggtatggt ttaaaatgac tttaatctaa 600
ataggccctg aaatataaaa gcgccccacc cctca 635

<210> SEQ ID NO 15
<211> LENGTH: 652
<212> TYPE: DNA
<213> ORGANISM: Artificial Sequence
<220> FEATURE:
<223> OTHER INFORMATION: Sequence of reversion resulting from pQY002095 transforming protoplast

<400> SEQUENCE: 15
tttgagtaga ctcgccggcg cgctcggcgg tggtgatgtt gccgccgggg cgggcgcggg 60
cctccgtgac gagcacgtcg ccgacgccgt gctttgtggc cagcgcctgc gcggtgcaga 120
gcccgctgat gccgccgccc accacgacgc agtccgccga cacccgcgcc ccgggcgccg 180
cgggcgcctc ggccgcgccg ctggcgacgg cgcagcgaac gtggccgcgt cggcgggtcc 240
tcctcgcggc gtcgcgaatg cggagcggcg gcgctgccgt ggcggaggtg gcggtggcca 300
tggctgcggc ggcggcggcc atgtccgtcg ctgacatgcg gatttctgcg tgtgatgtgg 360
gcgtttgtag ctgttgcgac gaggcgttcg ttgcacggat tgaagagatg ggtttatat 420 atatatagct ccgtggggtg ggggagaagg ggagagagga ttcgacgacg tgcactcgtt 480
tcttatcgcc tcctcagcca atcgtcgtgt gccacgtggg ctgtattttg agatatttca 540
tgcgaaatgg ggacttggca aaggagatct ttttcttttc ccttgggtga atctaaggtg 600
agagaagcag ttttaatttg accgtgaaaa catgagccaa aaggaaaaaa gg 652

<210> SEQ ID NO 16
<211> LENGTH: 506
<212> TYPE: DNA
<213> ORGANISM: Artificial Sequence
<220> FEATURE:
<223> OTHER INFORMATION: Sequence of deletion resulting from pQY002095 transforming protoplast

<400> SEQUENCE: 16
acgcgtggtt cttccggtag ctgcgcccgc gcccacggga atgcgattcc cagcccattc 60
cacccccttc ccattccggt gggccattcc gaatccaacc aaccaaccaa ccatcgaacc 120
cgcacccgca tcgtatccac tcctctccag tctccccgcc gctccgcatc ccgcagccgc 180
tcgatgcgga tttctgcgtg tgatgtgggc gtttgtagct gttgcgacga ggcgttcgtt 240
gcacggattg aagagatggg gtttatatat atatagctcc gtggggtggg ggagaagggg 300
agagaggatt cgacgacgtg cactcgtttc ttatcgcctc ctcagccaat cgtcgtgtgc 360
cacgtgggct gtattttgag atatttcatg cgaaatgggg acttggcaaa ggagatcttt 420
ttcttttccc ttgggtgaat ctaaggtgag agaagcagtt ttaatttgac cgtgaaaaca 480
tagcccagaa tgacaaaata accttt 506

<210> SEQ ID NO 17
<211> LENGTH: 614
<212> TYPE: DNA
<213> ORGANISM: Artificial Sequence
<220> FEATURE:
<223> OTHER INFORMATION: Sequence of reversion resulting from pQY002098
transforming protoplast

<400> SEQUENCE: 17
gcatcgtccg gccgtcggcg gtggtgatgt tgccgccggg gcgggcgcgg gcctccgtga 60
cgagcacgtc gccgacgccg tgctttgtgg ccagcgcctg cgcggtgcag agcccgctga 120
tgccgccgcc caccacgacg cagtccgccg acacccgcgc cccgggcgcc gcgggcgcct 180
cggccgcgcc gctggcgacg gcgcagcgaa cgtggccgcg tcggcgggtc ctcctcgcgg 240
cgtcgcgaat gcggagcggc ggcgctgccg tggcggaggt ggcggtggcc atggctgcgg 300
cggcggcggc catgttgtgg gcgtttgtag ctgttgcgac gaggcgttcg ttgcacggat 360
tgaagagatg gggtttatat atatatagct ccgtggggtg ggggagaagg ggaaagagga 420
ttcgacgacg tgcactcgtt tcttatcgcc tcctcagcca atcgtcgtgt gccacgtggg 480
ctgtattttg agatatttca tgcgaaatgg ggacttggca aaggagatct ttttcttttc 540
ccttgggtga atctaaggtg agagaagcag ttttaatttg accgtgaaaa catgagccca 600
aattgacaaa tccc 614

<210> SEQ ID NO 18
<211> LENGTH: 574
<212> TYPE: DNA
<213> ORGANISM: Artificial Sequence
<220> FEATURE:
<223> OTHER INFORMATION: Sequence of HPPD doubling in QY2091-13

<400> SEQUENCE: 18
ggatacgtgt gctgttacta cctatctgaa tacatgtgtg atgtgcctgt tactatcttt 60
ttgaatacat gtatgttctg ttggaatatg tttgctgttt gatccgttgt tgtgtcctta 120
atcttgtgct agttcttacc ctatctgcca aggcaaccag caccagagga caaatcccgt 180
ccgcaaccac tagacttagc gtccacgtgg cgccatctcc tccctttatt taacccccca 240
ccaccaactc ctccccccac gccgccactg tcatccactc ccccacaccc cacgacgcgc 300
cacgccacgc cgcgccgcgc cgcgccatgc ctcccactcc cacccccacc gccaccaccg 360
gcgccgtctc ggccgctgcg gcggcggggg agaacgcggg gttccgcctc gtcgggcacc 420
gccgcttcgt ccgcgccaac ccgcggagcg accggttcca ggcgctcgcg ttccaccacg 480
tcgagctctg gtgcgccgac gccgcgtccg ccgcgggccg gttcgccttc gccctgggcg 540
cgccgctcgc cgccaggtcc gacctctcca cggg 574

<210> SEQ ID NO 19
<211> LENGTH: 551
<212> TYPE: DNA
<213> ORGANISM: Artificial Sequence
<220> FEATURE:
<223> OTHER INFORMATION: Sequence of HPPD doubling in QY2091-20

<400> SEQUENCE: 19
aggatacgtg tgctgttact acctatctga atacatgtgt gatgtgcctg ttactatctt 60

-continued tttgaataca tgtatgttct gttggaatat gtttgctgtt tgatccgttg ttgtgtcctt 120
aatcttgtcc aaggcaacca gcaccagagg acaaatcccg tccgcaacca ctagacttag 180
cgtccacgtg gcgccatctc ctccctttat ttaacccccc accaccaact cctcccccca 240
cgccgccact gtcatccact cccccacacc ccacgacgcg ccacgccacg ccgcgccgcg 300
ccgcgccatg cctcccactc ccaccccac cgccaccacc ggcgccgtct cggccgctgc 360
ggcggcgggg gagaacgcgg ggttccgcct cgtcgggcac cgccgcttcg tccgcgccaa 420
cccgcggagc gaccggttcc aggcgctcgc gttccaccac gtcgagctct ggtgcgccga 480
cgccgcgtcc gccgcgggcc ggttcgcctt cgccctgggc gcgccgctcg ccgccaggtc 540
cgacctctcc a 551

<210> SEQ ID NO 20
<211> LENGTH: 155
<212> TYPE: DNA
<213> ORGANISM: Artificial Sequence
<220> FEATURE:
<223> OTHER INFORMATION: Sequence of PPO1 reversion in QY2234-20

<400> SEQUENCE: 20
tctctctccc ttctccccca ccccacggag ctatatatat ataaacccca tctcttcaat 60
ccgtgcaacg aacgcctcgt cgcaacagct acaaacgccc acaagcaacg aaggaaatgg 120
gcggccgccg ccgaaccctg ggccccggcc cctcc 155

<210> SEQ ID NO 21
<211> LENGTH: 447
<212> TYPE: DNA
<213> ORGANISM: Artificial Sequence
<220> FEATURE:
<223> OTHER INFORMATION: Sequence of PPO1 reversion in QY2234-205

<400> SEQUENCE: 21
cccttctccc ccaccccacg gagctatata tatataaacc ccatctcttc aatccgtgca 60
acgaacgcct cgtcgcaaca gctacaaacg gacatggccg ccgccgccgc agccatggcc 120
accgccacct ccgccacggc agcgccgccg ctccgcattc gcgacgccgc gaggaggacc 180
cgccgacgcg gccacgttcg ctgcgccgtc gccagcggcg cggccgaggc gcccgcggcg 240
cccggggcgc gggtgtcggc ggactgcgtc gtggtgggcg gcggcatcgg cgggctctgc 300
accgcgcagg cgctggccac aaagcacggc gtcggcgacg tgctcgtcac ggaggcccgc 360
ccccgccccg gcggcaacat caccaccgcc gagcgcgccg gcgagggcta cctctgggag 420
gaggggccca acagcttcca gccttcc 447

<210> SEQ ID NO 22
<211> LENGTH: 463
<212> TYPE: DNA
<213> ORGANISM: Artificial Sequence
<220> FEATURE:
<223> OTHER INFORMATION: Sequence of PPO1 reversion in QY2234-207

<400> SEQUENCE: 22
cccttctccc ccaccccacg gagctatata tatataaacc ccatctcttc aatccgtgca 60
acgaacgcct cgtcgcaaca gctacaaacg cccacagtca gcgacggaca tggccgccgc 120
cgccgcagcc atggccaccg ccacctccgc cacggcagcg ccgccgctcc gcattcgcga 180
cgccgcgagg aggacccgcc gacgcggcca cgttcgctgc gccgtcgcca gcggcgcggc 240
cgaggcgccc gcggcgcccg gggcgcgggt gtcggcggac tgcgtcgtgg tgggcggcgg 300
catcagcggg ctctgcaccg cgcaggcgct ggccacaaag cacggcgtcg gcgacgtgct 360
cgtcacggag gcccgcgccc gccccggcgg caacatcacc accgccgagc gcgccggcga 420
gggctacctc tgggaggagg ggcccaacag cttccagcct tcc 463

<210> SEQ ID NO 23
<211> LENGTH: 388
<212> TYPE: DNA
<213> ORGANISM: Artificial Sequence
<220> FEATURE:
<223> OTHER INFORMATION: Sequence of PPO1 reversion in QY2234-580

<400> SEQUENCE: 23
cccttctccc ccaccccacg gagctatata tatataaacc ccatctcttc aatccgtgca 60
acgaacgcct cgtcgcaaca ggtacatggc cgccgccgcc gcagccatgg ccaccgccac 120
ctccgccacg gcagcgccgc cgctccgcat tcgcgacgcc gcgaggagga cccgccgacg 180
cggccacgtt cgctgcgccg tcgccagcgg cgcggccgag gcgcccgcgg cgcccggggc 240
gcgggtgtcg gcggactgcg tcgtggtggg cggcggcatc agcgggctct gcaccgcgca 300
ggcgctggcc acaaagcacg gcgtcggcga cgtgctcgtc acggaggccc gcgcccgccc 360
cggcggcaac atcaccaccg ccgagcgc 388

<210> SEQ ID NO 24
<211> LENGTH: 417
<212> TYPE: DNA
<213> ORGANISM: Artificial Sequence
<220> FEATURE:
<223> OTHER INFORMATION: Sequence of PPO1 reversion in QY2234-H5-159

<400> SEQUENCE: 24
cccttctccc ccaccccacg gagctatata tatataaacc ccatctcttc aatccgtgca 60
acgaacgcct cgtcgcaaca gctacaaacg gacatggccg ccgccgccgc agccatggcc 120
accgccacct ccgccacggc agcgccgccg ctccgcattc gcgacgccgc gaggaggacc 180
cgccgacgcg gccacgttcg ctgcgccgtc gccagcggcg cggccgaggc gcccgcggcg 240
cccggggcgc gggtgtcggc ggactgcgtc gtggtgggcg gcggcatcag cgggctctgc 300
accgcgcagg cgctggccac aaagcacggc gtcggcgacg tgctcgtcac ggaggcccgc 360
gcccgccccg gcggcaacat caccaccgcc gagcgcgccg gcgagggcta cctctgg 417

<210> SEQ ID NO 25
<211> LENGTH: 430
<212> TYPE: DNA
<213> ORGANISM: Artificial Sequence
<220> FEATURE:
<223> OTHER INFORMATION: Sequence of PPO1 reversion in QY2234-H5-232

<400> SEQUENCE: 25
ccttctcccc caccccacgg agctatatat atataaaccc catctcttca atccgtgcaa 60
cgaacgcctc gtcgcaacag ctacaaacgc ccgtcagcga cggacatggc cgccgccgcc 120
gcagccatgg ccaccgccac ctccgccacg gcagcgccgc cgctccgcat tcgcgacgcc 180
gcgaggagga cccgccgacg cggccacgtt cgctgcgccg tcgccagcgg cgcggccgag 240
gcgcccgcgg cgcccggggc gcgggtgtcg gcggactgcg tcgtggtggg cggcggcatc 300
agcgggctct gcaccgcgca ggcgctggcc acaaagcacg gcgtcggcga cgtgctcgtc 360
acggaggccc gcgcccgccc cggcggcaac atcaccaccg ccgagcgcgc cggcgagggc 420

-continued tacctctggg 430

<210> SEQ ID NO 26
<211> LENGTH: 424
<212> TYPE: DNA
<213> ORGANISM: Artificial Sequence
<220> FEATURE:
<223> OTHER INFORMATION: Sequence of PPO1 reversion in QY2234-H5-263

<400> SEQUENCE: 26
ataaacccca tctcttcaat ccgtgcaacg aacgcctcgt cgcaacagct acaaacgccc 60
acagtcagcg acggacatgg ccgccgccgc cgcagccatg gccaccgcca cctccgccac 120
ggcagcgccg ccgctccgca ttcgcgacgc cgcgaggagg acccgccgac gcggccacgt 180
tcgctgcgcc gtcgccagcg gcgcggccga ggcgcccgcg gcgcccgggg cgcgggtgtc 240
ggcggactgc gtcgtggtgg gcggcggcat cagcgggctc tgcaccgcgc aggcgctggc 300
cacaaagcac ggcgtcggcg acgtgctcgt cacggaggcc cgcgcccgcc ccggcggcaa 360
catcaccacc gccgagcgcg ccggcgaggg ctacctctgg gaggaggggc ccaacagctt 420
ccag 424

<210> SEQ ID NO 27
<211> LENGTH: 20
<212> TYPE: DNA
<213> ORGANISM: Artificial Sequence
<220> FEATURE:
<223> OTHER INFORMATION: OsHPPD-guide RNA1

<400> SEQUENCE: 27
gtgctggttg ccttggctgc 20

<210> SEQ ID NO 28
<211> LENGTH: 20
<212> TYPE: DNA
<213> ORGANISM: Artificial Sequence
<220> FEATURE:
<223> OTHER INFORMATION: OsHPPD-guide RNA2

<400> SEQUENCE: 28
cacaaattca ccagcagcca 20

<210> SEQ ID NO 29
<211> LENGTH: 20
<212> TYPE: DNA
<213> ORGANISM: Artificial Sequence
<220> FEATURE:
<223> OTHER INFORMATION: OsHPPD-guide RNA3

<400> SEQUENCE: 29
taagaactag cacaagatta 20

<210> SEQ ID NO 30
<211> LENGTH: 20
<212> TYPE: DNA
<213> ORGANISM: Artificial Sequence
<220> FEATURE:
<223> OTHER INFORMATION: OsHPPD-guide RNA4

<400> SEQUENCE: 30
gaaataatca ccaaacagat 20

<210> SEQ ID NO 31

-continued

<211> LENGTH: 58
<212> TYPE: DNA
<213> ORGANISM: Artificial Sequence
<220> FEATURE:
<223> OTHER INFORMATION: OsHPPD-sgRNA1-F

<400> SEQUENCE: 31
atatggtctc gggcggtgct ggttgccttg gctgcgtttt agagctagaa atagcaag 58

<210> SEQ ID NO 32
<211> LENGTH: 58
<212> TYPE: DNA
<213> ORGANISM: Artificial Sequence
<220> FEATURE:
<223> OTHER INFORMATION: OsHPPD-sgRNA2-F

<400> SEQUENCE: 32
atatggtctc gggcgcacaa attcaccagc agccagtttt agagctagaa atagcaag 58

<210> SEQ ID NO 33
<211> LENGTH: 52
<212> TYPE: DNA
<213> ORGANISM: Artificial Sequence
<220> FEATURE:
<223> OTHER INFORMATION: OsHPPD-sgRNA3-R

<400> SEQUENCE: 33
tattggtctc taaactaatc ttgtgctagt tcttagcttc ttggtgccgc gc 52

<210> SEQ ID NO 34
<211> LENGTH: 52
<212> TYPE: DNA
<213> ORGANISM: Artificial Sequence
<220> FEATURE:
<223> OTHER INFORMATION: OsHPPD-sgRNA4-R

<400> SEQUENCE: 34
tattggtctc taaacatctg tttggtgatt atttcgcttc ttggtgccgc gc 52

<210> SEQ ID NO 35
<211> LENGTH: 21
<212> TYPE: DNA
<213> ORGANISM: Artificial Sequence
<220> FEATURE:
<223> OTHER INFORMATION: OsHPPDduplicated-primer1-F

<400> SEQUENCE: 35
cactaccatc catccatttg c 21

<210> SEQ ID NO 36
<211> LENGTH: 19
<212> TYPE: DNA
<213> ORGANISM: Artificial Sequence
<220> FEATURE:
<223> OTHER INFORMATION: OsHPPDduplicated-primer6-R

<400> SEQUENCE: 36
gagttccccg tggagaggt 19

<210> SEQ ID NO 37
<211> LENGTH: 22
<212> TYPE: DNA
<213> ORGANISM: Artificial Sequence
<220> FEATURE:
<223> OTHER INFORMATION: OsHPPDduplicated-primer3-F

<400> SEQUENCE: 37
tccattacta ctctccccga tt 22

<210> SEQ ID NO 38
<211> LENGTH: 19
<212> TYPE: DNA
<213> ORGANISM: Artificial Sequence
<220> FEATURE:
<223> OTHER INFORMATION: OsHPPDduplicated-primer7-R

<400> SEQUENCE: 38
gtgtggggga gtggatgac 19

<210> SEQ ID NO 39
<211> LENGTH: 20
<212> TYPE: DNA
<213> ORGANISM: Artificial Sequence
<220> FEATURE:
<223> OTHER INFORMATION: OsHPPDduplicated-primer5-F

<400> SEQUENCE: 39
tgtagcttgt gcgtttcgat 20

<210> SEQ ID NO 40
<211> LENGTH: 18
<212> TYPE: DNA
<213> ORGANISM: Artificial Sequence
<220> FEATURE:
<223> OTHER INFORMATION: OsHPPDduplicated-primer2-R

<400> SEQUENCE: 40
gggatgccct ctttgtcc 18

<210> SEQ ID NO 41
<211> LENGTH: 23
<212> TYPE: DNA
<213> ORGANISM: Artificial Sequence
<220> FEATURE:
<223> OTHER INFORMATION: OsHPPDduplicated-primer8-F

<400> SEQUENCE: 41
tctgtgtgaa gattattgcc act 23

<210> SEQ ID NO 42
<211> LENGTH: 20
<212> TYPE: DNA
<213> ORGANISM: Artificial Sequence
<220> FEATURE:
<223> OTHER INFORMATION: OsHPPDduplicated-primer4-R

<400> SEQUENCE: 42
gggatgccct ccttatcttg 20

<210> SEQ ID NO 43
<211> LENGTH: 21
<212> TYPE: DNA
<213> ORGANISM: Artificial Sequence
<220> FEATURE:
<223> OTHER INFORMATION: UBQ5-F

<400> SEQUENCE: 43
accacttcga ccgccactac t 21

<210> SEQ ID NO 44
<211> LENGTH: 19
<212> TYPE: DNA

-continued

<213> ORGANISM: Artificial Sequence
<220> FEATURE:
<223> OTHER INFORMATION: UBQ5-R

<400> SEQUENCE: 44
acgcctaagc ctgctggtt 19

<210> SEQ ID NO 45
<211> LENGTH: 22
<212> TYPE: DNA
<213> ORGANISM: Artificial Sequence
<220> FEATURE:
<223> OTHER INFORMATION: RT-OsHPPD-F

<400> SEQUENCE: 45
cagatcttca ccaagccagt ag 22

<210> SEQ ID NO 46
<211> LENGTH: 20
<212> TYPE: DNA
<213> ORGANISM: Artificial Sequence
<220> FEATURE:
<223> OTHER INFORMATION: RT-OsHPPD-R

<400> SEQUENCE: 46
gagaagttgc ccttcccaaa 20

<210> SEQ ID NO 47
<211> LENGTH: 20
<212> TYPE: DNA
<213> ORGANISM: Artificial Sequence
<220> FEATURE:
<223> OTHER INFORMATION: RT-OsUbi2-F

<400> SEQUENCE: 47
cctccgtggt ggtcagtaat 20

<210> SEQ ID NO 48
<211> LENGTH: 18
<212> TYPE: DNA
<213> ORGANISM: Artificial Sequence
<220> FEATURE:
<223> OTHER INFORMATION: RT-OsUbi2-R

<400> SEQUENCE: 48
gaacagaggc tcgggacg 18

<210> SEQ ID NO 49
<211> LENGTH: 28
<212> TYPE: DNA
<213> ORGANISM: Artificial Sequence
<220> FEATURE:
<223> OTHER INFORMATION: Primer 8F

<400> SEQUENCE: 49
tctgtgtgaa gattattgcc actagttc 28

<210> SEQ ID NO 50
<211> LENGTH: 19
<212> TYPE: DNA
<213> ORGANISM: Artificial Sequence
<220> FEATURE:
<223> OTHER INFORMATION: Primer 6R

<400> SEQUENCE: 50
gagttccccg tggagaggt 19

<210> SEQ ID NO 51
<211> LENGTH: 26
<212> TYPE: DNA
<213> ORGANISM: Artificial Sequence
<220> FEATURE:
<223> OTHER INFORMATION: Test 141-F

<400> SEQUENCE: 51
ccccttccct ctaaaaatca gaacag 26

<210> SEQ ID NO 52
<211> LENGTH: 24
<212> TYPE: DNA
<213> ORGANISM: Artificial Sequence
<220> FEATURE:
<223> OTHER INFORMATION: Primer 4R

<400> SEQUENCE: 52
gggatgccct ccttatcttg gatc 24

<210> SEQ ID NO 53
<211> LENGTH: 25
<212> TYPE: DNA
<213> ORGANISM: Artificial Sequence
<220> FEATURE:
<223> OTHER INFORMATION: Primer 3F

<400> SEQUENCE: 53
cctccattac tactctcccc gattc 25

<210> SEQ ID NO 54
<211> LENGTH: 21
<212> TYPE: DNA
<213> ORGANISM: Artificial Sequence
<220> FEATURE:
<223> OTHER INFORMATION: Primer 7R

<400> SEQUENCE: 54
gtgtggggga gtggatgaca g 21

<210> SEQ ID NO 55
<211> LENGTH: 20
<212> TYPE: DNA
<213> ORGANISM: Artificial Sequence
<220> FEATURE:
<223> OTHER INFORMATION: pg-Hyg-R1

<400> SEQUENCE: 55
tcgtccatca cagtttgcca 20

<210> SEQ ID NO 56
<211> LENGTH: 20
<212> TYPE: DNA
<213> ORGANISM: Artificial Sequence
<220> FEATURE:
<223> OTHER INFORMATION: pg-35S-F

<400> SEQUENCE: 56
tgacgtaagg gatgacgcac 20

<210> SEQ ID NO 57
<211> LENGTH: 20
<212> TYPE: DNA
<213> ORGANISM: Artificial Sequence
<220> FEATURE:

<223> OTHER INFORMATION: OsPPO-guide RNA1

<400> SEQUENCE: 57
ccatgtccgt cgctgacgag 20

<210> SEQ ID NO 58
<211> LENGTH: 20
<212> TYPE: DNA
<213> ORGANISM: Artificial Sequence
<220> FEATURE:
<223> OTHER INFORMATION: OsPPO-guide RNA2

<400> SEQUENCE: 58
ccgctcgtca gcgacggaca 20

<210> SEQ ID NO 59
<211> LENGTH: 20
<212> TYPE: DNA
<213> ORGANISM: Artificial Sequence
<220> FEATURE:
<223> OTHER INFORMATION: OsPPO-guide RNA3

<400> SEQUENCE: 59
gccatggctg gctgttgatg 20

<210> SEQ ID NO 60
<211> LENGTH: 20
<212> TYPE: DNA
<213> ORGANISM: Artificial Sequence
<220> FEATURE:
<223> OTHER INFORMATION: OsPPO-guide RNA4

<400> SEQUENCE: 60
cggatttctg cgtgtgatgt 20

<210> SEQ ID NO 61
<211> LENGTH: 58
<212> TYPE: DNA
<213> ORGANISM: Artificial Sequence
<220> FEATURE:
<223> OTHER INFORMATION: OsPPO1-sgRNA1-F

<400> SEQUENCE: 61
atatggtctc gggcgccatg tccgtcgctg acgaggtttt agagctagaa atagcaag 58

<210> SEQ ID NO 62
<211> LENGTH: 58
<212> TYPE: DNA
<213> ORGANISM: Artificial Sequence
<220> FEATURE:
<223> OTHER INFORMATION: OsPPO1-sgRNA2-F

<400> SEQUENCE: 62
atatggtctc gggcgccgct cgtcagcgac ggacagtttt agagctagaa atagcaag 58

<210> SEQ ID NO 63
<211> LENGTH: 55
<212> TYPE: DNA
<213> ORGANISM: Artificial Sequence
<220> FEATURE:
<223> OTHER INFORMATION: OsPPO1-sgRNA3-R

<400> SEQUENCE: 63
tattggtctc taaaccatca acagccagcc atggcgcttc ttggtgccgc gcctc 55

<210> SEQ ID NO 64
<211> LENGTH: 55
<212> TYPE: DNA
<213> ORGANISM: Artificial Sequence
<220> FEATURE:
<223> OTHER INFORMATION: OsPPO1-sgRNA4-R

<400> SEQUENCE: 64
tattggtctc taaacacatc acacgcagaa atccggcttc ttggtgccgc gcctc 55

<210> SEQ ID NO 65
<211> LENGTH: 21
<212> TYPE: DNA
<213> ORGANISM: Artificial Sequence
<220> FEATURE:
<223> OTHER INFORMATION: OsPPOinversion-checkF1PPO-F1

<400> SEQUENCE: 65
gctatgccgt cgctctttct c 21

<210> SEQ ID NO 66
<211> LENGTH: 20
<212> TYPE: DNA
<213> ORGANISM: Artificial Sequence
<220> FEATURE:
<223> OTHER INFORMATION: OsPPOinversion-checkF2PPO-F2

<400> SEQUENCE: 66
cggacttatt cccaccagaa 20

<210> SEQ ID NO 67
<211> LENGTH: 22
<212> TYPE: DNA
<213> ORGANISM: Artificial Sequence
<220> FEATURE:
<223> OTHER INFORMATION: OsPPOinversion-checkR1PPO-R1

<400> SEQUENCE: 67
gagaagggga gcaagaagac gt 22

<210> SEQ ID NO 68
<211> LENGTH: 19
<212> TYPE: DNA
<213> ORGANISM: Artificial Sequence
<220> FEATURE:
<223> OTHER INFORMATION: OsPPOinversion-checkR2PPO-R2

<400> SEQUENCE: 68
aaggctggaa gctgttggg 19

<210> SEQ ID NO 69
<211> LENGTH: 22
<212> TYPE: DNA
<213> ORGANISM: Artificial Sequence
<220> FEATURE:
<223> OTHER INFORMATION: OsCPinversion-checkF1CP-F1

<400> SEQUENCE: 69
cattccacca aactcccctc tg 22

<210> SEQ ID NO 70
<211> LENGTH: 20
<212> TYPE: DNA
<213> ORGANISM: Artificial Sequence
<220> FEATURE:
<223> OTHER INFORMATION: OsCPinversion-checkF2CP-F2

<400> SEQUENCE: 70
aggtctcctt gagcttgtcg 20

<210> SEQ ID NO 71
<211> LENGTH: 25
<212> TYPE: DNA
<213> ORGANISM: Artificial Sequence
<220> FEATURE:
<223> OTHER INFORMATION: OsCPinversion-checkR1CP-R1

<400> SEQUENCE: 71
gtcatctgct catgttttca cggtc 25

<210> SEQ ID NO 72
<211> LENGTH: 22
<212> TYPE: DNA
<213> ORGANISM: Artificial Sequence
<220> FEATURE:
<223> OTHER INFORMATION: OsCPinversion-checkR2CP-R2

<400> SEQUENCE: 72
ctgaggaggc gataagaaac ga 22

<210> SEQ ID NO 73
<211> LENGTH: 21
<212> TYPE: DNA
<213> ORGANISM: Artificial Sequence
<220> FEATURE:
<223> OTHER INFORMATION: RT-OsPPO1-F

<400> SEQUENCE: 73
gcagcagatg ctctgtcaat a 21

<210> SEQ ID NO 74
<211> LENGTH: 22
<212> TYPE: DNA
<213> ORGANISM: Artificial Sequence
<220> FEATURE:
<223> OTHER INFORMATION: RT-OsPPO1-R

<400> SEQUENCE: 74
ctggagctct ccgtcaatta ag 22

<210> SEQ ID NO 75
<211> LENGTH: 17
<212> TYPE: DNA
<213> ORGANISM: Artificial Sequence
<220> FEATURE:
<223> OTHER INFORMATION: RT-OsCP12-F1

<400> SEQUENCE: 75
ccggacatct cggacaa 17

<210> SEQ ID NO 76
<211> LENGTH: 17
<212> TYPE: DNA
<213> ORGANISM: Artificial Sequence
<220> FEATURE:
<223> OTHER INFORMATION: RT-OsCP12-R1

<400> SEQUENCE: 76
ctcagctcct ccacctc 17

<210> SEQ ID NO 77
<211> LENGTH: 19

<212> TYPE: DNA
<213> ORGANISM: Artificial Sequence
<220> FEATURE:
<223> OTHER INFORMATION: PPO-R2

<400> SEQUENCE: 77
aaggctggaa gctgttggg 19

<210> SEQ ID NO 78
<211> LENGTH: 22
<212> TYPE: DNA
<213> ORGANISM: Artificial Sequence
<220> FEATURE:
<223> OTHER INFORMATION: CP-R2

<400> SEQUENCE: 78
ctgaggaggc gataagaaac ga 22

<210> SEQ ID NO 79
<211> LENGTH: 21
<212> TYPE: DNA
<213> ORGANISM: Artificial Sequence
<220> FEATURE:
<223> OTHER INFORMATION: PPO-F2

<400> SEQUENCE: 79
cggacttatt tcccaccaga a 21

<210> SEQ ID NO 80
<211> LENGTH: 20
<212> TYPE: DNA
<213> ORGANISM: Artificial Sequence
<220> FEATURE:
<223> OTHER INFORMATION: CP-F2

<400> SEQUENCE: 80
aggtctcctt gagcttgtcg 20

<210> SEQ ID NO 81
<211> LENGTH: 20
<212> TYPE: DNA
<213> ORGANISM: Artificial Sequence
<220> FEATURE:
<223> OTHER INFORMATION: OsEPSPS-guide RNA1

<400> SEQUENCE: 81
ccacaccact cctctcgcca 20

<210> SEQ ID NO 82
<211> LENGTH: 20
<212> TYPE: DNA
<213> ORGANISM: Artificial Sequence
<220> FEATURE:
<223> OTHER INFORMATION: OsEPSPS-guide RNA2

<400> SEQUENCE: 82
ccatggcgag aggagtggtg 20

<210> SEQ ID NO 83
<211> LENGTH: 20
<212> TYPE: DNA
<213> ORGANISM: Artificial Sequence
<220> FEATURE:
<223> OTHER INFORMATION: OsEPSPS-guide RNA3

<400> SEQUENCE: 83
atggtcgccg ccattgccgg 20

<210> SEQ ID NO 84
<211> LENGTH: 20
<212> TYPE: DNA
<213> ORGANISM: Artificial Sequence
<220> FEATURE:
<223> OTHER INFORMATION: OsEPSPS-guide RNA4

<400> SEQUENCE: 84
gacctccacg ccgccggcaa 20

<210> SEQ ID NO 85
<211> LENGTH: 20
<212> TYPE: DNA
<213> ORGANISM: Artificial Sequence
<220> FEATURE:
<223> OTHER INFORMATION: OsEPSPS-guide RNA5

<400> SEQUENCE: 85
tagtcatgtg accatccctg 20

<210> SEQ ID NO 86
<211> LENGTH: 20
<212> TYPE: DNA
<213> ORGANISM: Artificial Sequence
<220> FEATURE:
<223> OTHER INFORMATION: OsEPSPS-guide RNA6

<400> SEQUENCE: 86
ttgactcttt ggttcatgct 20

<210> SEQ ID NO 87
<211> LENGTH: 20
<212> TYPE: DNA
<213> ORGANISM: Artificial Sequence
<220> FEATURE:
<223> OTHER INFORMATION: EPSPSinversion checkF1

<400> SEQUENCE: 87
atccaagtta ccccctctgc 20

<210> SEQ ID NO 88
<211> LENGTH: 20
<212> TYPE: DNA
<213> ORGANISM: Artificial Sequence
<220> FEATURE:
<223> OTHER INFORMATION: EPSPSinversion checkR1

<400> SEQUENCE: 88
cacaaacaca gccacctcac 20

<210> SEQ ID NO 89
<211> LENGTH: 20
<212> TYPE: DNA
<213> ORGANISM: Artificial Sequence
<220> FEATURE:
<223> OTHER INFORMATION: EPSPSinversion check-nestF2

<400> SEQUENCE: 89
atgtccacgt ccacaccata 20

<210> SEQ ID NO 90
<211> LENGTH: 20
<212> TYPE: DNA
<213> ORGANISM: Artificial Sequence
<220> FEATURE:
<223> OTHER INFORMATION: EPSPSinversion check-nestR2

<400> SEQUENCE: 90
aatggaattc acgcaagagg 20

<210> SEQ ID NO 91
<211> LENGTH: 20
<212> TYPE: DNA
<213> ORGANISM: Artificial Sequence
<220> FEATURE:
<223> OTHER INFORMATION: EPSPSinversion checkF3

<400> SEQUENCE: 91
gtaggggttc ttggggttgt 20

<210> SEQ ID NO 92
<211> LENGTH: 20
<212> TYPE: DNA
<213> ORGANISM: Artificial Sequence
<220> FEATURE:
<223> OTHER INFORMATION: EPSPSinversion checkR3

<400> SEQUENCE: 92
cgcatgctaa cttgagacga 20

<210> SEQ ID NO 93
<211> LENGTH: 20
<212> TYPE: DNA
<213> ORGANISM: Artificial Sequence
<220> FEATURE:
<223> OTHER INFORMATION: EPSPSinversion check-nestF4

<400> SEQUENCE: 93
ggatcgtgtt caccgacttc 20

<210> SEQ ID NO 94
<211> LENGTH: 20
<212> TYPE: DNA
<213> ORGANISM: Artificial Sequence
<220> FEATURE:
<223> OTHER INFORMATION: EPSPSinversion check-nestR4

<400> SEQUENCE: 94
ccggtacaac gcacgagtat 20

<210> SEQ ID NO 95
<211> LENGTH: 23
<212> TYPE: DNA
<213> ORGANISM: Artificial Sequence
<220> FEATURE:
<223> OTHER INFORMATION: EPSPSinversion checkF5

<400> SEQUENCE: 95
ggcgtcattc catggttgat tgt 23

<210> SEQ ID NO 96
<211> LENGTH: 25
<212> TYPE: DNA
<213> ORGANISM: Artificial Sequence
<220> FEATURE:
<223> OTHER INFORMATION: EPSPSinversion checknestF6

<400> SEQUENCE: 96
gatagaccca gatgggcata gaatc 25

-continued

<210> SEQ ID NO 97
<211> LENGTH: 22
<212> TYPE: DNA
<213> ORGANISM: Artificial Sequence
<220> FEATURE:
<223> OTHER INFORMATION: EPSPSinversion checkR5

<400> SEQUENCE: 97
tgcatgcatt gatggttggt gc 22

<210> SEQ ID NO 98
<211> LENGTH: 25
<212> TYPE: DNA
<213> ORGANISM: Artificial Sequence
<220> FEATURE:
<223> OTHER INFORMATION: EPSPSinversion checknestR6

<400> SEQUENCE: 98
ccggccctta gaataaaggt agtag 25

<210> SEQ ID NO 99
<211> LENGTH: 20
<212> TYPE: DNA
<213> ORGANISM: Artificial Sequence
<220> FEATURE:
<223> OTHER INFORMATION: AtPPO-guide RNA1

<400> SEQUENCE: 99
caaaccaaag aaaaagtata 20

<210> SEQ ID NO 100
<211> LENGTH: 20
<212> TYPE: DNA
<213> ORGANISM: Artificial Sequence
<220> FEATURE:
<223> OTHER INFORMATION: AtPPO-guide RNA2

<400> SEQUENCE: 100
ggtaatcttc ttcagaagaa 20

<210> SEQ ID NO 101
<211> LENGTH: 20
<212> TYPE: DNA
<213> ORGANISM: Artificial Sequence
<220> FEATURE:
<223> OTHER INFORMATION: AtPPO-guide RNA3

<400> SEQUENCE: 101
atcatcttaa ttctcgatta 20

<210> SEQ ID NO 102
<211> LENGTH: 20
<212> TYPE: DNA
<213> ORGANISM: Artificial Sequence
<220> FEATURE:
<223> OTHER INFORMATION: AtPPO-guide RNA4

<400> SEQUENCE: 102
ttgtgatttc tatctagatc 20